US012788802B2

(12) United States Patent
Bridon

(10) Patent No.: US 12,788,802 B2
(45) **Date of Patent: *Nov. 10, 2026**

(54) BRK PEPTIDES AND METHODS OF USE

(71) Applicant: Concarlo Therapeutics, Inc., Brooklyn, NY (US)

(72) Inventor: Dominique Bridon, Brooklyn, NY (US)

(73) Assignee: Concarlo Therapeutics, Inc., Brooklyn, NY (US)

( * ) Notice: Subject to any disclaimer, the term of this patent is extended or adjusted under 35 U.S.C. 154(b) by 825 days.

This patent is subject to a terminal disclaimer.

(21) Appl. No.: 18/010,145

(22) PCT Filed: Jul. 6, 2021

(86) PCT No.: PCT/US2021/040536

§ 371 (c)(1),
(2) Date: Dec. 13, 2022

(87) PCT Pub. No.: WO2022/010914

PCT Pub. Date: Jan. 13, 2022

(65) Prior Publication Data

US 2023/0293643 A1 Sep. 21, 2023

Related U.S. Application Data

(60) Provisional application No. 63/048,489, filed on Jul. 6, 2020.

(51) Int. Cl.

*A61K 38/45* (2006.01)
*A61K 38/00* (2006.01)
*A61K 45/06* (2006.01)
*A61P 35/00* (2006.01)
*C12N 9/12* (2006.01)
*C12N 15/70* (2006.01)

(52) U.S. Cl.

CPC .............. *A61K 38/45* (2013.01); *A61K 45/06* (2013.01); *A61P 35/00* (2018.01); *C12N 9/12* (2013.01); *C12N 15/70* (2013.01); *C12Y 207/10002* (2013.01); *A61K 38/00* (2013.01); *C07K 2319/10* (2013.01); *C07K 2319/35* (2013.01); *C12N 2800/101* (2013.01)

(58) Field of Classification Search

CPC ......... A61K 38/45; A61K 38/00; A61P 35/00; C12Y 207/10002; C07K 2319/10; C07K 2319/35; C07K 2319/43; C12N 9/12

See application file for complete search history.

(56) References Cited

U.S. PATENT DOCUMENTS 6,436,703 B1 8/2002 Tang et al.
10,702,570 B2 7/2020 Blain
2017/0065662 A1* 3/2017 Blain ................ C07K 14/4702
2019/0369104 A1 12/2019 Blain
2020/0113902 A1 4/2020 Rajagopal et al.
2021/0205319 A1 7/2021 Ruscetti et al.

FOREIGN PATENT DOCUMENTS

WO WO 2004/018641 A2 3/2004
WO WO 2017/147326 A1 8/2017
WO WO 2018/106729 A1 6/2018
WO WO 2022/010914 A2 1/2022

OTHER PUBLICATIONS

Kolahkaj et al. Active targeting carrier for breast cancer treatment: Monoclonal antibody conjugated epirubicin loaded nanoparticle, Journal of Drug Delivery Science and Technology, vol. 53, 2019, 101136 (Year: 2019).*
Marshall et al. Rational design and engineering of therapeutic proteins. Drug Discovery Today vol. 8, Issue 5, Mar. 2003, pp. 212-221 (Year: 2003).*
Notice of Reasons for Rejection for JP2023-501217 mailed Jun. 19, 2025, 13 pages.
Brauer et al., "The Alternative Splice Variant of Protein Tyrosine Kinase 6 Negatively Regulates Growth and Enhances PTK6-Mediated Inhibition of [beta]-Catenin", PLOS One, Mar. 2011, 6(3): e14789.
EP Extended Search Report in European Application No. 21837663, dated Jun. 21, 2024, 10 pages.
Patel et al., "Brk/Protein Tyrosine Kinase 6 Phosphorylates p27 KIPI, Regulating the Activity of Cyclin D-Cyclin-Dependent Kinase 4" Molecular and Cellular Biology, May 2015, 35(9): 1506-1522.
Patel et al., "Dua; Inhibition of CDK4 and CDK2 via Targeting p27 Tyrosine Phosphorylation Induces a Potent and Durable Response in Breast Cancer Cells", Molecular Cancer Research, Mar. 2018, 16(3): 361-377.
Miah et al., "BRK Phosphorylates SMAD4 for Proteasomal Degradation and Inhibits Tumor Suppressor FRK to Control SNAIL, SLUG, and Metastatic Potential," *Sci. Adv.* (2019), 5(10):15 pages.
PCT Search Report and Written Opinion in International Application No. PCT/US2024/024494, dated Aug. 8, 2024, 16 pages.

* cited by examiner

*Primary Examiner* — Christina Bradley
(74) *Attorney, Agent, or Firm* — DLA Piper LLP (US)

(57) ABSTRACT

The invention relates to truncated isolated BRK peptides and functional peptides thereof that inhibit the phosphorylation of p27Kip1 and the resulting kinase activity of CDK2 and CDK4; and to pharmaceutical compositions thereof. The invention further relates to the use of the isolated peptides in methods of treating cancer in subject in need thereof.

12 Claims, 24 Drawing Sheets

Specification includes a Sequence Listing.

FIGURE 1

CCL-1 MDYKDDDDKMVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGLPQPARACELPQGPEPVPRPAAGRALPEARA SEQ ID NO: 1

CCL-2 MVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGVLPQPARACELPQGPEPVPRPAAGRALPEARA SEQ ID NO: 2

CCL-2b MVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGLPQPARACELPQGPEPVPRPAAGRALPEARA SEQ ID NO: 3

CCL-3 MDYKDDDDKMVSRDQAHLGPKYVGLWDFKSRTDEELSFRAGDVFHVARKEEQWWWATLLDEAGGAVAQGYVPHNYLAERETVESEP SEQ ID NO: 4

CCL-4a MDYKDDDDKMVSRDQAHLGPKYVGLWDFKSRTDEELSFRAGDVFHVARKEEQWWWATLLAAAAAAVAQGYVPHNYLAERETVESEP
AGHAGCAALQDLAACRGPAAPERGGLPQPARACELPQGPEPVPRPAAGRALPEARA SEQ ID NO: 5

CCL-4b MVSRDQAHLGPKYVGLWDFKSRTDEELSFRAGDVFHVARKEEQWWWATLLAAAAAAVAQGYVPHNYLAERETVESEP
AGHAGCAALQDLAACRGPAAPERGGVLPQPARACELPQGPEPVPRPAAGRALPEARA SEQ ID NO: 6

CCL-5a DDKDKDYDMVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGLPQPARACELPQGPEPVPRPAAGRALPEARA SEQ ID NO: 7

CCL-5b DDKDKDYDMVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGVLPQPARACELPQGPEPVPRPAAGRALPEARA SEQ ID NO: 8

CCL-6 MDYKDDDDKMVSRDQAHLGPKYVGLWDFKSRTDEELSFRAGDVFHVARKEEQWWWATLLDEAGGAVAQGYVPHNYLAERETVESEP
AGHAGCAALQDLAACRGPAAPERGGVLPQPARACELPQGPEPVPRPAAGRALPEARA SEQ ID NO: 9

CCL-7 MDYKDDDDKMVSRDQAHLGPKYVGLWDFKSRTDEELSFRAGDVFHVARKEEQWWWATLLDEAGGAVAQGYVPHNYLAERETVESEP
AGHAGSAALQDLAASRGPAAPERGGLPQPARA SEQ ID NO: 10

CCL-8 MDYKDDDDKMVSRDQAHLGPKYVGLWDFKRSTDEELSFRAGDVFHVARKEEQWWWATLLDEAGGAVAQGYVPHNYLAERETVESEP
AGHAGSAALQDLAASRGPAAPERGGLPQPARA SEQ ID NO: 11

CCL-9 MDYKDDDDKMVSRDQAHLGPKYVGLWDFKSRTDEELSFRAGDVFHVARKEEQWWWATLLDEAGGAVAQGYVPHNYLAERETVESEP
AGHAGCAALQDLAA SEQ ID NO: 12

CCL-10 MDYKDDDDKMVSRDQAHLGPKYVGLWDFKSRTDEELSFRAGDVFHVARKEEQWWWATLLDEAGGAVAQGYVPHNYLAERETVES SEQ ID NO: 13

CCL-11 KYVGLWDFKSRTDEELSFRAGDVFHVARKEEQWWWATLLDEAGGAVAQGYVPHNYLAERETVESEP
AGHAGSAALQDLAASR SEQ ID NO: 14

CCL-12 MVSRDQAHLGPKYVGLWDFKSRTDEELSFRAGDVFHVARKEEQWWWATLLDEAGGAVAQGYVPHNYLAERETVESEP
AGHAGSAALQDLAASR SEQ ID NO: 15

CCL-13 KYVGLWDFKSRTDEELSFRAGDVFHVARKEEQWWWATLLDEAGGAVAQGYVPHNYLAERETVESEP
AGHAGS SEQ ID NO: 16

CCL-14 MVSRDQAHLGPKYVGLWDFKSRTDEELSFRAGDVFHVARKEEQWWWATLLDEAGGAVAQGYVPHNYLAERETVESEP
AGHAGS SEQ ID NO: 17

CCL-15 MDYKDDDDKMVSRDQAHLGPKYVGLWDFKSRTDEELSFRAGDVFHVARKEEQWWWATLLDEAGGAVAQGYVPHNYLAERETVESEP
GQAPVEDHGRPLCQGRLALCGARLACQAPREGALPGAPAVRPAGPAREAEAAPPAA SEQ ID NO: 18

CCL-16 MDYKDDDDKMVSRDQAHLGPKYVGLWDFKSRTDAALSFRAGDVFHVARKEEQWWWATLLDEAGGAVAQGYVPHNYLAERETVESEP
AGHAGCAALQDLAACRGPAAPERGGLPQPARACELPQGPEPVPRPAAGRALPEARA SEQ ID NO: 19

CCL-17 MDYKDDDDKMVSRDQAHLGPKYVGLWDFKSRTDEELSFRAGDVFHVARKEEQWWWATLLDEAAAAVAQGYVPHNYLAERETVESEP
AGHAGCAALQDLAACRGPAAPERGGLPQPARACELPQGPEPVPRPAAGRALPEARA SEQ ID NO: 20

CCL-18 MDYKDDDDKMVSRDQAHLGPKYVGLWDFKSRTDEELSFRAGDVFHVARKEEQWWWATLLAAAGGAVAQGYVPHNYLAERETVESEP
AGHAGCAALQDLAACRGPAAPERGGLPQPARACELPQGPEPVPRPAAGRALPEARA SEQ ID NO: 21

CCL-19 MVSRDQAHLGPKYVGLWDFKSRTDEELSFRAGDVFHVARKEEQWWWATLLDEAGGAVAQGYVPHNYLAERETVESEP
AGHAGCAALQDLAA SEQ ID NO: 22

CCL-20 MVSRDQAHLGPKYVGLWDFKSRTDEELSFRAGDVFHVARKEEQWWWATLLDEAGGAVAQGYVPHNYLAERETVESEP
AGHAGSAALQDLAA SEQ ID NO: 23

FIGURE 1 (cont.)

CCL-27 [1]MVSRDQAHLGPKYVGLWDFKSRTDEELSFRAGDVFHVARKEEQWWWATLLAAAAAAVAQGYVPHNYLAERETVESEP|
AGHAGSAALQDLAA SEQ ID NO: 24

CCL-21 RRRRRRRRR[1]MVSRDQAHLGPKYVGLWDFKSRTDEELSFRAGDVFHVARKEEQWWWATLLDEAGGAVAQGYVPHNYLAERETVESEP|
AGHAGSAALQDLAA SEQ ID NO: 25

CCL-22 MDYKDDDDK[1]MVSRDQAHLGPKYVGLWDFKSRTDAALSFRAGDVFHVARKEEQWWWATLLDEAGGAVAQGYVPHNYLAERETVESEP| SEQ ID NO: 26

CCL-23 MDYKDDDDK[1]MVSRDQAHLGPKYVGLWDFKSRTDEELSFRAGDVFHVARKEEQWWWATLLDEAAAAVAQGYVPHNYLAERETVESEP| SEQ ID NO: 27

CCL-24 MDYKDDDDK[1]MDYKDDDDKGGVTTFVALYDYESRTETDLSFKKGERLQIVNNTEGDWWLAHSLSDEAGGT SGTSYIPSNYVAPSDSIQA SEQ ID NO: 28

CCL-25 MDYKDDDDK[1]MVSRDQAHLGPKYVGLWDFKSRTDEELSFRAGDVFHVARKEEQWWWATLLAAAGGAVAQGYVPHNYLAERETVESEP| SEQ ID NO: 29

CCL-26 MDYKDDDDK[1]MVSRDQAHLGPKYVGLWDFKSRTDEELSFRAGDVFHVARKEEQWWWATLLAAAAAAVAQGYVPHNYLAERETVESEP| SEQ ID NO: 30

FIGURE 2A

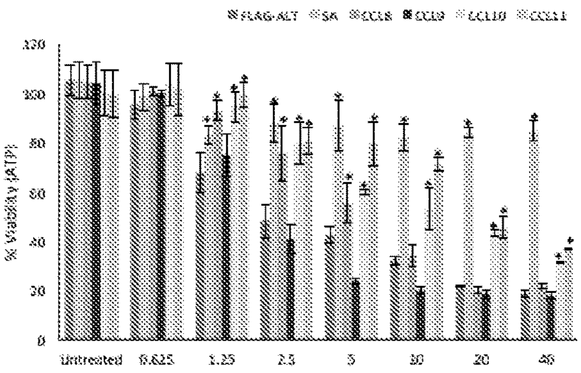

FIGURE 2B

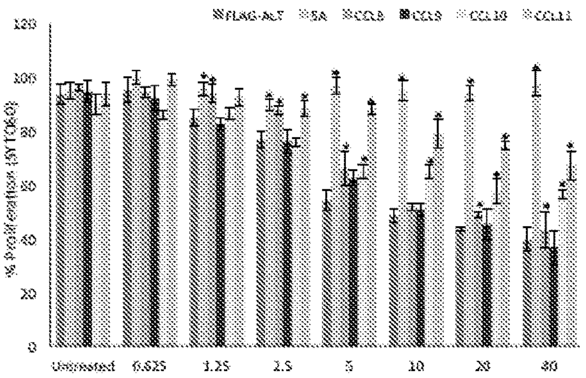

FIGURE 3A

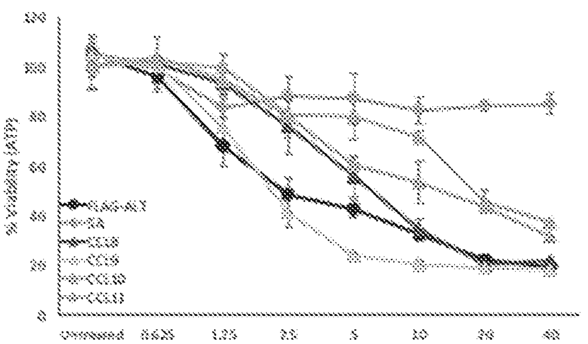

FIGURE 3B

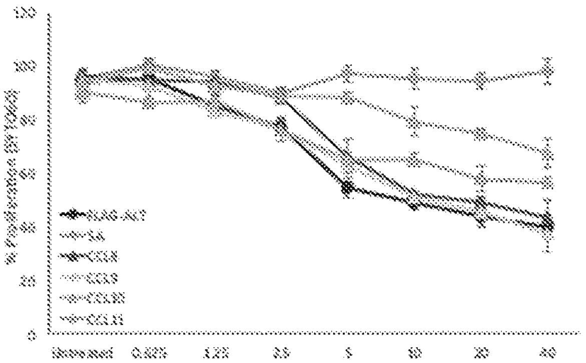

FIGURE 10A
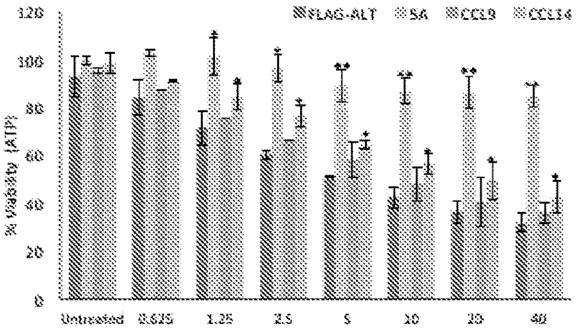
FIGURE 10B
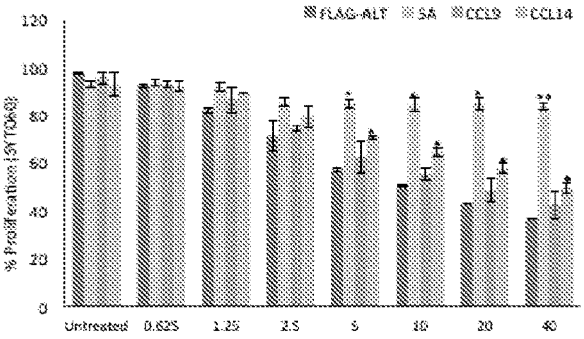
FIGURE 11A
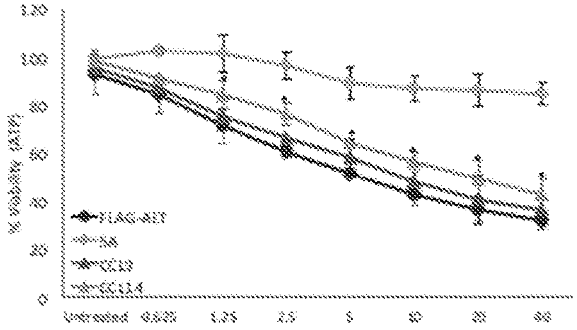
FIGURE 11B
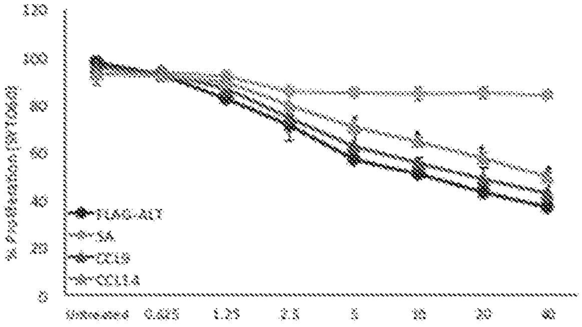
FIGURE 12A
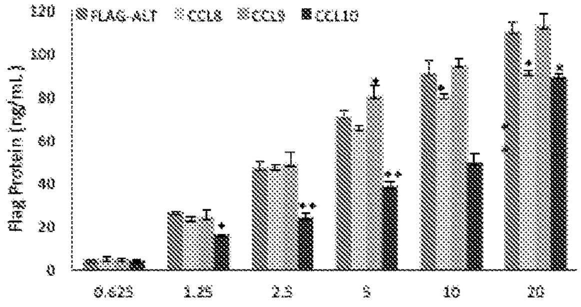
FIGURE 12B
| TREATED [] | FLAG-ALT (ng/ml) | CCL8 (ng/ml) | CCL9 (ng/ml) | CCL10 (ng/ml) |
|---|---|---|---|---|
| 0.625 | 4.05 | 4.67 | 4.88 | 3.99 |
| 1.25 | 26.10 | 23.47 | 24.21 | 16.09 |
| 2.5 | 46.63 | 47.16 | 48.67 | 24.02 |
| 5.0 | 70.65 | 65.24 | 80.08 | 38.21 |
| 10 | 90.37 | 80.16 | 94.22 | 49.36 |
| 20 | 109.54 | 90.88 | 112.27 | 88.99 |

MASS SPECTROMETRY REPORT

MASS SPECTROMETRY REPORT

MASS SPECTROMETRY REPORT

| Size (nm) | Zeta potential (mV) | PDI |
|---|---|---|
| 144.12±7.25 | 25.33±1.85 | 0.19±0.01 |

| Size (nm) | Zeta potential (mV) | PDI |
|---|---|---|
| 86.43±2.50 | 28.97±0.55 | 0.14±0.01 |

| Size (nm) | Zeta potential (mV) | PDI |
|---|---|---|
| 188.83±4.58 | 28.3±0.20 | 0.22±0.05 |

| Size (nm) | Zeta potential (mV) | PDI |
|---|---|---|
| 166.10±7.05 | 28.03±1.14 | 0.16±0.02 |

| n= | 9 | 10 | 9 | 9 | 6 |
|---|---|---|---|---|---|

| n= | 10 | 10 | 10 | 9 | 8 |
|---|---|---|---|---|---|

| n= | 10 | 10 | 10 | 10 | 9 |
|---|---|---|---|---|---|

| n= | 10 | 10 | 10 | 9 | 9 |
|---|---|---|---|---|---|

Method

Detector A 215nm

| Peak# | Ret. Time | Area | Area% |
|---|---|---|---|
| 1 | 9.692 | 734313 | 3.255 |
| 2 | 9.858 | 1493902 | 6.622 |
| 3 | 10.050 | 15925326 | 70.595 |
| 4 | 10.158 | 3211391 | 14.236 |
| 5 | 10.342 | 1193744 | 5.292 |
| Total | | 22558675 | 100.000 |

| CCL20 | Viability $IC_{50}$ (ng/ul) |
|---|---|
| Lot 2- TFA | 6.68 |
| Lot 3- Acetate | 13.46 |
| Lot 3- TFA | 7.81 |

$p<0.05$

BRK PEPTIDES AND METHODS OF USE

CROSS-REFERENCE TO RELATED APPLICATIONS

This application is a 35 USC § 371 National Stage application of International Application No. PCT/US2021/040536 filed Jul. 6, 2021, which claims the benefit under 35 USC § 119(e) to U.S. Application Ser. No. 63/048,489 filed Jul. 6, 2020. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named CONCARLO2000-1_ST25.txt, was created on Dec. 9, 2022 and is 40 kB in size. The file can be accessed using Microsoft Word on a computer that uses Windows OS.

BACKGROUND OF THE INVENTION

Field of The Invention

The present invention relates generally to peptides and more specifically to truncated peptides and uses thereof to inhibit cancer cell proliferation.

Background Information

The G1-S phase cell cycle transition is governed by two cyclin-CDK complexes, cyclin D-CDK4/6 and cyclin E-CDK2. Cyclin D-CDK4 (hereafter CD-K4) phosphorylates the G1 gatekeeper Rb, causing the release of S-phase specific transcription factors, such as E2F. E2F causes the transcriptional induction of Cyclin E, which in turn partners with CDK2 to further phosphorylate Rb and irreversibly cause the transition into S-phase. Cyclin D1 and CDK4 are overexpressed in a variety of human cancers, and, in mouse models, loss of either prevents the development of certain oncogene-driven tumors. Targeting CDK4 activity has been a long-standing goal in the oncology field and because D-K4 is downstream of most oncogenic signaling pathways, targeting this kinase might prevent the resistance that frequently occurs when cell surface or upstream signal transducers are inhibited. The advent of CDK4 specific inhibitors (CDK4i), such as Palbociclib (PD 0332991, hereafter PD), Abemaciclib, or Ribociclib has demonstrated that CDK4 is a promising target. In combination with Letrozole, PD extended median Progression Free Survival (PFS) for metastatic breast cancer patients from 10.2 to 20.2 months (PALOMA trial). However, the overall survival (OS) of patients treated with PD mirrored that seen in patients treated with Letrozole alone, suggesting that resistance to this combination therapy occurs. In tissue culture lines, PD- or Ribociclib-mediated arrest did not appear durable either. While loss of Rb appears to distinguish primary PD-non-responsiveness in cell lines, differences in Ki67, cyclin D, CDK4, and p16 do not appear able to stratify responsive and non-responsive subgroups.

Cyclin D is a transcriptional target of the MAPK pathway, but after cyclin D partners with CDK4, the dimer is unstable, and rapidly dissociates back into the monomeric forms, unless a third protein, p27Kip1 (hereafter p2'7) or p21Cip1, holds the complex together. However, p27 binds to D-K4 in two different conformations: a closed and inactivating conformation OR alternatively, an open and activating form. This transition is mediated by the tyrosine (Y) phosphorylation of p27 on residues Y88 (or Y89) and also on residue Y74 which causes a conformational change, opening the D-K4-p27 ternary complex, thus rendering it able to phosphorylate substrates such as Rb. Non-phosphorylated p27-D-K4 complexes are catalytically inactive because the associated p27 both blocks the ATP binding site on CDK4 and prevents the required CDK Activating Kinase (CAK) phosphorylation of the CDK4 domain itself p27 Y88 is phosphorylated by the Y kinase Brk (Breast tumor Related Kinase or PTK6, Protein Tyrosine Kinase 6) and can be phosphorylated by other non-receptor bound tyrosine kinases including Src and Abl, and interaction between Brk and p27 is mediated though Brk's SH3 domain and a proline-rich binding site in p27. Addition of Brk SH3-containing peptides in vitro blocks this interaction, preventing p27 Y88 phosphorylation, which in turn causes inhibition of CDK4. Overexpression of a naturally occurring ALTternatively-spliced form of Brk (ALT), which contains Brk's SH3 domain, but lacks the SH1 kinase domain, also inhibits Brk's phosphorylation of p2'7, inhibits CDK4, and causes growth arrest, suggesting that inhibition of p27 Y88 phosphorylation might be an alternative way to target CDK4-dependent tumors.

Data suggest that the CDK4i palbociclib associates with the CDK4 free monomer. While it might seem unusual that a kinase inhibitor does not associate with the active form of the kinase, association with monomeric CDK4 would reduce the amount of the ternary complex as well, freeing p27 to be able to associate with and inhibit CDK2. In contrast to CDK4, CDK2 does not require p27 to stabilize the interaction with its cyclin; actually CDK2's phosphorylation of RB is inhibited whenever p27, phosphorylated or not phosphorylated, is associated with the complex. But, even when unable to phosphorylate RB, Y-phosphorylated p27-cyclin E-CDK2 complexes are able to phosphorylate p27 on residue T187, which in vivo, results in decreased p27 stability as it becomes a target for ubiquitin-mediated degradation, reducing p27 association with CDK2, and indirectly activating the cyclin E-CDK2 complex. Thus, blocking pY88 might have the added benefit of preventing p27 degradation and stabilizing p27 in the non-phosphorylated form, permitting it to inhibit CDK2 as well as CDK4. The root of resistance to CDK4 inhibiting therapies, such as PD, is unknown, but one candidate that could compensate for loss of CDK4 activity is CDK2, so a therapy that inhibits both kinases at the outset might offer therapeutic advantages.

Breast cancer is the second leading cause of cancer mortality in women in the USA, with ~40,000 deaths per year; however, besides advances in molecular diagnostics, the extensive intertumoral and intratumoral heterogeneity (i.e., subclones of cells with differing genetic, epigenetic, and/or phenotypic characteristics) remains a significant challenge, as heterogeneity brings clinical and therapeutic consequences in terms of patient prognosis and response to hormonal and targeted therapies, in addition to response to chemotherapies.

Growing knowledge of the molecular underpinnings comprising the etiology of cancer has driven the field of personalized or "precision" medicine to identify specific tumor characteristics and exploit these features by developing targeted therapies against these entities. However, there is still an unmet need for personalized medicine that specifically targets cancer cells and their ability to circumvent cell cycle regulation.

SUMMARY OF THE INVENTION

The present invention is based on the seminal discovery that truncated ALT peptides, rather than the full-length peptide, can specifically inhibit cancer cell proliferation and survival. Such peptides can be incorporated into pharmaceutical compositions and used for the treatment of cancer in a subject in need thereof.

In one embodiment, the invention provides an isolated peptide having an amino acid sequence as set forth in SEQ ID NO:11-13, 17, 22-23 and 25 and functional peptides having at least 90% homology thereto. In one aspect, the isolated peptide further includes an N-terminal modification, a C-terminal modification, a detectable label, a cell penetrating peptide (CPP), a non-natural amino acid, a peptide conjugate, a cyclic peptide, or a combination thereof. In another aspect, the isolated peptide is modified to have improved overall stability, extended blood stream stability, improved cell permeability, improved cellular activity, or a combination thereof, as compared to an unmodified peptide. In some aspects, the detectable label is selected from the group consisting of a fluorescent label, a chromogenic label, a member of a donor/acceptor pair, a stable isotope, and any combination thereof. In some aspects, the CPP improves cellular uptake, cell penetration and/or transport of the peptide. In many aspects, the peptide inhibits cancer cell proliferation and/or decreases cancer cell viability. In some aspects, the peptide inhibits tumor growth. In other aspects, the peptide increases cancer cell death. In various aspects, the peptide increases tumor necrosis. In one aspect, the functional peptide has at least 91%, at least 92%, at least 93%, at least 94%, at least 95%, at least 86%, at least 97%, at least 98% or at least 99% homology to SEQ ID NO:11-13, 17, 22-23 or 25. In another aspect, the peptide has an amino acid sequence as set forth in SEQ ID NO:22 or 23.

In another embodiment, the invention provides an isolated nucleic acid sequence encoding a peptide having an amino acid sequence as set forth in SEQ ID NO:11-13, 17, 22-23 and 25 or functional peptides having at least 90% homology thereto.

In one embodiment, the invention provides a pharmaceutical composition including an isolated peptide having an amino acid sequence as set forth in SEQ ID NO:11-13, 17, 22-23 and 25 or a functional peptide having at least 90% homology thereto and a pharmaceutically acceptable carrier. In one aspect, the pharmaceutical composition further includes a delivery vehicle. In some aspects, the delivery vehicle is selected from the group consisting of a nanoparticle, a liposome, a dendrimer, a micelle, a nanoemulsion, a nanosuspension, a niosome, a nanocapsule, a magnetic nanoparticle, a lipoprotein-based carrier, and a lipoplex nanoparticle. In one aspect, the lipoplex nanoparticle includes 1,2-di-O-octdecenyl-3-trimethyl ammonium propane (DOTMA), cholesterol, DOPE, TPGS, or a combination thereof. In one aspect, the lipid to peptide mass ratio is about 12.5:1. In another aspect, the delivery vehicle is coupled with a targeting antibody or an antibody-drug conjugate (ADC). In other aspects, the delivery vehicle is conjugated with a polyethylene glycol (PEG) polymer or to albumin. In various aspects, the pharmaceutical composition further includes at least one anti-cancer agent. In one aspect, the functional peptide has at least 91%, at least 92%, at least 93%, at least 94%, at least 95%, at least 86%, at least 97%, at least 98% or at least 99% homology to SEQ ID NO:11-13, 17, 22-23 or 25. In another aspect, the isolated peptide has an amino acid sequence as set forth in SEQ ID NO:22 or 23.

In another embodiment, the invention provides a method of treating cancer in a subject including administering to a subject in need thereof a therapeutically effective amount of a pharmaceutical composition including an isolated peptide having an amino acid sequence as set forth in SEQ ID NO:11-13, 17, 22-23 and 25 or a functional peptide having at least 90% homology thereto and a pharmaceutically acceptable carrier. In one aspect, the peptide inhibits the phosphorylation of p27Kip1. In other aspects, the peptide inhibits CDK2 and CDK4. In some aspects, the peptide inhibits cancer cell proliferation and/or decreases cancer cell viability. In other aspects, the peptide inhibits tumor growth. In some aspects, the peptide increases cancer cell death. In other aspects, the peptide increases tumor necrosis. In one aspect, an anti-cancer treatment is further administered to the subject. In one aspect, the anti-cancer treatment is selected from chemotherapy, radiation treatment, immunotherapy, resection of a tumor, and any combination thereof.

BRIEF DESCRIPTION OF THE DRAWINGS

FIG. 1 is a representation of recombinant and synthetic peptides.

FIGS. 2A-2B illustrate the efficacy of peptides CCL-8-CCL-11 compared to Flag-ALT. FIG. 2A illustrates the percent viability of MCF7 after 48 hrs double treatment. FIG. 2B illustrates the percent proliferation after peptide or control treatment for 48 hrs. Values are normalized to empty Nano particle controls for each assessed concentration. *$p<0.05$.

FIGS. 3A-3B illustrate the efficacy of peptides CCL-8-CCL-11 compared to Flag-ALT. FIG. 3A illustrates the percent viability of MCF7 after 48 hrs double treatment. FIG. 3B illustrates the percent proliferation after peptide or control treatment for 48 hrs. Values are normalized to empty Nano particle controls for each assessed concentration. *$p<0.05$.

FIG. 4A illustrates the percent viability of MCF7. FIG. 4B illustrates the percent proliferation after peptide or control treatment for 48 hrs. Values are normalized to empty Nano particle controls for each assessed concentration. *$p<0.05$.

FIG. 5A illustrates the percent viability of MCF7. FIG. 5B illustrates the percent proliferation after peptide or control treatment for 48 hrs. Values are normalized to empty Nano particle controls for each assessed concentration. *$p<0.05$.

FIG. 6A illustrates the percent viability of MCF7 after 48 hrs double treatment. FIG. 6B illustrates the percent proliferation after peptide or control treatment for 48 hrs. Values are normalized to empty Nano particle controls for each assessed concentration. Data represent averages from two biological replicas. *$p<0.05$; **$p<0.005$.

FIG. 7A illustrates the percent viability of MCF7 after 48 hrs double treatment. FIG. 7B illustrates the percent proliferation after peptide or control treatment for 48 hrs. Values are normalized to empty Nano particle controls for each assessed concentration. Data represent averages from two biological replicas. *$p<0.05$; **$p<0.005$.

FIG. 8A illustrates the percent viability of MCF7 after 48 hrs double treatment. FIG. 8B illustrates the percent proliferation after peptide or control treatment for 48 hrs. Values are normalized to empty Nano particle controls for each assessed concentration. *p<0.05; **p<0.005.

FIG. 9A illustrates the percent viability of MCF7 after 48 hrs double treatment. FIG. 9B illustrates the percent proliferation after peptide or control treatment for 48 hrs. Values are normalized to empty Nano particle controls for each assessed concentration. *p<0.05; **p<0.005.

FIGS. 10A-10B illustrate the efficacy of peptides CCL-9 and CCL-14 compared to Flag-ALT. FIG. 10A illustrates the percent viability of MCF7. FIG. 10B illustrates the percent proliferation after peptide or control treatment for 48 hrs. Values are normalized to empty Nano particle controls for each assessed concentration. Data represent averages from two biological replicas for CCL-14 and three biological replicas for CCL-9. *p<0.05; **p<0.005.

FIGS. 11A-11B illustrate the efficacy of peptides CCL-9 and CCL-14 compared to Flag-ALT. FIG. 11A illustrates the percent viability of MCF7 after 48 hrs double treatment. FIG. 11B illustrates the percent proliferation after peptide or control treatment for 48 hrs. Values are normalized to empty Nano particle controls for each assessed concentration. Data represent averages from two biological replicas for CCL-14 and three biological replicas for CCL-9. *p<0.05; **p<0.005.

FIGS. 12A-12D illustrate a flag Eliza assay to quantify amount of flag peptide after two 24 hr treatments of NP-peptide/FLAG-ALT in MCF7 cells. FIG. 12A illustrates Flag Eliza capturing total amount of FLAG-protein in increasing concentrations of NP-peptide treated cells. FIG. 12B illustrates a table presenting numerical values of ng/mL of FLAG peptide captured in each treated concentration. FIG. 12C illustrates equalizing for amount of flag peptide detected to compare proliferation and viability percentages in 10 ng/ul treatment with FLAG-ALT and CCL-9 to 20 ng/ul of CCL-8 and CCL-10. FIG. 12D illustrates equalizing for amount of flag peptide detected to compare proliferation and viability percentages in 2.5 ng/ul treatment with FLAG-ALT and CCL-9 to 10 ng/ul of CCL-8 and CCL-10. *p<0.05; **p<0.005.

FIG. 13A illustrates the percent viability of MCF10A after 48 hrs double treatment. FIG. 13B illustrates the percent proliferation was determined by assessing the level of SYTO60 dye incorporation after peptide or control treatment for 48 hrs. Values are normalized to empty Nano particle controls for each assessed concentration. *p<0.05; **p<0.005.

FIG. 14A illustrates the percent viability of MCF10A after 48 hrs double treatment. FIG. 14B illustrates the percent proliferation was determined by assessing the level of SYOT60 dye incorporation after peptide or control treatment for 48 hrs. Values are normalized to empty Nano particle controls for each assessed concentration. *p<0.05; **p<0.005.

FIG. 15A illustrates the percent viability of MCF10A and MCF7 cells after 48 hrs double treatment. FIG. 15B illustrates the percent proliferation was determined by assessing the level of SYTO60 dye incorporation after peptide or control treatment for 48 hrs. Values are normalized to empty Nano particle controls for each assessed concentration. *p<0.05; **p<0.005.

FIG. 16A illustrates the percent viability of MCF10A and MCF7 cells after 48 hrs double treatment. FIG. 16B illustrates the percent proliferation was determined by assessing the level of SYTO60 dye incorporation after peptide or control treatment for 48 hrs. Values are normalized to empty Nano particle controls for each assessed concentration. *p<0.05; **p<0.005.

FIG. 17A illustrates the quantification of FLAG protein in 4 different concentrations of drug prior to cell treatment: NP-FLAG ALT and CCL-8-10 in cell culture media. FIG. 17B illustrates the Flag Eliza capturing total amount of FLAG-protein in increasing concentrations of NP-peptide treated MCF10A cells after 2 24 hrs treatments. FIG. 17C illustrates the Flag Eliza capturing total amount of FLAG-protein in 0.625 ng/ul of NP-peptide treated MCF10A cells after 2 24 hrs treatments. FIG. 17D illustrates the Flag Eliza capturing total amount of FLAG-protein in 2.5 ng/ul of NP-peptide treated MCF10A cells after 2 24 hrs treatments. FIG. 17E illustrates the Flag Eliza capturing total amount of FLAG-protein in 5 ng/ul of NP-peptide treated MCF10A cells after 2 24 hrs treatments. FIG. 17F illustrates the Flag Eliza capturing total amount of FLAG-protein in 20 ng/ul of NP-peptide treated MCF10A cells after 2 24 hrs treatments. *p<0.05; **p<0.005.

FIG. 18A illustrates CCL-8 HPLC trace. FIG. 18B illustrates CCL-8 MS.

FIG. 19A illustrates CCL-9 HPLC trace. FIG. 19B illustrates CCL-9 MS.

FIG. 20A illustrates CCL-9 HPLC trace. FIG. 20B illustrates CCL-10 MS.

FIG. 21A illustrates CCL-20 HPLC trace. FIG. 21B illustrates CCL-20 MS.

FIG. 24A illustrates cell proliferation assay results. FIG. 24B illustrates encapsulation efficiency assay results.

FIG. 25A is a graph illustrating ATP viability measured in MCF7 cells. N=4. FIG. 25B is a graph illustrating ATP viability measured in T47D cells. N=3.

28A illustrates tumor volume in mice treated with vehicle. FIG. 28B illustrates tumor volume in mice treated with CCL-2/NPx (peptide to lipid ratio: 1:10). FIG. 28C illustrates tumor volume in mice treated with CCL-2/NPx (1:12.5). FIG. 28D illustrates tumor volume in mice treated with CCL-19/NPx (1:12.5). FIG. 28E illustrates tumor volume in mice treated with CCL-20/NPx (1:12.5).

FIG. 29A illustrates change in tumor volume at day 2. FIG. 29T illustrates change in tumor volume at day 21. *$p\leq0.05$, $p\leq0.01$, * $p\leq0.001$, **** $p\leq0.0001$.

FIG. 30A illustrates changes in body weight of mice treated with vehicle. FIG. 30B illustrates changes in body weight of mice treated with CCL-2/NPx (1:10). FIG. 30C illustrates changes in body weight of mice treated with CCL-2/NPx (1:12.5). FIG. 30D illustrates changes in body weight of mice treated with CCL-19/NPx (1:12.5). FIG. 30E illustrates changes in body weight of mice treated with CCL-20/NPx (1:12.5).

FIG. 31A illustrates the percent viability of MCF7 cells after treatment with 10 ng/ul or 20 ng/ul of peptides. FIG. 31B illustrates the percent viability of MCF10A cells after treatment with 10 ng/ul or 20 ng/ul of peptides. FIG. 31C illustrates the changes in tumor volumes in a MCF7 breast cancer tumor model. Data are shown as Mean±SEM; **$p<0.005$.

FIG. 33A illustrates the percent necrosis in the tumors over time. FIG. 33B illustrates the percent of phosphor positive cells over time. FIG. 33C illustrate the percent of CDK2phos over time. FIG. 33D illustrates the percent of Ki67 positive cells over time.

FIG. 34A illustrates tumor volume with IpY.20 as compared to a vehicle over time. FIG. 34B illustrates tumor growth rate during the treatment period.

FIG. 35A illustrates CCL-20 acetate HPLC trace. FIG. 35B illustrates CCL-20 acetate MS.

FIG. 38A is a graph illustrating platelet count. FIG. 38B shows the analysis of serum cytokines (IL-10, IL-12p70, IL-17, IP-10 and G-CSF).

DETAILED DESCRIPTION OF THE INVENTION

Figure 4A:
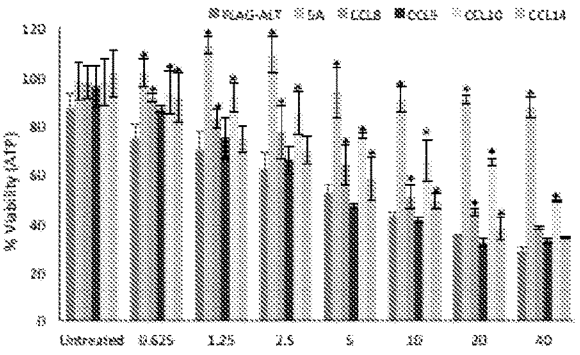
FIGS. 4A-4B illustrate the efficacy of peptides CCL-8-10 and CCL-14 compared to Flag-ALT.
Figure 4B:
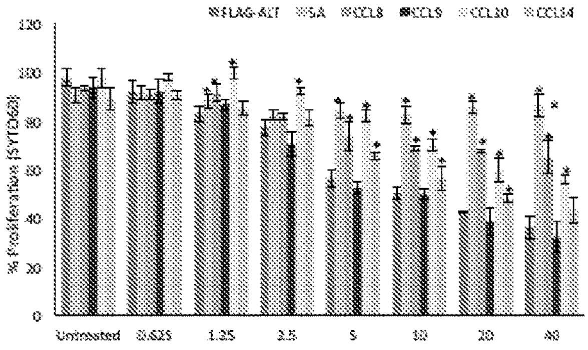
Figure 5A:
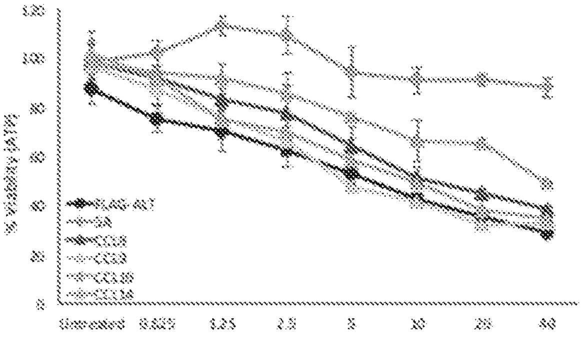
FIGS. 5A-5B illustrate the efficacy of peptides CCL-8-10 and CCL-14 compared to Flag-ALT.
Figure 5B:
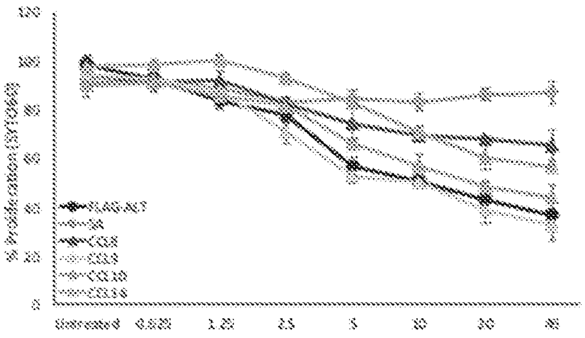
Figure 6A:
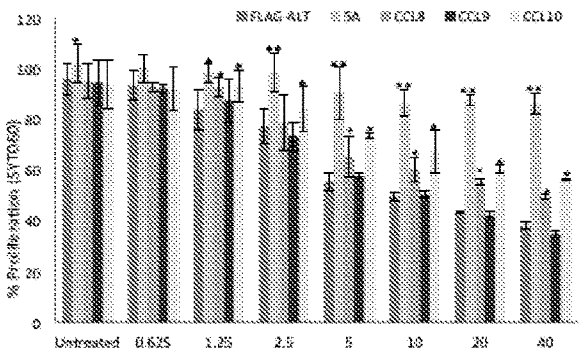
FIGS. 6A-6B illustrate the efficacy of peptides CCL-8-10 compared to Flag-ALT.
Figure 6B:
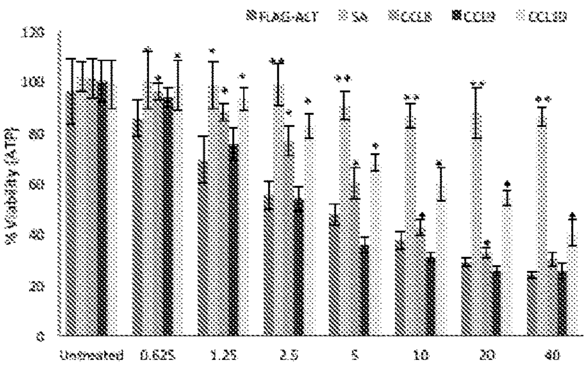
Figure 7A:
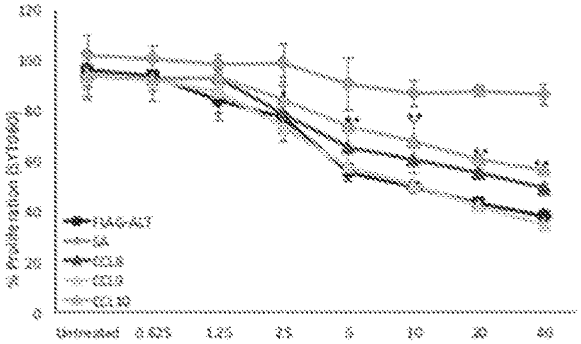
FIGS. 7A-7B illustrate the efficacy of peptides CCL-8-10 compared to Flag-ALT.
Figure 7B:
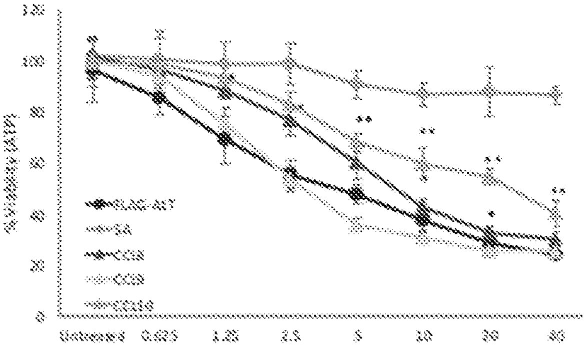
Figure 8A:
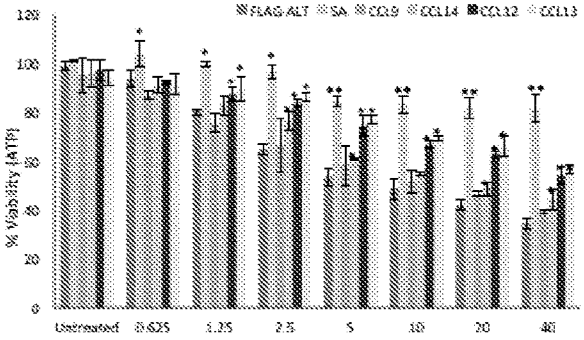
FIGS. 8A-8B illustrate the efficacy of peptides CCL-12-14 and CCL-9 compared to Flag-ALT.
Figure 8B:
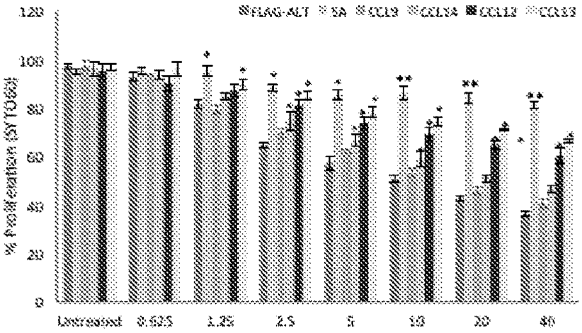
Figure 9A:
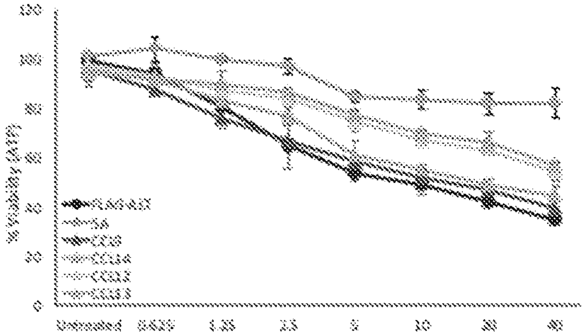
FIGS. 9A-9B illustrate the efficacy of peptides CCL-12-14 and CCL-9 compared to Flag-ALT.
Figure 9B:
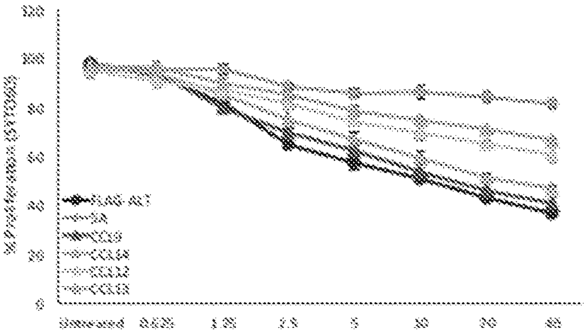
Figure 12C:
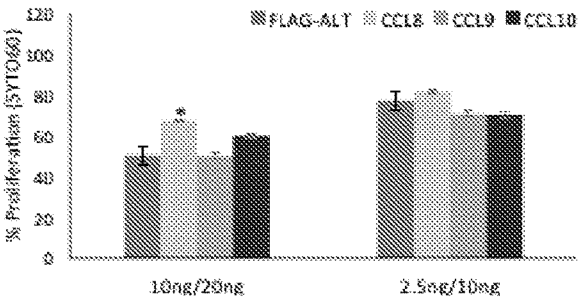
Figure 12D:
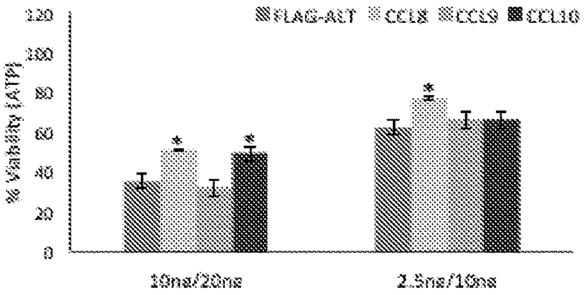
Figure 13A:
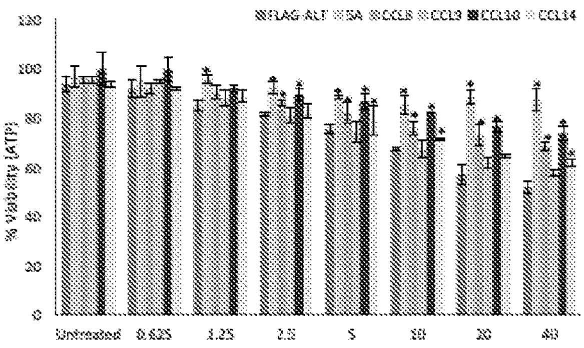
FIGS. 13A-13B illustrate the efficacy of peptides CCL-8-CCL-10 and CCL-14 compared to Flag-ALT in MCF10A cells.
Figure 13B:
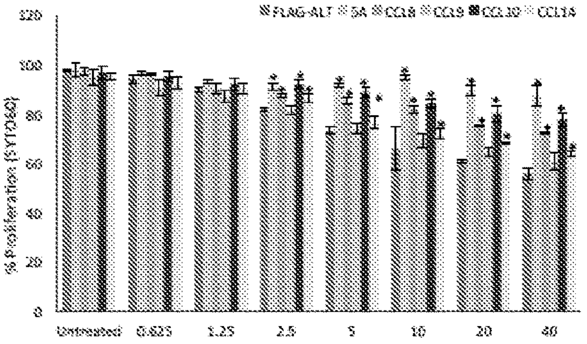
Figure 14A:
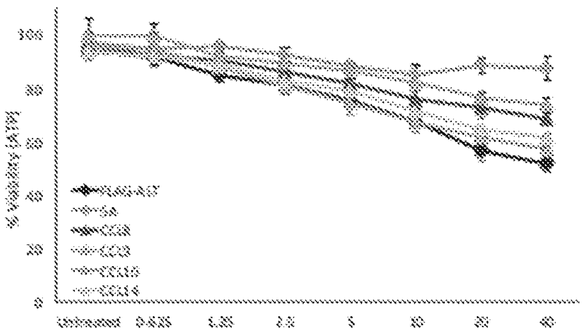
FIGS. 14A-14B illustrate the efficacy of peptides CCL-8-CCL-10 and CCL-14 compared to Flag-ALT in MCF10A cells.
Figure 14B:
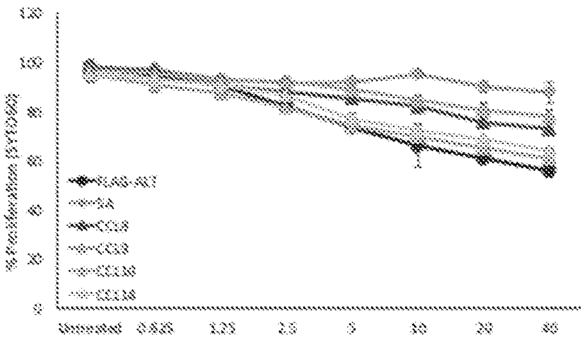
Figure 15A:
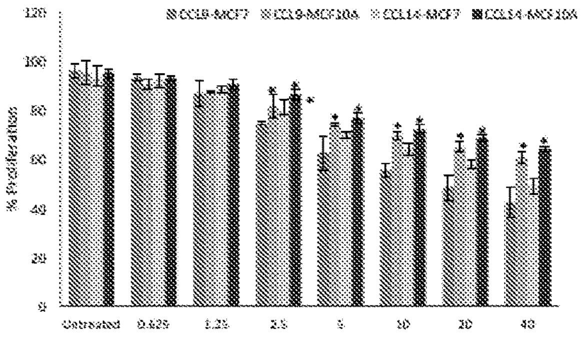
FIGS. 15A-15B illustrate the functional comparison between % cell proliferation and % cell viability in MCF7 and MCF10A cells after treatment with CCL-9 and CCL-14.
Figure 15B:
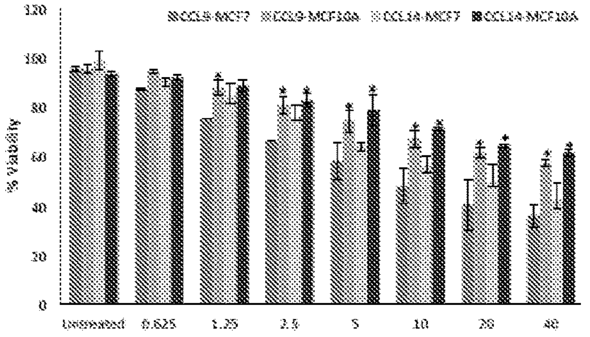
Figure 16A:
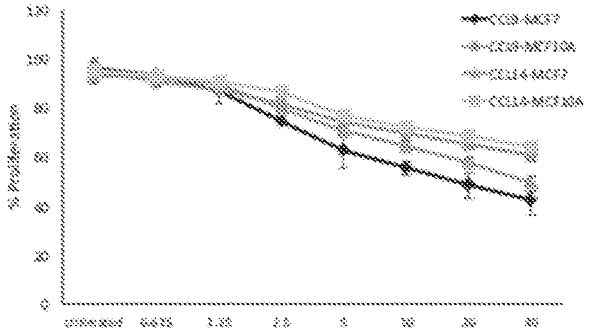
FIGS. 16A-16B illustrate the functional comparison between % cell proliferation and % cell viability in MCF7 and MCF10A cells after treatment with CCL-9 and CCL-14.
Figure 16B:
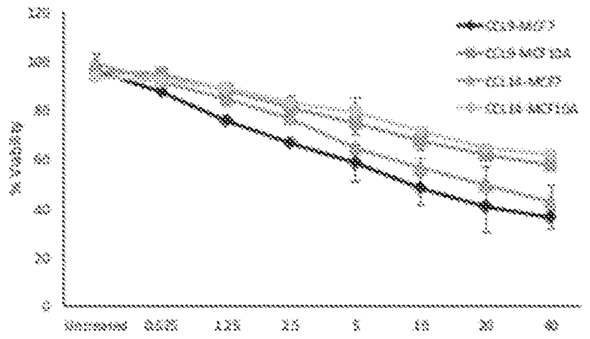
Figure 17A:
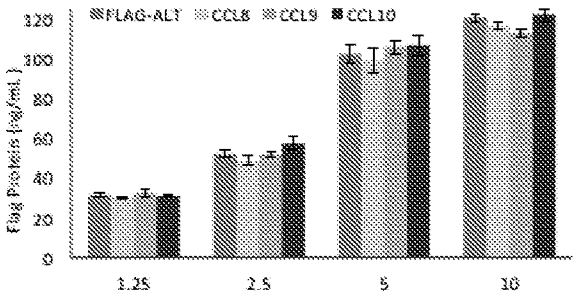
FIGS. 17A-17F illustrate a Flag Eliza assay to quantify amount of flag peptide preceding treatment and after 2-24 hrs treatment in MCF7 and MCF10A cells.
Figure 17B:
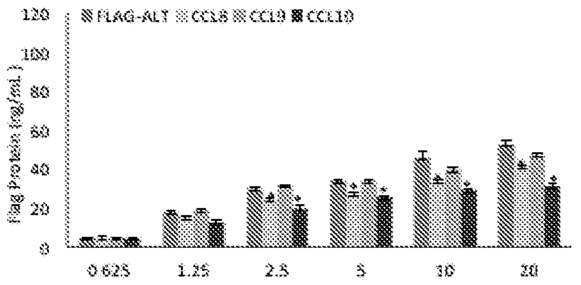
Figure 17C:
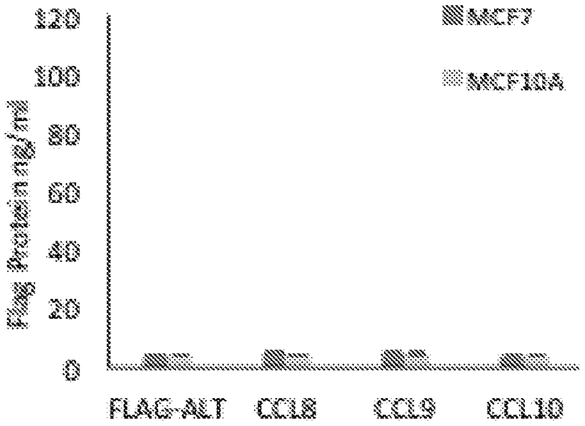
Figure 17D:
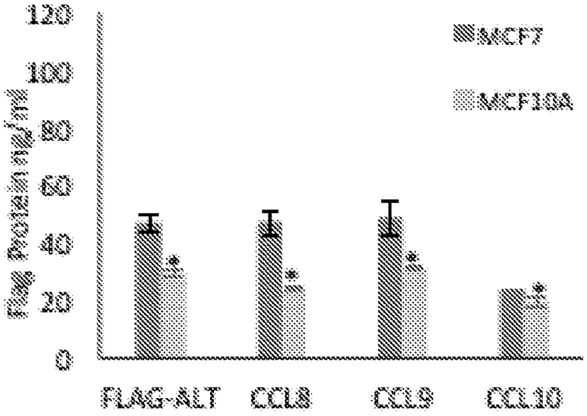
Figure 17E:
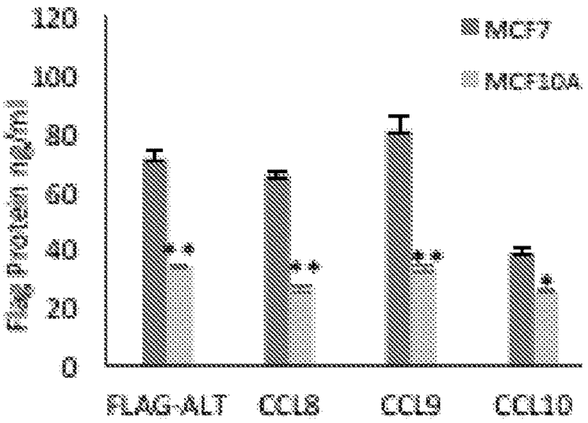
Figure 17F:
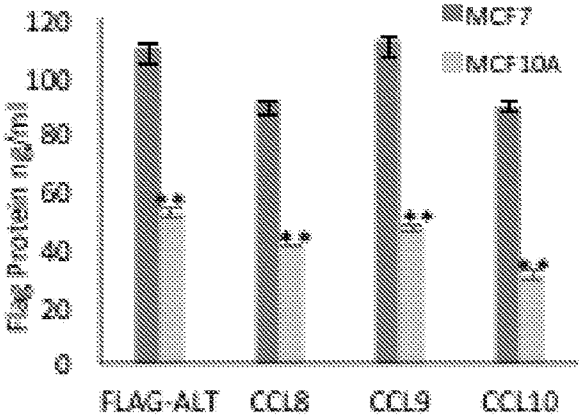

The present invention is based on the seminal discovery that certain truncated ALT peptides specifically inhibit cancer cell proliferation and survival and can be incorporated into pharmaceutical compositions and used for the treatment of cancer in a subject in need thereof.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

In one embodiment, the invention provides an isolated peptide having an amino acid sequence as set forth in SEQ ID NO:11-13, 17, 22-23 and 25 and functional peptides having at least 90% homology thereto.

The terms "peptide", "polypeptide" and "protein" are used interchangeably herein and refer to any chain of at least two amino acids, linked by a covalent chemical bound. A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

In one aspect, a peptide of the invention has a certain homology to the peptide provided in SEQ ID NO:11 or SEQ ID NO:12 or SEQ ID NO:22 or SEQ ID NO:23 or SEQ ID NO:25 or SEQ ID NO:13 or SEQ ID NO:17. As used herein, the term “homology” or a percentage of homology refers to the identity or percent identity in the context of two or more nucleic acids or polypeptides, which are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. For example, an isolated functional peptide of the invention can have an amino acid having at least 50%, 60%, 70%, 80%, 90%, 91%, 92%, 93%, 94%, 95%, 96%, 97%, 98%, 99% or more homology to SEQ ID NO: 11-13, 17, 22-23 or 25.

In some aspects, the functional peptides have at least 90%, 91%, 92%, 93%, 94%, 95%, 96%, 97%, 98% or at least 99% homology to the sequences provided herein, for example, SEQ ID NOs: 11-13, 17, 22-23 and 25.

A “functional peptide” as used herein is a peptide of the invention that is a modified version of the original peptide, e.g., amino acid changes, mutations, deletions, and the like, but retains the function of the original peptide. For example, a functional peptide of SEQ ID NO:22 may include additional amino acids or a deletion of one or more amino acids, but the function of the functional peptide is the same or similar to the function of SEQ ID NO:22. In one aspect, the invention provides functional peptides of SEQ ID NO: 11-13, 17, 22-23 or 25. In a preferred embodiment, the peptide has an amino acid sequence as set forth in SEQ ID NO:22 or 23.

In one aspect, the isolated peptide further includes an N-terminal modification, a C-terminal modification, a detectable label, a cell penetrating peptide (CPP), a non-natural amino acid, a peptide conjugate, a cyclic peptide, or a combination thereof. In some aspects, the detectable label is selected from the group consisting of a fluorescent label, a chromogenic label, a member of a donor/acceptor pair, a stable isotope, and any combination thereof.

Virtually any modification of the peptides of the invention can be performed, and is included in the present disclosure, as long as it is not detrimental to the properties of the peptide (the impact of a modification of a peptide on its activity can be routinely assessed, and modeling tools can be used to predict the impact of the modification of the peptides on their activity). Alternatively, small cleavable components can be incorporated if there are any concerns regarding a loss of activity due to the position of a peptide modification (such as a CPP for example).

Non-limiting examples of N-terminal modification that can be introduced at the N-terminal extremity of the isolated peptide of the invention include: 5-FAM, 5-FAM-Ahx, Abz, acetylation, Acryl, Alloc, Benzoyl, Biotin, Biotin-Ahx, BOC, Br-Ac-, BSA (—NH2 of N terminal), CBZ, Dansyl, Dansyl-Ahx, Decanoic acid, DTPA, Fatty Acid, FITC, FITC-Ahx, Fmoc, Formylation, Hexanoic acid, HYNIC, KLH (—NH2 of N terminal), Lauric acid, Lipoic acid, Maleimide, MCA, Myristoyl, Octanoic acid, OVA (—NH2 of N terminal), Palmitoyl, PEN, Stearic acid, Succinylation, and TMR.

Non-limiting examples of C-terminal modification that can be introduced at the C-terminal extremity of on the isolated peptide of the invention include: AFC, AMC, Amidation, BSA (—COOH of C terminal), Bzl, Cysteamide, Ester (OEt), Ester (OMe), Ester (OtBu), Ester (OTBzl), KLH (—COOH of C terminal), MAPS Asymmetric 2 branches, MAPS Asymmetric 4 branches, MAPS Asymmetric 8 branches, Me, NHEt, NHisopen, NHMe, OSU, OVA (—COOH of C terminal), p-Nitroanilide, and tBu.

Non-limiting examples of peptide conjugate include: BSA (—COOH of C terminal), BSA conjugation on cysteine, KLH (—NH2 of N terminal), KLH conjugation on cysteine, OVA (—COOH of C terminal), OVA (—NH2 of N terminal), and OVA conjugation on cysteine.

“Cyclic peptides” are polypeptide chains which contain a circular sequence of bonds through a connection between the amino and carboxyl ends of the peptide, a connection between the amino end and a side chain, or two side chains or more complicated arrangements. Even though most cyclic peptides are membrane impermeable, some cyclic peptides have unique features that allow cell entry by passive diffusion, endocytosis, endosomal escape or other mechanisms. Therefore, cyclic peptides can also be used as conjugate peptides, to improve cell permeability of a peptide of the invention (also referred to as cargo peptide).

The peptides of the invention can be labeled in various ways, to allow their detection and/or distinction from other peptides. The peptides can for example be labeled by the incorporation of stable radioisotopes in amino acids. Non-limiting examples of radiolabeled amino acids include: Arg ($^{13}C_6$, $^{15}N_4$), Ile ($^{13}C_6$, $^{15}N$), Leu ($^{13}C_6$,$^{15}N$) Lys ($^{13}C_6$, $^{15}N_2$), and Val($^{13}C_5$, $^{15}N$). Peptides can also be labeled by the incorporation of non-conventional or non-natural amino acids.

The peptides can also be labeled by the addition of a fluorescent label, dye or tag to the amino acid sequence of the peptide. As used herein, the terms “fluorescent peptide”, “fluorescent tag”, “fluorophore” and the like are interchangeable. Non-limiting examples of fluorescent label, dye or tag include: IRDye680RD, 1-pyrenemethylamine HCL, 5-FAM (N-Terminal), 5-FAM-Ahx (N-Terminal), Abz/DNP, Abz/Tyr (3-NO2), DABCYL, DABCYL/Glu(EDANS)-NH2, Dansyl (N-Terminal), Dansyl-Ahx (N-Terminal), EDANS/DABCYL, FITC (N-Terminal), FITC-Ahx (N-Terminal), Glu (EDANS)-NH2, MCA (N-Terminal), MCA/DNP, quenched fluorescent peptide, Tyr (3-NO2), TMR, AMC, CF, TAMRA, RhB, MCA, NBD, PBA, BODIPY, fragmented BODIPY.

The peptides can also be labeled by the incorporation of a chemiluminescent label, such as luciferin or luminol; or by the incorporation of a member of a donor/acceptor pair, such as mClover3/mRuby3, EBFP2/mEGFP, ECFP/EYFP, Cerulean/Venus, MiCy/mKO, CyPet/YPet, EGFP/mCherry, Venus/mCherry, Venus/tdTomato, and Venus/mPlum for example.

Additional modifications of the peptide can include peptide cyclization through the creation of disulfide bridges between cysteine residues on the peptide, phosphorylation, methylation, PEGylation, multiple antigen peptide (MAP) application, and any additional modification of a peptide known in the art.

In another aspect, the isolated peptide is modified to have improved overall stability, extended blood stream stability, improved cell permeability, improved cellular activity, or a combination thereof, as compared to an unmodified peptide. In some aspects, the CPP improves cellular uptake, cell penetration and/or transport of the peptide.

As used herein "improved" stability, cell permeability or cellular activity is meant to refer to the stability, cell permeability or cellular activity of the peptide that is increased, ameliorated or augmented when the peptide is modified, as compared to the same peptide without such modification. As used herein blood stream stability of the peptide refers to the amount of time that the peptide stays in the blood stream, which can be measured by evaluating the peptide half-life for example. An "extended" stability of a modified peptide indicates that the peptide can be detected in the blood stream for longer periods of time when it is modified, as compared to when it is not.

The peptide of the invention can for example include a short polypeptide sequences, such as a CPP, which efficiently transports biologically active molecule inside living cells, and improves cellular uptake of the peptide of interest. Cellular uptake of the peptide can be measured, for example, as the ratio of cytosol versus extracellular concentration of the peptide.

In other aspects, the CPP is selected from the group consisting of penetratin, Tat peptide, Tat peptide variants, pVEC, chimeric transportan, MPG peptide, linear and cyclic polyarginines, R8 (SEQ ID NO:37), R9 (SEQ ID NO:38), R6W3 (SEQ ID NO:40), EB1, VP22, model amphipathic peptide (MAP), Pep-1 and Pep-1 related peptides, fusion sequence-based protein (FBP), transportan analog 7 (TP-7), TP-9, TP-10, azurin and azurin derivatives, protamine, protamine-fragment/SV40 peptides, polyethylenimine (PEI), poly-lysine, histidine-lysine peptides, poly-arginine, complex cyclic polycationic arginine containing peptides and gp41 fusion sequence.

CPP and protein transduction domains (PTD) are well known in the art for their ability to efficiently transport biologically active molecule inside living cells. CPP are typically less than 30 residues in length (see Table 1), and often carry a positive charge. The CPP or cyclic peptide and the cargo peptide can be covalently conjugated, or physically complexed through non-covalent interaction by bulk-mixing of the CPP and the cargo. Each CPP has physicochemical properties, preferred mode of administration, specific barrier and preferred target cell, which need to be taken into account when pairing a CPP to a cargo protein. Further modification of the CPP or cyclic peptide, such as Na-methylation can be used to increase permeabilization of the peptide.

TABLE 1 sequences of CPPs

| CPP | Sequence | SEQ ID NO: |
|---|---|---|
| penetratin | RQIKIWFQNR RMKWKK | SEQ ID NO: 31 |
| Tat peptide | GRKKRRQRRR PPQ | SEQ ID NO: 32 |
| pVEC | LLIILRRRIR KQAHAHSK | SEQ ID NO: 33 |

TABLE 1-continued sequences of CPPs

| CPP | Sequence | SEQ ID NO: |
|---|---|---|
| Chimeric transportan | GWTLNSAGYL LGKINLKALA ALAKKIL | SEQ ID NO: 34 |
| MPG peptide | GALFLGFLGA AGSTMGAWSP KKKRKV | SEQ ID NO: 35 |
| Pep-1 | KETWWETWWT EWSQPKKKRK V | SEQ ID NO: 36 |
| synthetic polyarginines ($R_n$; 6 < n < 12) | | |
| $R_8$ | RRRRRRRR | SEQ ID NO: 37 |
| $R_9$ | RRRRRRRRR | SEQ ID NO: 38 |
| MAP | KLALKLALK ALKAALKLA | SEQ ID NO: 39 |
| $R_6W_3$ | RRWWRRWRR | SEQ ID NO: 40 |
| P28 (azurin 50-77) | LSTAADMQG VVTDGMASG LDKDYLKPDD | SEQ ID NO: 41 |
| Complex cyclic arginine containing | Described in U.S. patent application 20200385427 | |

In a preferred aspect, the invention peptides inhibit cancer cell proliferation and/or decreases cancer cell viability. In various aspects, the peptide inhibits tumor growth, increases cancer cell death, and/or increases tumor necrosis.

In another embodiment, the invention provides an isolated nucleic acid sequence encoding a peptide having an amino acid sequence as set forth in SEQ ID NO: 11-13, 17, 22-23 or 25 or functional peptides having at least 90% homology thereto.

In one embodiment, the invention provides a pharmaceutical composition including an isolated peptide having an amino acid sequence as set forth in SEQ ID NO: 11-13, 17, 22-23 or 25 or a functional peptide having at least 90% homology thereto and a pharmaceutically acceptable carrier.

Also disclosed herein are pharmaceutically acceptable salts and prodrugs of the disclosed compounds. Pharmaceutically acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, trifluoroacetate, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, "pharmaceutical composition" refers to a formulation comprising an active ingredient, and optionally a pharmaceutically acceptable carrier, diluent or excipient. The term "active ingredient" can interchangeably refer to an "effective ingredient" and is meant to refer to any agent that is capable of inducing a sought-after effect upon administration. In one embodiment, the active ingredient includes a biologically active molecule. As used herein, the phrase "biologically active molecule" refers to a molecule that has a biological effect in a cell. In certain embodiments the active molecule may be an inorganic molecule, an organic molecule, a small organic molecule, a drug compound, a peptide, a polypeptide, such as an enzyme or transcription factor, an antibody, an antibody fragment, a peptidomimetic, a lipid, a nucleic acid such as a DNA or RNA molecule, a ribozyme, hairpin RNA, siRNA (small interfering RNAs) of varying chemistries, miRNA, siRNA-protein conjugate, an siRNA-peptide conjugate, and siRNA-antibody conjugate, an antagomir, a PNA (peptide nucleic acid), an LNA (locked nucleic acids), or a morpholino. In certain illustrative embodiments, the active agent is a polypeptide or peptide having an amino acid sequence as set forth in SEQ ID NO:10-15 or 19 or a functional peptide having at least 90% homology thereto. In a preferred embodiment, the isolated peptide has an amino acid sequence as set forth in SEQ ID NO:22 or 23.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

The pharmaceutical composition of the present invention can be prepared, for example, in liquid form, or can be in dried powder form (e.g., lyophilized). Particular methods of administering pharmaceutical compositions are described below.

In one aspect, the pharmaceutical composition further includes a delivery vehicle.

The delivery vehicle is a system compatible with the other ingredients of the formulation, and not deleterious to the recipient thereof, nor to the activity of the active ingredient of the formulation, that is used to successfully address delivery-related problems, to carry the peptide of interest to the desired sites of therapeutic action while reducing adverse side effects, and to allow its efficient penetration inside the target cell.

In some aspects, the delivery vehicle is selected from the group consisting of a nanoparticle, a liposome, a dendrimer, a micelle, a nanoemulsion, a nanosuspension, a niosome, a nanocapsule, a magnetic nanoparticle, a lipoprotein-based carrier, and a lipoplex nanoparticle.

The term "nanoparticle is used to define particle of matter that is between 1 and 150 nanometers (nm) in diameter. Nanoparticles occur in a great variety of shapes, which have been given many informal names such as nanospheres, nanorods, nanochains, nanostars, nanoflowers, nanoreefs, nanowhiskers, nanofibers, and nanoboxes. The shapes of nanoparticles may be determined by the intrinsic crystal habit of the material, or by the influence of the environment around their creation. Medicinal application of nanoparticle involves silver, gold, hydroxyapatite, clay, titanium dioxide, silicon dioxide, zirconium dioxide, carbon, diamond, aluminum oxide and ytterbium trifluoride as the base material. Semi-solid and soft nanoparticles such as liposome can also be generated. Various types of liposome nanoparticles are currently used clinically as delivery systems for anticancer drugs and vaccines.

"Nanocapsule" refers to a thin membrane surrounding a core (liquid, solid) and having a size ranging from 10 nm to 1000 nm. Nanocapsules are submicroscopic colloidal drug carrier systems composed of an oily or an aqueous core surrounded by a thin polymer membrane, which may be composed of natural or synthetic polymers.

A "magnetic nanoparticle" is a nanoparticle having magnetic core with a polymer or metal coating which can be functionalized or may consist of porous polymers that contain magnetic nanoparticles precipitated within the pores. By functionalizing the polymer or metal coating it is possible to attach, for example, cytotoxic drugs for targeted chemotherapy or therapeutic peptide. Once attached, the particle/therapeutic agent complex is injected into the bloodstream, often using a catheter to position the injection site near the target. Magnetic fields, generally from high-field, high-gradient, rare earth magnets are focused over the target site and the forces on the particles as they enter the field allow them to be captured and extravasated at the target.

The term "liposome" or "lipoplex nanoparticle" refers to non-toxic, non-hemolytic, and non-immunogenic lipid-based, ligand-coated nanocarriers that can store their payload in the hydrophobic shell or the hydrophilic interior depending on the nature of the drug/contrast agent being carried. Liposomes are biocompatible and biodegradable and can be designed to avoid clearance mechanisms (reticuloendothelial system (RES), renal clearance, chemical or enzymatic inactivation, etc.). Polyethylene glycol (PEG) can be added to the surface of the liposomes to increase their relatively low stability in vitro; PEGylation of the liposomal nanocarrier elongates the half-life of the construct while maintaining the passive targeting mechanism that is commonly conferred to lipid-based nanocarriers.

Other lipid-based nanocarriers include nanoemulsion and lipoprotein-based carrier. As used herein, the term "nanoemulsion" refers to a colloidal system consisting of mainly oil, surfactant, and water, and having a high kinetic stability, low viscosity. Non limiting examples of oils that can be used in the formation of nanoemulsion include castor oil, corn oil, coconut oil, evening primrose oil, linseed oil, mineral oil, olive. Emulgent such as natural lecithins from plant or animal source, phospholipids, castor oil can be part of the composition of the nanoemulsion. Non-limiting examples of surfactant or co-surfactant include polysorbate20, polysorbate80, polyoxy60, castor oil, sorbitan monooleate, ethanol, glycerin, PEG300, PEG400, polyene glycol, and poloxamer. Lipoprotein-based carrier include lipoproteins, which are biological lipid carriers playing important role in transport of fats within the body. These are natural nanoparticles which serve as drug-delivery vehicles due to their small size, long residence time in the circulation. Examples of lipoprotein include low-density lipoprotein (LDL), which carries cholesterol in plasma. Lipoproteins carry high-drug payload and are used as delivery vehicles for transportation of chemotherapeutic agents.

As used herein, "dendrimer" and "micelle" can be used interchangeably and refer to polymeric based delivery vehicles. Polymeric micelles can be prepared from certain amphiphilic co-polymers consisting of both hydrophilic and hydrophobic monomer units. Dendrimers have a core that branches out in regular intervals to form a small, spherical, and very dense nanocarrier.

A "nanosuspension", as used herein consists of a pure poorly water-soluble drug without any matrix material suspended in dispersion. Preparation of nanosuspension is simple and applicable to all drugs which are water insoluble.

As used herein, "niosome" refers to a drug delivery vehicle including nonionic surfactants capable of entrap hydrophilic and lipophilic compound. Niosomes are vesicles composed of non-ionic surfactants, which are biodegradable, relatively nontoxic, more stable and inexpensive, an alternative to liposomes. The properties of the vesicles can be changed by varying the composition of the vesicles, size, lamellarity, tapped volume, surface charge and concentration.

In one aspect, the lipoplex nanoparticle includes 1,2-di-O-octdecenyl-3-trimethyl ammonium propane (DOTMA), cholesterol, DOPE, TPGS, or a combination thereof.

In other aspects, the lipoplex nanoparticle includes DOTMA and cholesterol at a molar ratio from about 10:90 to 90:10. In some aspects, the lipoplex nanoparticle includes DOTMA and cholesterol at a molar ratio from about 40:50 to 50:39. In one aspect, the lipoplex nanoparticle includes DOTMA, cholesterol and TPGS at a molar ratio of about 50:49:1.

In one aspect, a lipid to peptide mass ratio is about 8:1, about 6:1, 5:1, about 10:1, about 12.5:1, about 15:1, about 20:1, about 25:1, about 30:1 or about 35:1. In some aspects, the lipid to peptide mass ratio is about 10:1. In a preferred embodiment, the lipid to peptide mass ratio is about 12.5:1.

The isolated peptide of the invention can be encapsulated using various nanoparticle formulations, which maintain the properties of the peptide (i.e., CDK4 and CDK2 dual inhibition for efficient use as a breast cancer therapy).

The use of lipoplex nanoparticle for the liposomal encapsulation of the peptide can for example include a combination of DOTMA, cholesterol, DOPE, and TPGS. Non-limiting examples of such combination are presented in Table 2.

TABLE 2

Illustrative Lipoplex nanoparticle formulations

| NP ID | DOTMA | CHOLESTEROL | DOPE | TPGS |
|---|---|---|---|---|
| 1 | 50 | 49 | 0 | 1 |
| 2 | 45 | 54 | 0 | 1 |
| 3 | 40 | 59 | 0 | 1 |
| 4 | 50 | 45 | 0 | 5 |
| 5 | 45 | 50 | 0 | 5 |
| 6 | 40 | 55 | 0 | 5 |
| 8 | 45 | 45 | 0 | 10 |
| 9 | 40 | 50 | 0 | 10 |
| 10 | 50 | 39 | 10 | 1 |

Empty lipoplex nanoparticle are first generated, for example using the ethanol injection method, where the lipids mixture in ethanol that consists of DOTMA, cholesterol, DOPE and TPGS is quickly injected into HEPES buffer (pH=7.4) to achieve 10% ethanol and 90% aqueous in the final mixture, to form the empty lipoplex nanoparticle. The empty lipoplex nanoparticle can then be mixed with the peptide at a chosen lipid to peptide mass ratio to generate lipoplex nanoparticle including the isolated peptide of interest.

Useful cationic lipids with respect to the present invention include but are not limited to: DDAB, dimethyldioctadecyl ammonium bromide: N-1-(2,3-dioloyloxy)propyl-N,N,N-trimethyl ammonium methyl sulfate; 1,2-diacyloxy-3-trimethylammonium propanes, (including but not limited to, dioleoyl (DOTAP), dilauroyloxy, dimyristoyloxy, dipalmitoyloxy, and distearoyloxy); N-1-(2,3-dioleoyloxy)propyl-N,N-dimethyl amine; 1,2-diacyl-3-dimethylammonium propanes, (including but not limited to, dioleoyl (DODAP), dilauroyl, dimyristoyl, dipalmitoyl, and di stearoyl); DOTMA, N-1-2,3-bis(oleyloxy)propyl-N,N,N-trimethylammonium chloride, (including but not limited to, dioleyl (DOTMA), dilauryl, dimyristyl, dipalmityl, and distearyl); DOGS, dioctadecylamidoglycylspermine; DC-cholesterol, 3 B—N (N',N'dimethylaminoethane) carbamoylcholesterol: DOSPA, 2,3-dioleoyloxy-N-(2-(sperminecarboxamido)-ethyl)-N,N-dimethyl-1-propanaminium trifluoroacetate; 1,2-diacyl-sn-glycero-3-ethylphosphocholines (including but not limited to dioleoyl (DOEPC), dilauroyl, dimyristoyl, dipalmitoyl, distearoyl, and palmitoyl-oleoyl); B-alanyl cholesterol: CTAB, cetyl trimethyl ammonium bromide: diC14-amidine, N-t-butyl-N'-tetradecyl-3-tetradecylaminopropionamidine; 14 Dea2; TMAG, N-(alpha-trimethylammonioacetyl)didodecyl-D-glutamate chloride; O,O'-ditetradecanoyl-N-(trimethylammonioacetyl) diethanolamine chloride: DOSPER, 1,3-dioleoyloxy-2-(6-carboxy-spermyl)-propylamide; N,N,N',N'-tetramethyl N,N'-bis(2-hydroxylethyl)-2,3-dioleoyloxy-1,4-butanediammonium iodide, 1-2-(acyloxy)ethyl-2-alkyl (alkenyl)-3-(2-hydroxyethyl)imidazolinium chloride, derivatives such as DOTIM, 1-2-(9(Z)-octadecenoyloxy) ethyl-2-(8(Z)-heptadecenyl-3-(2-hydroxyethyl) imidazolinium chloride; DPTIM, 1-2-(hexadecanoyloxy)ethyl)-2-pentadecyl-3-(2-hydroxyethyl)imidazolinium chloride; 2,3-dialkyloxypropyl quaternary ammonium compound derivatives, contain a hydroxyalkyl moiety on the quaternary amine such as: DORI, 1,2-dioleoyl-3-dimethyl-hydroxyethyl ammonium bromide: DORIE, 1,2-dioleyloxy-propyl-3-dimethyl-hydroxyethyl ammonium bromide: DORIE-HP 1,2-dioley bromide: DORIE-HB, 1,2-dioleyloxypropyl-3-dimethyl hydroxybutyl ammonium bromide: DORIE-HPe, 1,2-dioleyloxypropyl-3-dimethyl-hydroxypentyl ammonium bromide; DMRIE, 1,2-dimyristyloxypropyl-3-dimethyl-5 hydroxylethyl ammonium bromide: DPRIE, 1,2-dipalmityloxypropyl-3-dimethyl-hydroxyethyl ammonium bromide; DSRIE, 1,2-disteryloxypropyl-3-dimethyl-hydroxyethyl ammonium bromide.

Other liposomes are included in this invention. For instance, one aspect of this present invention provides a liposome comprising between 25% and 45% (mol/mol) of an anionic lipid. The content of anionic lipid affects important characteristics of the liposome, such as lipid hydrolysis of the liposome and also the immune response toward the liposome. As the content of anionic lipid increases, so does the rate of lipid hydrolysis (and the release of drug). It has been demonstrated that a reasonable rate of hydrolysis can be achieved by anionic lipid content between 25% and 45%. Thus, in one embodiment, the content of anionic lipid is at least 25%. In another embodiment, the content of anionic lipid is no more than 45%. In yet another embodiment, the anionic lipid content of the liposome is selected from the group consisting of between 25% and 45%, 28% and 42%, 30% and 40%, 32% and 38% and 34% and 36%. The immune response toward the liposomes can be affected by the content of anionic lipid. Thus, the clearance rate of the liposome in body may be reduced by keeping the content of the anionic lipid in the liposome below a certain level and the content of anionic lipid in the liposome can be used to strike a balance between hydrolysis rate and clearance by the reticuloendothelial system.

Preferably the anionic lipid is a phospholipid and preferably, the phospholipid is selected from the group consisting of PI (phosphatidyl inositol), PS (phosphatidyl serine), DPG (bisphosphatidyl glycerol), PA (phosphatidic acid), PEOH (phosphatidyl alcohol), and PG (phosphatidyl glycerol). More preferably, the anionic phospholipid is PG.

Particular attention is also given to the composition of Hydrophilic polymers. In a preferred embodiment, the liposome further comprises a hydrophilic polymer selected from the group consisting of PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly(ethylene oxide)], chitosan [poly(D-glucosamine)], PAA [poly (aminoacid)], polyHEMA [Poly(2-hydroxyethylmethacrylate)] and co-polymers thereof. Most preferably the polymer is PEG with a molecular weight between 100 Da and 10 kDa. Particular preferred are PEG sizes of 2-5 kDa (PEG2000 to PEG5000), and most preferred is PEG2000.

The inclusion of polymers on liposomes is well known to the skilled artisan and can be used to increase the half-life of the liposomes in the bloodstream, presumably by reducing clearance by the reticuloendothelial system. Preferably, the polymer is conjugated to the head group of phosphatidyl ethanolamine. Another option is ceramide. The polymer-conjugated lipid is preferably present at an amount of at least 2%. More preferably, the amount is at least 5% and no more than 15%. Even more preferably, the amount of polymer-conjugated lipid is at least 3% and no more than 6%. Liposomes containing anionic phospholipids and ≤2.5% DSPE-PEG2000 have increased tendency to aggregate in the presence of calcium. This can usually be observed by formation of high viscous gel. Liposomes containing anionic phospholipids and >7.5% causes the liposomes to sediment or phase separate.

Neutrally Charged Lipid Components in the Liposome:

Preferably, the liposome of the invention also comprises an uncharged phospholipid selected from the group consisting of zwitterionic phospholipids comprising PC (phosphatidyl choline) and PE (phosphatidylethanolamine). Most preferably, the zwitterionic phospholipid is PC. In contrast to anionic phospholipid, zwitterionic phospholipid serves as a charge neutral lipid component in the liposome. By combining zwitterionic- and anionic phospholipid in the same liposome, it is possible to adjust to a desired surface charge density which complies with both sufficiently high intra-cellular hydrolysis and a low clearance rate in the blood. The amount of zwitterionic phospholipid in the liposome is preferably between 40% and 75% and more preferably between 50 and 70%.

Ether-Phospholipids:

Some or all of the phospholipids may be ether-phospholipids. Thus, they may harbor an ether-bond instead of an ester-bond at the sn-1 position of the glycerol backbone of the phospholipid. When intracellular phospholipases hydrolyze this particular type of phospholipids, mono-ether lyso-phospholipids are produced, and these are toxic to e.g. cancer cells. I.e. ether phospholipids may be seen as pro-drugs of mono-ether lyso-phospholipids and liposomes of the invention can be used to deliver such pro-drugs to the environment of cancer cells, where the pro-drugs are activated by phospholipase hydrolysis.

Such nanoparticle formulations were tested for characteristics that would shield the protein therapeutic from enzymatic degradation during systemic delivery, create an appropriately charged shell that would facilitate passive transport across the cell membrane, and possibly induce optimal uptake by the tumor environment. Determining of the optimal nanoparticle formulation(s) can for example include determining encapsulation efficiency, to compare nanoparticle packaging; determining proliferation of the cells, to determine growth inhibitory efficacy of the encapsulated peptides in cancer cell lines; and determining the rate of uptake, to determine delivery kinetics in cancer cell lines.

In one aspect, the delivery vehicle is coupled with a targeting antibody or an antibody-drug conjugate (ADC).

As used herein the term "antibody" (Ab) refers to glycoproteins having binding specificity to a specific antigen. The antibody that can be coupled to the delivery vehicle of the invention include natural or artificial, mono- or polyvalent antibodies including, but not limited to, polyclonal, monoclonal, multispecific, human, humanized or chimeric antibodies, single chain antibodies, and antibody fragments (including any portion of an intact antibody, preferably the antigen binding or variable region of the intact antibody). Examples of antibody fragments include Fab, Fab' and F(ab')2, Fc fragments or Fc-fusion products, single-chain Fvs (scFv), disulfide-linked Fvs (sdfv) and fragments including either a VL or VH domain; diabodies, tribodies and the like (Zapata et al. Protein Eng. 8(10):1057-1062 [1995]).

The antibody can be a "targeting antibody", having a specific antigen-binding specificity to a target of interest. For example, the delivery vehicle of the present invention can be couple with antibody having an antigen-binding specificity toward an antigen specifically expressed by cancer cell, to deliver the pharmaceutical composition of the present invention specifically to the cancer cells expressing the cancer-associated antigen.

Alternatively, the antibody can be an antibody-drug conjugate (ADC), which is an anticancer drug coupled to a targeting antibody. The biochemical reaction between the antibody and the target antigen triggers a signal in the cancer cell, which then absorbs or internalizes the antibody together with the linked cytotoxin. After the ADC is internalized, the cytotoxin kills the cancer cell.

In other aspects, the delivery vehicle is conjugated with a polyethylene glycol (PEG) polymer or to albumin.

In various aspects, the pharmaceutical composition further includes at least one anti-cancer agent.

The term "anti-cancer agent" can refer to any agent, small molecule, drug and the like that can be used to treat cancer, such as chemotherapy, immunotherapy, targeted therapy, and checkpoint inhibitor therapy.

Examples of chemotherapy include treatment with a chemotherapeutic, cytotoxic or antineoplastic agents including, but not limited to, (i) anti-microtubules agents comprising vinca alkaloids (vinblastine, vincristine, vinflunine, vindesine, and vinorelbine), taxanes (cabazitaxel, docetaxel, larotaxel, ortataxel, paclitaxel, and tesetaxel), epothilones (ixabepilone), and podophyllotoxin (etoposide and teniposide); (ii) antimetabolite agents comprising anti-folates (aminopterin, methotrexate, pemetrexed, pralatrexate, and raltitrexed), and deoxynucleoside analogues (azacitidine, capecitabine, carmofur, cladribine, clofarabine, cytarabine, decitabine, doxifluridine, floxuridine, fludarabine, fluorouracil, gemcitabine, hydroxycarbamide, mercaptopurine, nelarabine, pentostatin, tegafur, and thioguanine); (iii) topoisomerase inhibitors comprising Topoisomerase I inhibitors (belotecan, camptothecin, cositecan, gimatecan, exatecan, irinotecan, lurtotecan, silatecan, topotecan, and rubitecan) and Topoisomerase II inhibitors (aclarubicin, amrubicin, daunorubicin, doxorubicin, epirubicin, etoposide, idarubicinm, merbarone, mitoxantrone, novobiocin, pirarubicin, teniposide, valrubicin, and zorubicin); (iv) alkylating agents comprising nitrogen mustards (bendamustine, busulfan, chlorambucil, cyclophosphamide, estramustine phosphate, ifosamide, mechlorethamine, melphalan, prednimustine, trofosfamide, and uramustine), nitrosoureas (carmustine (BCNU), fotemustine, lomustine (CCNU), N-Nitroso-N-methylurea (MNU), nimustine, ranimustine semustine (MeCCNU), and streptozotocin), platinum-based (cisplatin, carboplatin, dicycloplatin, nedaplatin, oxaliplatin and satraplatin), aziridines (carboquone, thiotepa, mytomycin, diaziquone (AZQ), triaziquone and triethylenemelamine), alkyl sulfonates (busulfan, mannosulfan, and treosulfan), non-classical alkylating agents (hydrazines, procarbazine, triazenes, hexamethylmelamine, altretamine, mitobronitol, and pipobroman), tetrazines (dacarbazine, mitozolomide and temozolomide); (v) anthracyclines agents comprising doxorubicin and daunorubicin. Derivatives of these compounds include epirubicin and idarubicin; pirarubicin, aclarubicin, and mitoxantrone, bleomycins, mitomycin C, mitoxantrone, and actinomycin; (vi) enzyme inhibitors agents comprising FI inhibitor (Tipifarnib), CDK inhibitors (Abemaciclib, Alvocidib, Palbociclib, Ribociclib, and Seliciclib), PrI inhibitor (Bortezomib, Carfilzomib, and Ixazomib), PhI inhibitor (Anagrelide), IMPDI inhibitor (Tiazofurin), LI inhibitor (Masoprocol), PARP inhibitor (Niraparib, Olaparib, Rucaparib), HDAC inhibitor (Belinostat, Panobinostat, Romidepsin, Vorinostat), and PIKI inhibitor (Idelalisib); (vii) receptor antagonist agent comprising ERA receptor antagonist (Atrasentan), Retinoid X receptor antagonist (Bexarotene), Sex steroid receptor antagonist (Testolactone); (viii) ungrouped agent comprising Amsacrine, Trabectedin, Retinoids (Alitretinoin Tretinoin) Arsenic trioxide, Asparagine depleters (Asparaginase/Pegaspargase), Celecoxib, Demecolcine Elesclomol, Elsamitrucin, Etoglucid, Lonidamine, Lucanthone, Mitoguazone, Mitotane, Oblimersen, Omacetaxine mepesuccinate, and Eribulin.

Examples of immunotherapy include treatment with antibodies including, but not limited to, alemtuzumab, AVASTIN™ (bevacizumab), BEXXAR™ (tositumomab), CDP 870, and CEA-Scan (arcitumomab), denosumab, ERBITUX™ (cetuximab), HERCEPTIN™ (trastuzumab), HUMIRA™ (adalimumab), IMC-IIF 8, LEUKOSCAN™ (sulesomab), MABCAMPATH™ (alemtuzumab), MABTHERA™ (Rituximab), matuzumab, MYLOTARG™ (gemtuzumab oxogamicin), natalizumab, NEUTROSPEC™ (Technetium (99mTc) fanolesomab), panitumamab, PANOREX™ (Edrecolomab), PROSTASCINT™ (Indium-Ill labeled Capromab Pendetide), RAPTIVA™ (efalizumab), REMICADE™ (infliximab), REOPRO™ (abciximab), rituximab, SIMULECT™ (basiliximab), SYNAGIS™ (palivizumab), THERACIM HR3™, tocilizumab, TYSABRI™ (natalizumab), VERLUMA™ (nofetumomab), XOLAIR™ (omalizumab), ZENAPAX™ (dacliximab), ZEVALIN™ (ibritumomab tiuxetan (IDEC-Y2B8) conjugated to yttrium 90), GILOTRIF™ (afatinib), LYNPARZA™ (olaparib), PERJETA™ (pertuzumab), OPDIVO™ (nivolumab), BOSULIF™ (bosutinib), CABOMETYX™ (cabozantinib), trastuzumab-dkst (OGIVRI™), SUTENT™ (sunitinib malate), ADCETRIS™ (brentuximab vedotin), ALECENSA™ (alectinib), CALQUENCE™ (acalabrutinib), YESCARTA™ (ciloleucel), VERZENIO™ (abemaciclib), KEYTRUDA™ (pembrolizumab), ALIQOPA™ (copanlisib), NERLYNX™ (neratinib), IMFINZI™ (durvalumab), DARZALEX™ (daratumumab), TECENTRIQ™ (atezolizumab), and TARCEVA™ (erlotinib).

"Checkpoint inhibitor therapy" is a form of cancer treatment that uses immune checkpoints which affect immune system functioning. Immune checkpoints can be stimulatory or inhibitory. Tumors can use these checkpoints to protect themselves from immune system attacks. Checkpoint therapy can block inhibitory checkpoints, restoring immune system function. Checkpoint proteins include programmed cell death 1 protein (PDCD1, PD-1; also known as CD279) and its ligand, PD-1 ligand 1 (PD-L1, CD274), cytotoxic T-lymphocyte-associated protein 4 (CTLA-4), A2AR (Adenosine A2A receptor), B7-H3 (or CD276), B7-H4 (or VTCN1), BTLA (B and T Lymphocyte Attenuator, or CD272), IDO (Indoleamine 2,3-dioxygenase), KIR (Killer-cell Immunoglobulin-like Receptor), LAG3 (Lymphocyte Activation Gene-3), TIM-3 (T-cell Immunoglobulin domain and Mucin domain 3), and VISTA (V-domain Ig suppressor of T cell activation).

In some aspects, the functional peptides have at least 91%, 92%, 93%, 94%, 95%, 96%, 97%, 98% or at least 99% homology to SEQ ID NO: 11-13, 17, 22-23 or 25.

In another embodiment, the invention provides a method of treating cancer in a subject including administering to a subject in need thereof a therapeutically effective amount of a pharmaceutical composition including an isolated peptide having an amino acid sequence as set forth in SEQ ID NO:

11-13, 17, 22-23 or 25 or a functional peptide having at least 90% homology thereto and a pharmaceutically acceptable carrier. In a preferred embodiment, the isolated peptide has an amino acid sequence as set forth in SEQ ID NO:22 or 23.

The term "subject" as used herein refers to any individual or patient to which the methods of the invention are performed. Generally, the subject is human, although as will be appreciated by those in the art, the subject may be an animal. Thus, other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

By "therapeutically effective amount", "effective dose," "therapeutically effective dose", "effective amount," or the like it is meant an amount of the pharmaceutical composition of the invention that will elicit the biological or medical response of a tissue, system, animal or human that is being sought by the researcher, veterinarian, medical doctor or other clinician. Generally, the response is either amelioration of symptoms in a patient or a desired biological outcome (e.g., reduction of tumor volume, or increased survival of the subject).

"Administration of" or "administering" should be understood to mean providing the pharmaceutical composition of the invention in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization. The phrases "parenteral administration" and "administered parenterally" as used herein means modes of administration other than enteral and topical administration.

In some aspects, the administration of the pharmaceutical composition is intracutaneous, subcutaneous, intravenous, intraperitoneal, intraarterial, intrathecal, intracapsular, intraorbital, intracardiac, intradermal, transdermal, transtracheal, subcuticular, intraarticular, subcapsular, subarachnoidal, intraspinal, intrasternal, oral, sublingual, buccal, rectal, vaginal, nasal or ocular, or by infusion, inhalation, or nebulization. In other aspects, the pharmaceutical compositions can be delivered in a controlled release system, such as using an intravenous infusion, an implantable osmotic pump, a transdermal patch, liposomes, or other modes of administration. In one aspect, the pharmaceutical composition is administered intravenously.

Administration may be by single or multiple doses, alone or in combination with an additional therapy, as discussed below. The amount of isolated peptide and the frequency of dosing may be optimized by a physician for each particular patient. In one aspect, the pharmaceutical composition is administered is a single dose, daily.

The term "cancer" refers to a group of diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

As used herein, "neoplasm" or "tumor" including grammatical variations thereof, means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like.

Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer, Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland's Cancer, Childhood; Sarcoma, Ewing's Family of Tumors; Sarcoma, Kaposi's; Sarcoma (Osteosarcoma Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; Wilms' Tumor; and metastases thereof.

In various aspects, the cancer is selected from the group consisting of breast, brain, thyroid, prostate, colorectal, pancreas, cervix, stomach, endometrium, liver, bladder, ovary, testis, head and neck, skin, mesothelial lining white blood cells, esophagus, muscle, connective tissue, lung, adrenal gland, kidney, bone or testicle cancer, and metastasis thereof.

In one aspect, the peptide inhibits the phosphorylation of p27. In other aspects, the peptide inhibits CDK2 and CDK4. In some aspects, the peptide inhibits cancer cell proliferation and/or decreases cancer cell viability.

The peptides of the present invention are truncated ALT peptides, which are p27 mimetics that inhibit the phosphorylation of tyrosine of p27, thereby disturbing the kinase activity of CDK4 and inhibiting cancer cell progression into the cell cycle.

Alt-Brk is an ALTternatively-spliced form of Brk containing the SH3 domain, which blocks pY88 and acts as an endogenous CDK4 inhibitor, and therefore was identified as a targetable regulatory region within p27. Brk is overexpressed in 60% of breast carcinomas, suggesting that it facilitates cell cycle progression by modulating CDK4 through p27 tyrosine phosphorylation. Phosphorylation of Tyr-88/Tyr-89 in the 310 helix of p27 and possibly Y74 reduces its cyclin-dependent kinase (CDK) inhibitory activity. This causes a conformational change in the p27-cyclin D-CDK4 complex, permitting p27 to vacate the catalytic cleft to allow ATP access and further phosphorylation of the active site. Thus, phosphorylation of this site can switch the tumor suppressive CDK inhibitory activity to an oncogenic activity.

Blocking CDK4 activity has long been a goal in cancer therapy. However, this has proven difficult due to the conservation between the active sites of serine/threonine kinases. Most inhibitors reacted with too many other essential kinases to provide any therapeutic benefit. Palbociclib is a CDK4 inhibitor, that appears to be extremely specific for CDK4 activity. The advantage of targeting p27 tyrosine (Y) phosphorylation as an indirect way to target CDK4 activity is that p27 has few substrates and as such its targeting should be more specific. Additionally, use of Palbociclib has shown that targeting CDK4 is a valid approach. The p27 tyrosine phosphorylation mimetic provides an additional approach for targeting this important kinase, which may have additional benefits.

Figure 24A:
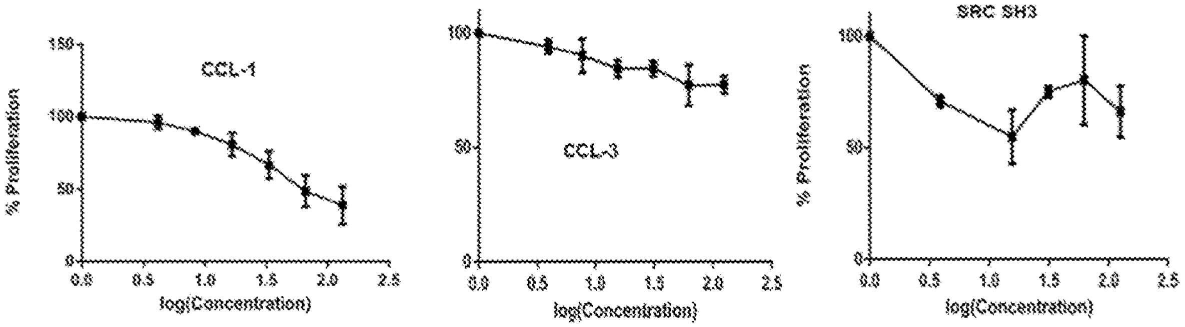
FIGS. 24A-24B.
Figure 24B:
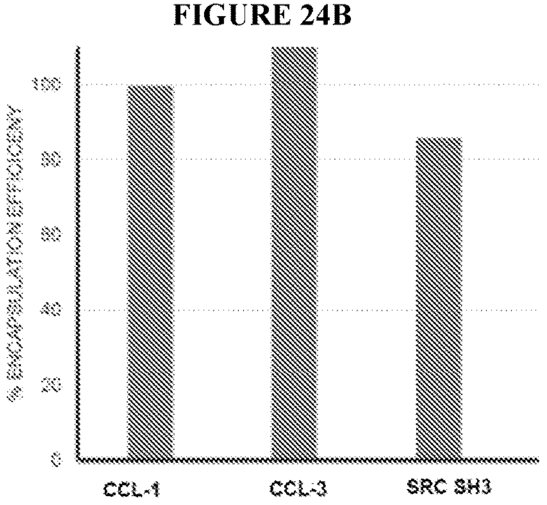

Small molecule mimetics of peptide domains are known in the art. For example, VENCLEXTA™ is a mimetic that functions as a BH3 domain of Bcl2 which inhibits Bcl2 action. In a similar fashion, the present invention provides p27 mimetics. Thus, a peptide of the present invention is a functional mimetic of the K1-containing peptide of p27 or an SH3-containing peptide of Brk having a three-dimensional structure that is similar to that of the native peptide(s), that are capable of inhibiting p27 phosphorylation. The peptide of the present invention also provides advantage over isolated SH3 domain alone as illustrated in FIGS. 24A and 24B. The inhibition of p27 phosphorylation prevents CDK2 and CDK4 activity and therefore prevents cancer cell progression into the cell cycle.

In one aspect, an anti-cancer treatment is further administered to the subject. In one aspect, the anti-cancer treatment is selected from chemotherapy, radiation treatment, immunotherapy and/or resection of a tumor.

The administration of the pharmaceutical composition of the invention can be in combination with one or more additional therapeutic agents. The phrases "combination therapy", "combined with" and the like refer to the use of more than one medication or treatment simultaneously to increase the response. The composition of the present invention might for example be used in combination with other anti-cancer-treatments to treat cancer. Specifically, the administration of the peptide of the present invention to a subject can be in combination with an anti-cancer treatment.

In some aspects, the anti-cancer treatment is administered prior to, simultaneously with, or after the administration of the pharmaceutical composition of the present invention.

In some aspects, the anti-cancer treatment is an anti-cancer agent selected from the group consisting of palbociclib (PB), ribociclib, abemaciclib, osirmetinib, gefitinib, lapatinib, pantitumumab, vandetanib, necitumumab, vemurafenib, sorafenib tosylate, PLX-4720, dabrafenib, paclitaxel, cisplatin, docetaxol, carboplatin, vincristine, vinblastine, methotrexate, cyclophosphamide, CPT-11, 5-fluorouracil, gemcitabine, estramustine, carmustine, adriamycin, etoposide, arsenic trioxide, irinotecan, Herceptin, vemurafenib, erlotinib, cetuximab, letrozole, fulvestrant, and epolhilone derivatives.

Presented below are examples illustrating the generation of truncated BRK peptides and the analysis of their ability to specifically inhibit cancer cell proliferation and survival contemplated for the present invention. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Recombinant Generation of Alt Peptides

Recombinant peptides variants of varying lengths were generated, and their characteristics and effects were compared to the full-length CCL-1 peptide.

Oligonucleotides encoding the PxxP-peptides K1, K2 and K3 were annealed and directly ligated into pGEX-KG expression vector for production of N-terminally GST-tagged peptides. GST, GST-Brk SH3, GST-Brk SH2 expressing plasmids were described. *E. coli* BL21 cells transformed with these plasmids were grown in LB-ampicillin until an OD of 0.6 was reached and protein production was induced by addition of 1 mM IPTG. After 2 hours, cells were harvested by centrifugation. Cell lysis and protein purification on GST-sepharose was carried out according to the GST-protein purification manual (GE Healthcare). Protein was eluted with an excess of glutathione and dialyzed against PBS for further use. Purified, C-terminal histidine-tagged or N-terminal Flag tagged p27's were generated from *E. coli* as described previously. Human p27 cDNA was used as a template in PCR-mutagenesis with oligonucleotides carrying the point mutations: PPPP (SEQ ID NO:42) 91-95 AAAA (SEQ ID NO:43) (ΔK1); PKKP (SEQ ID NO:44) 188-191 AAAA (SEQ ID NO:45) (ΔK3); or PPPP (SEQ ID NO:42) 91-95 AAAA (SEQ ID NO:45) and PKKP (SEQ ID NO:44) 188-191 AAAA (SEQ ID NO:45) (ΔK1/K3).

The PCR fragments were ligated to the T7pGEMEX human His-p27 or T7pGEMEX humanFlag-p27 plasmid for expression in *E. coli*. Mutants Y74F, Y88F, and Y88/89F were previously described. Flag-tagged p27 mutants were purified by Flag-immunoprecipitation with Flag antibody (M-2, Sigma F-18C9) and eluted with Flag peptide (Sigma F-4799) according to manufacturer's protocol. His-tagged p27 mutants were purified by FPLC via his-trap affinity chromatography (His-Trap HP, GE Healthcare 71-5247-01). The affinity column was stripped according to manufacturer's protocol, then washed with 5 column volumes of 100 mM $CoCl_2$. The crude material was applied with a loading buffer consisting of 6 M urea, 500 mM NaCl, 50 mM Tris-HCl, pH 7.5 and 20% glycerol. The material was washed with 500 mM NaCl, 50 mM Tris-HCl, pH 7.5 and 10% glycerol. The purified material was eluted with 500 mM imidazole, 20 mM Hepes pH 7.4 and 1 M KCl. The protein was then dialyzed overnight in a solution of 25 mM Hepes pH 7.7, 150 mM NaCl, 5 mM MgCl2 and 0.05% NP40. All purified proteins were analyzed by Coomassie and immunoblot analysis. The p2'7, ΔK1, ΔK3, ΔK1/K3, Y74F, and Y88/89F cassettes were cloned into the pTRE3G tetracycline inducible retroviral expression construct using the In Fusion Gene Cloning kit (Clontech). Alt Brk was generated by PCR using human Alt-Brk in PCDNA3 vector as a template, followed by cloning into the T7pGEMEXhuman Flag-tagged plasmid and pTRE3G using the In-fusion cloning kit. The amino acid sequence of Alt-Brk is shown below:

```
                                        (SEQ ID NO: 46)
MVSRDQAHLGPKYVGLWDFKSRTDEELSFRAGDVFHVAR

KEEQWWWATLLDEAGGAVAQGYVPHNYLAERETVESEPA

GHAGCAALQDLAACRGPAAPERGGVLPQPARACELPQGP

EPVPRPAAGRALPEARA.
```

Example 2

Synthetic Generation of Alt Peptides

Synthetic peptides may be synthesized by standard methods of solid phase peptide chemistry known to those of ordinary skill in the art. For example, they may be synthesized by solid phase chemistry techniques following procedures previously described using an automated synthesizer. Similarly, multiple fragments may be synthesized then linked together to form larger fragments. These synthetic peptide fragments can also be made with amino acid substitutions at specific locations.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Academic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of ITP fragments. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide DIC) or O-benzotriazol-1-yl-N,N,N',N'-tetramethyluronium-hexafluorophosphate HBTU), with or without 4-dimethylaminopyridine DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours at a temperature of between 10° and 50° C. in a solvent such as dichloromethane or DMF.

When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal acid as described above. The preferred method for coupling to the deprotected 4-(2',4'-dimethoxyphenyl-Fmoc-aminomethyl) phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly-basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Figure 18A:
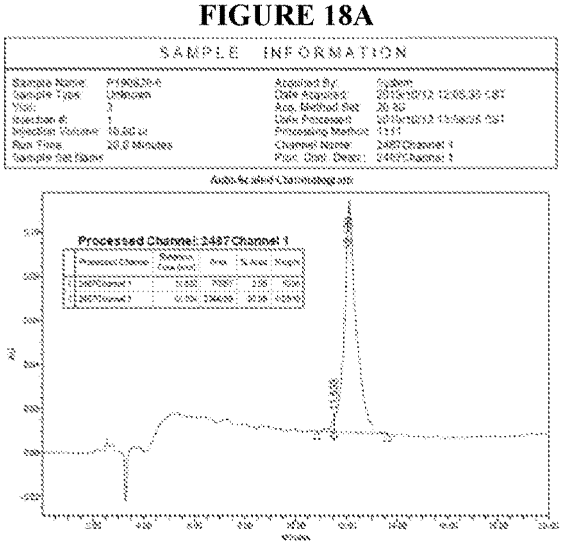
FIGS. 18A-18B illustrate CCL-8 characterization.
Figure 18B:
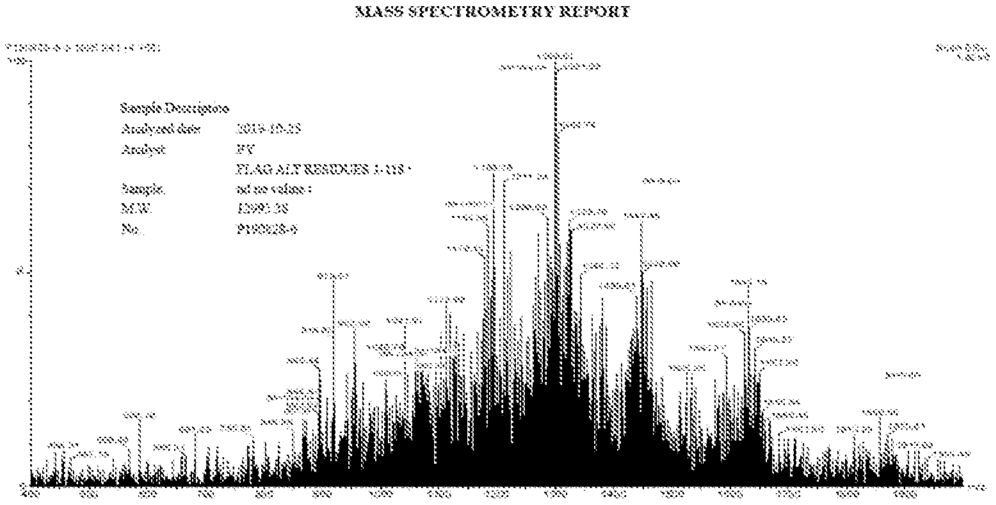

HPLC trace and Molecular weight of CCL-8 peptide was determined using Fast Atom Bombardment (FAB) Mass Spectroscopy or any other Mass Spectroscopic technologies (see FIGS. 18A-18B).

Figure 19A:
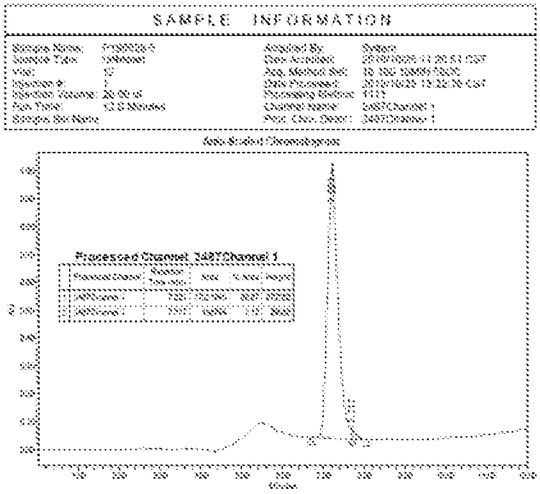
FIGS. 19A-19B illustrate CCL-9 characterization.
Figure 19B:
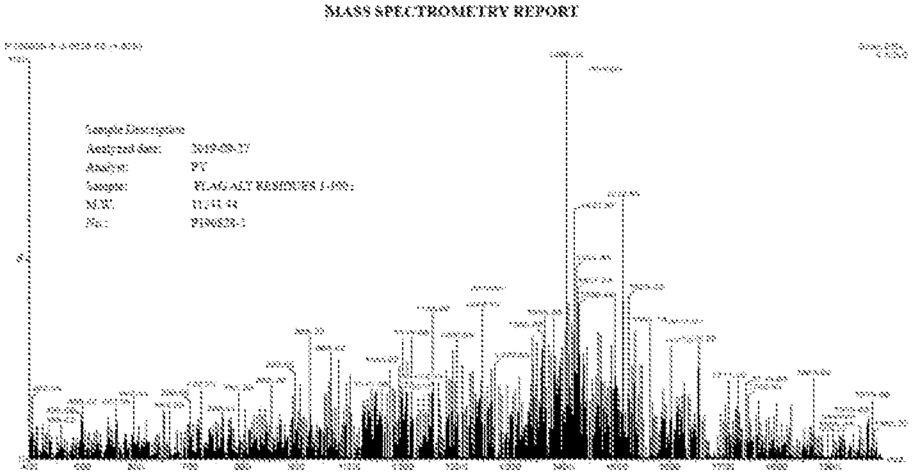

HPLC trace and Molecular weight of CCL-9 peptide was determined using Fast Atom Bombardment (FAB) Mass Spectroscopy or any other Mass Spectroscopic technologies (see FIGS. 19A-19B).

Figure 20A:
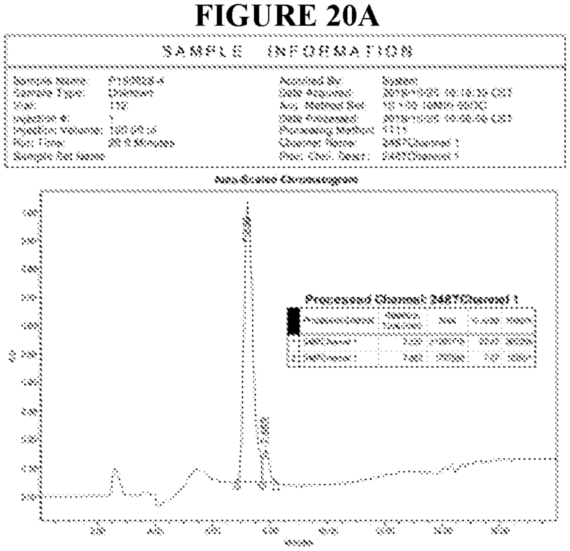
FIGS. 20A-20B illustrate CCL-10 characterization.
Figure 20B:
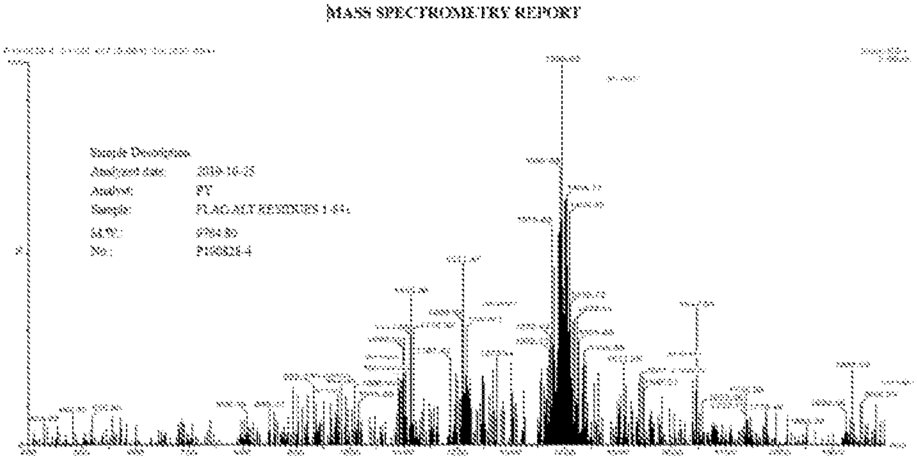

HPLC trace and Molecular weight of CCL-10 peptide was determined using Fast Atom Bombardment (FAB) Mass Spectroscopy or any other Mass Spectroscopic technologies (see FIGS. 20A-20B).

Figure 21A:
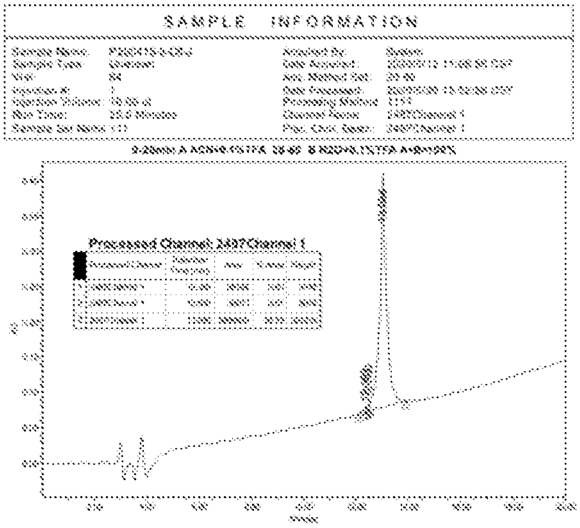
FIGS. 21A-21B illustrate CCL-20 characterization.
Figure 21B:
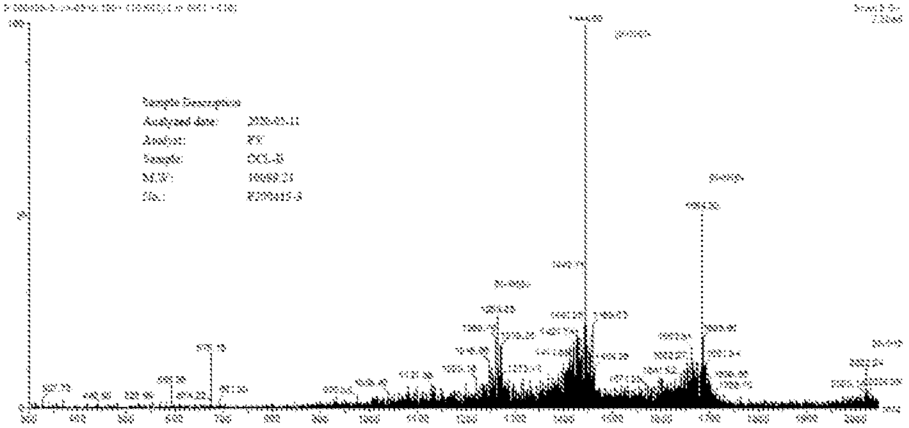

HPLC trace and Molecular weight of CCL-20 peptide was determined using Fast Atom Bombardment (FAB) Mass Spectroscopy or any other Mass Spectroscopic technologies (see FIGS. 21A-21B).

Figure 22:
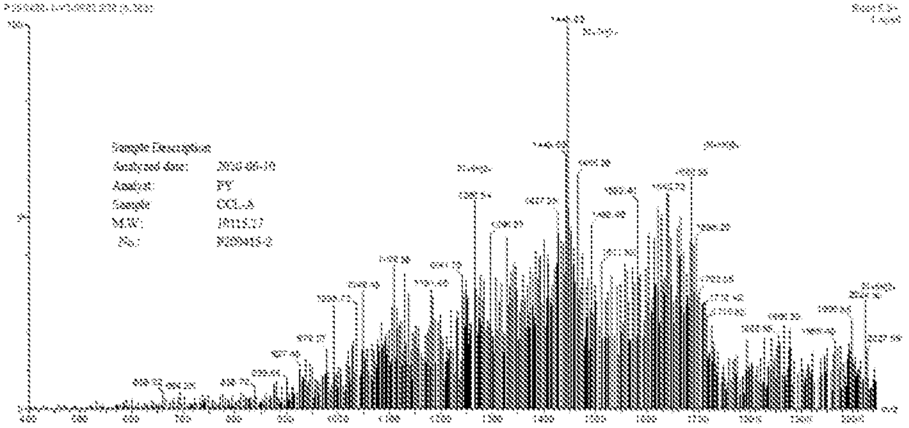
FIG. 22 illustrates CCL-19 MS.

Molecular weight of CCL-19 peptide was determined using Fast Atom Bombardment (FAB) Mass Spectroscopy or any other Mass Spectroscopic technologies (see FIG. 22).

Figure 23:
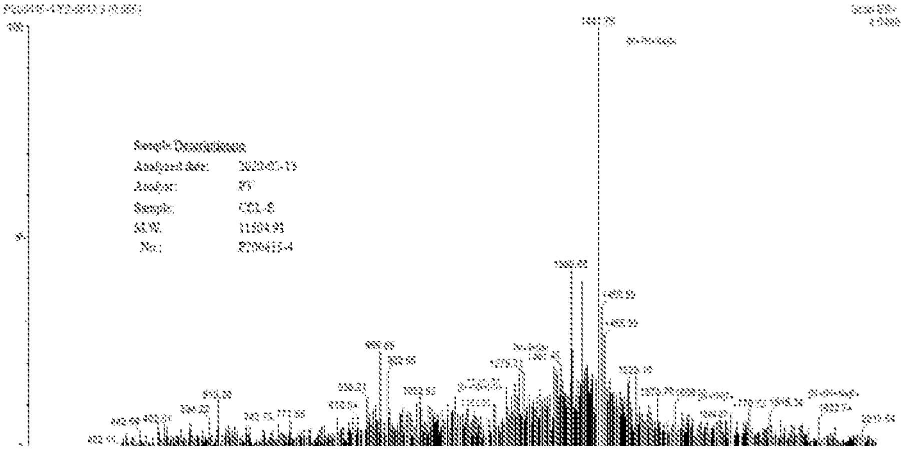
FIG. 23 illustrates CCL-21 MS.

Molecular weight of CCL-21 peptide was determined using Fast Atom Bombardment (FAB) Mass Spectroscopy or any other Mass Spectroscopic technologies (see FIG. 23).

Example 3

Effects of Brk Peptides on Cell Proliferation and Cell Viability

Among the various peptides generated, truncated or mutated in regions and/or amino acids of interest (as illustrated in FIG. 1 and in Table 3), peptides CCL-8-CCL-14 were further investigated for their individual effect in cell proliferation and cell viability in MCF7 cells, a breast cancer cell line.

TABLE 3

| summary of peptides modification | |
|---|---|
| CCL-1 | Flag ALT (no Valine 103) |
| CCL-2 | No Flag ALT (with Valine 103) |
| CCL-3 | Flag ALT SH3 domain no tail |
| CCL-4a | Flag ALT (5A mutant) full length with mutated SH3 domain DEAGG-AAAAA (SEQ ID NO: 47) (no Valine 103) |
| CCL-4b | No Flag ALT (5A mutant) full length with mutated SH3 domain DEAGG-AAAAA (SEQ ID NO: 47) (with Valine 103) |
| CCL-5a | Scrambled Flag ALT (no Valine 103) |
| CCL-5b | Scrambled Flag ALT (with Valine 103) |
| CCL-6 | Flag ALT with Valine at 103 |
| CCL-7 | Flag ALT truncated to 109 (no Valine 103) |
| CCL-8 | Flag ALT truncated to 109 (no Valine 103) |
| CCL-9 | Flag ALT truncated to 91 |
| CCL-10 | Flag ALT truncated to 75 |
| CCL-11 | No Flag ALT from 12-93 |
| CCL-12 | No Flag ALT from 1-93 |
| CCL-13 | No Flag ALT from 12-83 |
| CCL-14 | No Flag ALT from 1-83 |
| CCL-15 | Flag ALT scrambled tail |
| CCL-16 | Flag ALT full length with mutated SH3 domain EE-AA (SEQ ID NO: 48) (no Valine 103) |
| CCL-17 | Flag ALT full length with mutated SH3 domain DEAGG-DEAAA (SEQ ID NO: 49) (no Valine 103) |
| CCL-18 | Flag ALT full length with mutated SH3 domain DEAGG-AAAGG (SEQ ID NO: 50) (no Valine 103) |
| CCL-19 | No Flag ALT truncated to 91 |
| CCL-20 | No Flag ALT truncated to 91 with S |
| CCL-21 | CPP, No Flag ALT truncated to 91 with S |
| CCL-22 | Flag SH3 domain with EE-AA (SEQ ID NO: 48) (no Valine 103) |
| CCL-23 | Flag SH3 domain with DEAGG-DEAAA (SEQ ID NO: 51) (no Valine 103) |
| CCL-24 | Flag SRC SH3 domain with DEAGG (SEQ ID NO: 52) |
| CCL-25 | Flag SH3 domain with DEAGG-AAAGG (SEQ ID NO: 50) (no Valine 103) |
| CCL-26 | Flag SH3 domain with DEAGG-AAAAA (SEQ ID NO: 47) (no Valine 103) |
| CCL-27 | No Flag ALT truncated to 91 with S with mutated SH3 domain DEAGG-AAAAA (SEQ ID NO: 47) |

For proliferation and viability assays, MCF7 cells were seeded on 96 well plates at 500 cells/well 2 days prior to treatment with synthetic peptides of FLAG-ALT. 48 hrs after cell seeding, cells were treated with 100 ul of each assessed drug concentration in culture media. MCF7 cells were treated the same way with flag ALT and ALT-5A dominant negative mutant as internal control. All peptides were prepared in NP1 formulation (see Table 2). Treatment was repeated after 24 hrs. The following day, functional assays were performed as follow:

Viability assay was performed using Promega Cell-Titer Glo cat #G9242 specifications and signal was measured using a luminometer.

Proliferation assay was performed using a SYTO60 assay. Briefly, cells were fixed with 4% PFA for 15 min at RT. After fixing, cells were washed ×2 with TC PBS and incubated with 2 uM solution of SYTO-60 dye (Thermofisher cat #S11342) in PBS for 4 hours, RT, in the dark. Following dye incubation, cells were washed with PBS, imaged and quantified using Licor reader.

As illustrated in FIGS. 2A-2B and 3A-3B, by comparing the efficacy of peptides CCL-8-CCL-11 compared to Flag-ALT, it was found that CCL-9 induced the strongest inhibition of cell proliferation and cell viability, in a dose dependent manner.

This was further confirmed by comparing the efficacy of peptides CCL-8-10 and CCL-14 compared to Flag-ALT; CCL-8-10 compared to Flag-ALT; CCL-12-14 and CCL-9 compared to Flag-ALT; and CCL-9 and CCL-14 compared to Flag-ALT, as shown respectively in FIGS. 4A-4B and 5A-5B, FIGS. 6A-6B and 7A-7B, FIGS. 8A-8B and 9A-9B, and FIGS. 10A-10B and 11A-11B.

The amount of peptide in the cells after the treatment was evaluated using Eliza methodology. Briefly, MCF7 cells were cultured in DMEM media containing 10% FBS, 1% P/S, insulin and NEEA. For all experiments MCF7 cells were used from passage 3-6. MCF10 cells were always passage 1 and cultured in MEGM media containing fibroblast proliferation kit (Lonza cat #CC-3150) and 10 ng/ml cholera toxin (Sigma cat #C8052). Cells were cultured in 6 well plates prior to harvesting. Cells were treated 2×24 hrs with Flag-ALT or peptide of interest with designated concentrations. After treatment, cells were trypsinized, spun down at 1500 rpm and cell pellet collected. For cell lysis, cells were lysed in activated RIPA lysis buffer containing phosphatase inhibitor II, Iii (Sigma), protease inhibitor V (Sigma) 1 uM DTT, 50 uM NaV, and 1×PMSF. Cell pellet was resuspended in 500 ul activated RIPA lysis buffer and lysed for 20 min on ice. Supernatant was isolated after 5 min spin at 13,000 rpm, 4 C.

The Flag Eliza was performed according to the protocol provided in the Eliza kit by Biovisions (Cat #E4700). Each sample was processed in duplicate, 100 ul each. Assay was performed according to manufacturer instruction and signal read using a plate reader. Flag protein concentrations for each reading were extrapolated from a generated standard curve using provided FLAG protein standards.

As illustrated in FIGS. 12A-12D, in MCF7 cells, larger amounts of CCL-9 were detected in the cells as compared to CCL-8 and CCL-10, suggesting a superior cell permeability of the peptide. Further, CCL-9 was found more potent to inhibit proliferation and viability, with higher inhibition rates than CCL-8 and CCL-10, even with lower amount of peptide.

Example 4

Effects of BRK Peptides on Cell Proliferation and Cell Viability in MCF10A Cells Among the various peptides generated, truncated or mutated in regions and/or amino acids or interest (as illustrated in FIG. 1), peptides CCL-8-CCL-10 and CCL-14 were further investigated for their individual effect in cell proliferation and cell viability in MCF10A cells, a non-carcinogenic breast cell line.

The cells were cultured and prepared for the assays as described in Example 2.

As illustrated in FIGS. 13A-13B and 14A-14B, comparing the efficacy of peptides CCL-8-CCL-10 and CCL-14 compared to Flag-ALT, it was found that CCL-9 induced the strongest inhibition of cell proliferation and cell viability, in a dose dependent manner. However, the comparison of the cell proliferation and cell viability rates obtained in MCF7 and MCF10A demonstrated that the peptide greatly inhibits cell proliferation and cell viability of cancer cell (e.g., MCF7), but impacts cell proliferation and cell viability of non-carcinogenic cells (e.g., MCF10A) to a much lesser extend (see FIGS. 4 and 5, as compared to FIGS. 13 and 14).

Example 5

Comparison of BRK Peptides Effects in MCF7 and MCF10A Cells

The effects of CCL-9 on cell proliferation and cell viability were compared to those induced by CCL-14 in MCF7 and MCF10A cells. The cells were cultured and prepared for the assays as described in Example 2.

As illustrated in FIGS. 15A-15B and 16A-16B, CCL-9 and CCL-14 were found more potent to inhibit cell proliferation and viability in the carcinogenic MCF7 cells as compared to the non-carcinogenic MCF10A cells.

Further, the amounts of CCL-8-CCL-10 detected in cells were compared in MCF7 and MCF10A cells. The cells were cultured and prepared for the assays as described in Example 2.

As illustrated in FIGS. 17A-17F, it was found that peptide uptake was increased in MCF7 cells as compared to MCF10A cells, regardless of the quantity of peptide used to treat the cells.

After evaluation of proliferation and viability in MCF7 and MCF10A cells, it was found that CCL-9 was the best candidate in terms of stability and mirroring full length CCL-1 response. A slightly longer variant was generated in the recombinant setting (CCL-7), but it was unsuccessful; the peptide was unstable and rapidly degraded to smaller variants. CCL-9 encompasses the SH3 domain, and a putative alpha helix immediately downstream of the VESEP domain.

Example 6

Effects of BRK PEPTIDES on Breast Cancer Cells In Vitro

To establish whether the function of shorter variants remains the same as the full length IpY.2/1x (CCL-2/NPx) the efficacy of CCL-19/NPx (IpY.19/1x) and CCL-20/NPx (IpY.20/1x) was assessed in vitro.

The large 140 aa CCL-2 peptide was truncated to 91 aa variants, called CCL-19 and CCL-20. These two synthetic peptides differ in the presence of a single C to S substitution in the C terminus, which potentially increases the stability of CCL-20. The aim of this study was to investigate whether liposome packaged CCL-19 and CCL-20, IpY.19 and IpY.20, recapitulate all of the features of IpY and the full-length CCL-2 peptide in both multiple breast cancer lines and in normal breast mammary cells.

The study was performed on:

(1) ER/PR positive breast cancer line: MCF7 and T47D (2) Triple negative breast cancer line: BT-549

(3) Normal breast cell line: MCF10A

To examine the efficacy of CCL-19/NPx (IpY.19/1x) and CCL-20/NPx (IpY.20/1x) in each cell line, cell viability assay (MTT) was performed:

(1) Cell viability assay (MTT) driven by quantification of ATP in cells to determine the growth inhibitory effect of our peptides.

In each experiment, the results were compared to the already established efficacy of IpY.2/1x (CCL-2/NPx) as well as to CCL-27/NPx (IpY.27/1x), a dominant negative variant of the therapeutic peptide that was utilized as a negative control.

Cells were cultured in MEM media (Fisher Scientific, SH30024FS) or RPMI media (Fisher Scientific, SH30027FS) supplemented with Fetal Bovine Serum (FBS) (Fisher Scientific, Cat No. 35016CV), HyClone Non Essential Amino Acids, 100× Solution (Fisher Scientific, Cat No. SH3023801), HyClone Amphotericin B (Fungizone) Solution (Fisher Scientific, Cat No. SV3007801), Gibco Penicillin-Streptomycin (10,000 U/ml) (Fisher Scientific, Cat No. 15140122), Insulin solution from bovine pancreas (Sigma Aldrich, Cat No. 10516), PEN/STREP/GLUTAMINE (Fisher Scientific, SV3008201). For cell preparation, Gibco Trypsin-EDTA (0.25%), phenol red (Fisher Scientific, Cat No. 25200072), Gibco PBS, 10× (Fisher, Cat No. 70011044), and Trypsin (Fisher Scientific, 25 200 072) were used.

For ATP viability assay, cells were plated in 96 well plates at 500 cells/well and allowed to attach for 24 hrs. After 24 hr, dose response treatment was performed of peptides in liposomes. Treatment was performed for 48 hrs total, replenished once in 24 hrs. Cell viability was assessed using Promega CellTiter Glow viability assay according to the manufacturer instructions.

Figure 25A:
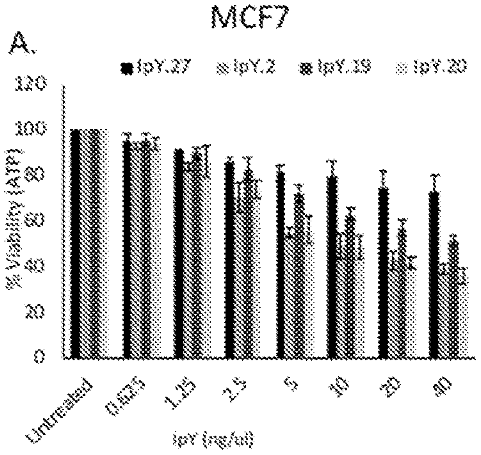
FIGS. 25A-25B show the functional comparison between CCL-2 and CCL-19 and CCL-20 and illustrate ATP viability measured after dose response treatment with peptides in nanoparticles.
Figure 25B:
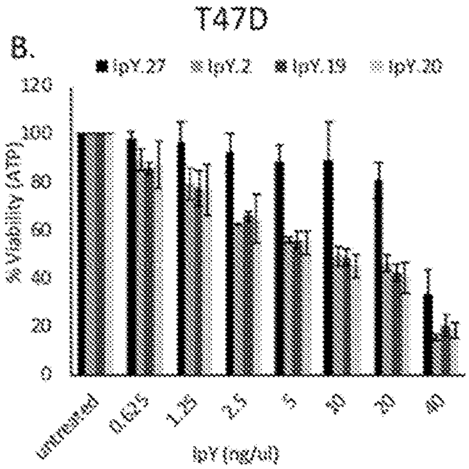

As illustrated in FIGS. 25A-25B, the efficacy of IpY.19/1x and IpY.20/1x was assessed in ER/PR breast cancer cell lines. Treatment with IpY.2/1x, IpY.19/1x and IpY.20/1x caused significant reduction in cell viability compared to IpY.27/1x, the negative control. There was not statistically significant difference between the three therapeutic peptides in liposomes IpY.2/1x, IpY.19/1x and IpY.20/1x indicating that shorter peptide variants CCL-19 and CCL-20 has the same efficacy as the full-length CCL-2.

Figure 26:
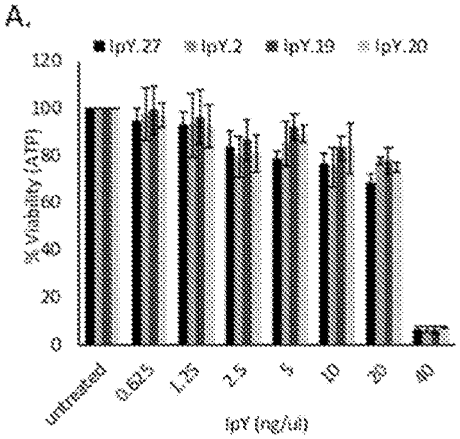
FIG. 26 shows the functional comparison between CCL-2 and CCL-19 and CCL-20 and illustrate ATP viability measured in BT-549 cells. N=3.

As illustrated in FIG. 26, the efficacy of IpY.19/1x and IpY.20/1x was then assessed in Triple negative breast cancer cell line. While IpY.2/1x has some effect in triple negative lines, its efficacy to reduce ATP driven cell viability is weaker compared to the effect observed in ER positive cells. Dose response treatment with IpY.19/1x and IpY.20/1x caused a moderate reduction in cell viability, indistinguishable from IpY.2/1x. This result indicates that the shorter peptide variants CCL-19 and CCL-20 function in the same way as the full-length CCL-2 in BT-549 triple negative lines.

Figure 27:
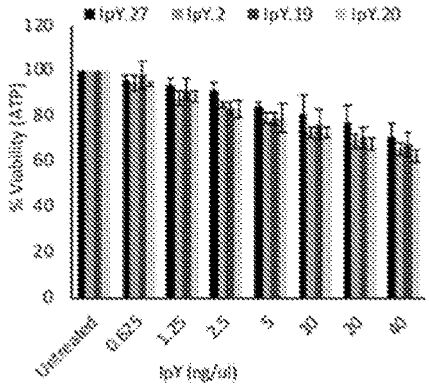
FIG. 27 shows the functional comparison between CCL-2 and CCL-19 and CCL-20 and illustrate ATP viability measured in MCF10A cells. N=3.
Figure 28A:
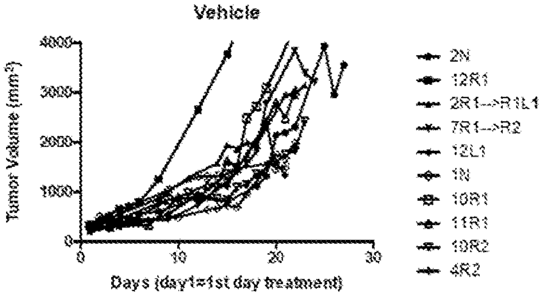
FIGS. 28A-28E illustrate tumor volume over time in NOS/SCID female mice injected with $5\times10^{6}$ MCF7 cells and treated with vehicle, CCL-2, CCL-19 or CCL-20. FIG.
Figure 28B:
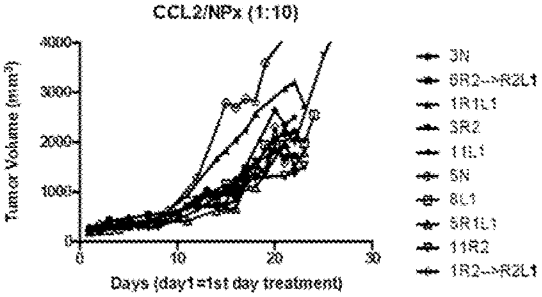
Figure 28C:
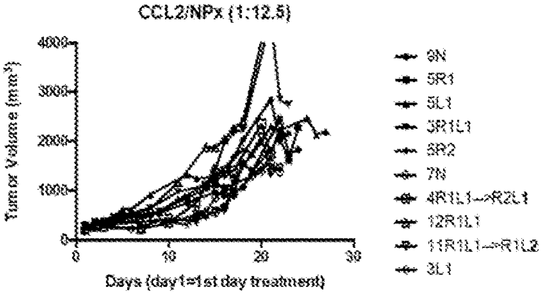
Figure 28D:
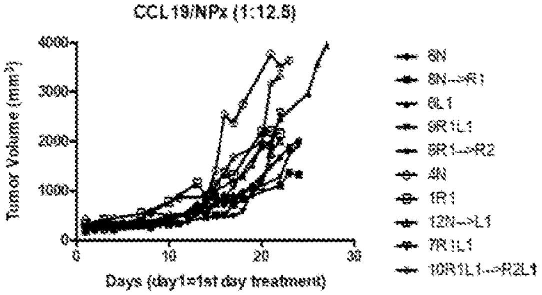
Figure 28E:
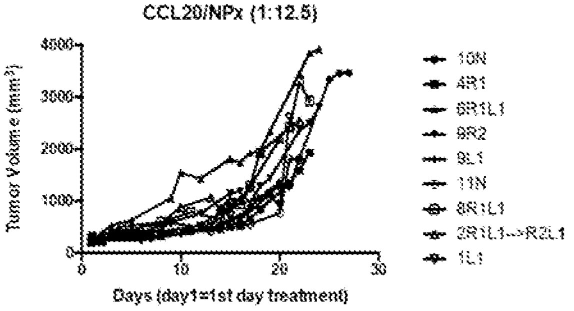

As illustrated in FIG. 27 the efficacy of IpY.19/1x and IpY.20/1x was assessed in normal mammary breast cell line. The full-length peptide CCL-2 has low efficacy in normal breast cell line MCF10A, potentially indicating that the therapy may not target normal cells as efficiently as tumor cells. It was thus critical to establish if shorter peptide variants, CCL-19 and CCL-20 possessed the same therapeutic characteristics. Treatment with IpY.19/1x and IpY.20/1x caused a weak reduction in cell viability, indistinguishable from IpY.2/1x in MCF10A recapitulating the low efficacy previously observed with the full-length CCL-2.

As summarized in Table 4, this study showed that treatment with IpY.19/1x (CCL-19/NPx) and IpY.20/1x (CCL-20/NPx) resulted in reduction in ATP driven cell viability that is indistinguishable from IpY.2/1x (CCL-2/NPx) in ER positive MCF7 and T47D lines; that treatment with IpY.19/1x (CCL-19/NPx) and IpY.20/1x (CCL-20/NPx) in triple negative BT-549 cell line did not induce robust decrease in cell viability (these results were comparable with those recorded after BT-549 cells were treated with IpY.2/1x (CCL-2/NPx)); and that IpY.19/1x (CCL-19/NPx) and IpY.20/1x (CCL-20/NPx) function similarly to IpY.2/1x (CCL-2/NPx) in MCF10 cells where treatment causes minimal reduction in cell viability.

TABLE 4

$IC_{50}$ values established based on ATP viability assay averages

| $IC_{50}$ (ng/ul) | CCL-2 | CCL-19 | CCL-20 |
|---|---|---|---|
| MCF7 | 5.55 | 5.61 | 5.48 |
| T47D | 7.45 | 6.20 | 6.42 |
| BT-549 | >40 | >40 | >40 |
| MCF10A | >40 | >40 | >40 |

MCF7 n = 4;
T47F n = 3;
BT-549 n = 3;
MCF10A n = 2

It has been demonstrated that both IpY.19 and IpY.20 exhibit the same efficiency and function in the same way as IpY.2 in MCF10A normal cells, triple negative BT-549 cells and ER positive breast cancer lines, and it was also established that there was no difference in activity between IpY.19 and IpY.20 in all examined cell lines, indicating that converting the cysteine residue to serine residue on IpY.20 does not affect its function.

Keeping the cysteine residue on CCL-19 allowed to fluorescently label CCL-19 via maleimide-cysteine coupling reaction. CCL-19 was labeled with IRDye680RD and will use the fluorescently label CCL-19 as a surrogate for CCL-20 to study the half-life of our therapeutic peptide as well as perform extended time course study to assess the dosing frequency of CCL-20 in vitro.

Example 7

Effects of BRK Peptides on Tumor Growth of MCF7 Cells In Vivo

The effects of BRK peptides were evaluated on the growth of MCF7 cells injected in vivo in mice.

Estrogen pellets were implanted into 5-6-week-old NOD/SCID female mice. One week later, $5\times10^6$ MCF7 cells were injected subcutaneously on the right flank, near 4th mammary gland fat pad of each animal. Tumor growth was monitored daily, and tumor volume was measured with digital caliper. Mice were randomly assigned to treatment groups once tumor volume reached 200-300 $mm^3$. Mice were separated in 5 treatment groups, and received daily intravenous injection of vehicle (PBS/HEPES), CCL-2/NPx (at a 1:10 ratio of peptide:lipid), CCL-2/NPx (1:12.5), CCL-19/NPx (1:12.5), or CCL-20/NPx (1:12.5).

Figure 29A:
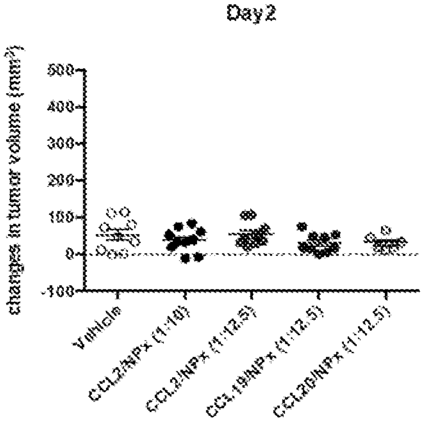
FIGS. 29A-29T illustrate change in tumor volume over time in NOS/SCID female mice injected with $5\times10^6$ MCF7 cells and treated with vehicle, CCL-2, CCL-19 or CCL-20.
Figure 29B:
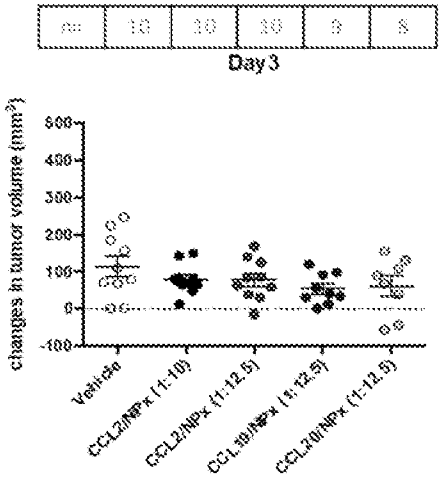
FIG. 29B illustrates change in tumor volume at day 3.
Figure 29C:
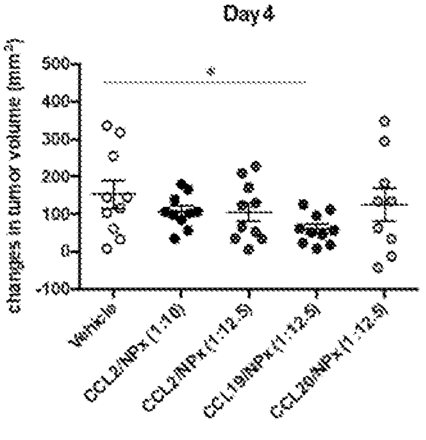
FIG. 29C illustrates change in tumor volume at day 4.
Figure 29D:
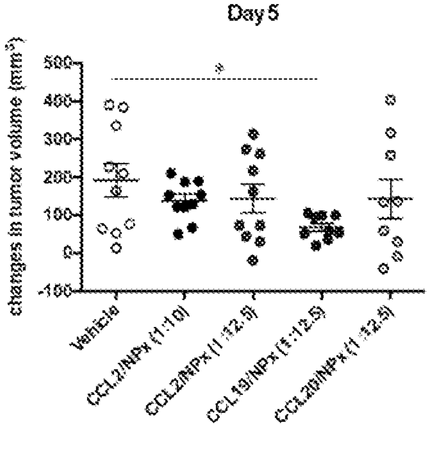
FIG. 29D illustrates change in tumor volume at day 5.
Figure 29E:
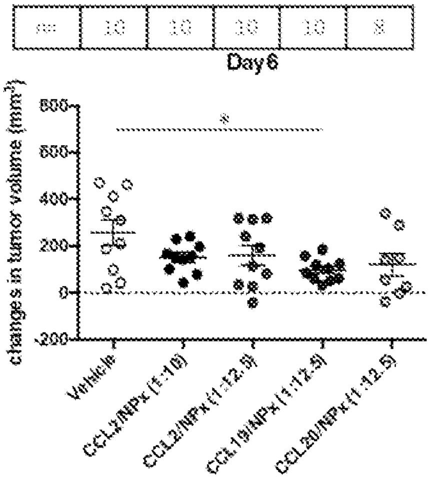
FIG. 29E illustrates change in tumor volume at day 6.
Figure 29F:
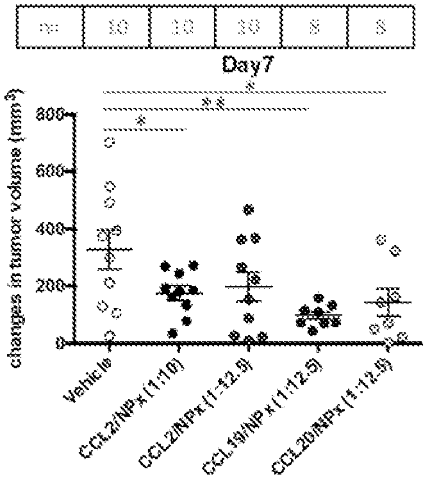
FIG. 29F illustrates change in tumor volume at day 7.
Figure 29G:
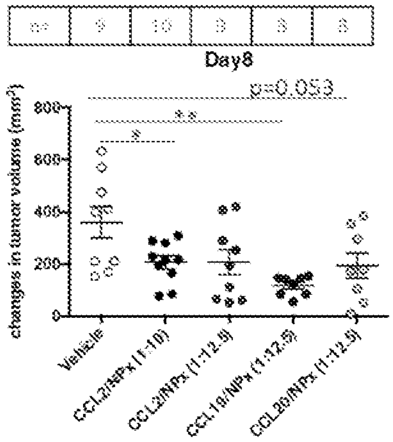
FIG. 29G illustrates change in tumor volume at day 8.
Figure 29H:
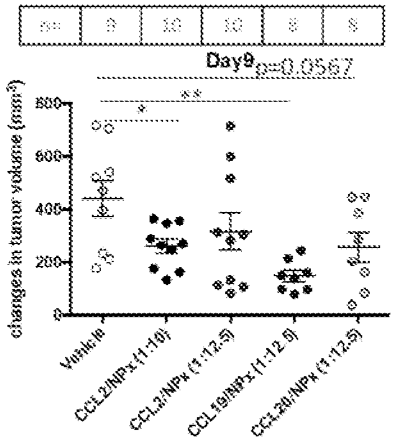
FIG. 29H illustrates change in tumor volume at day 9.
Figure 29I:
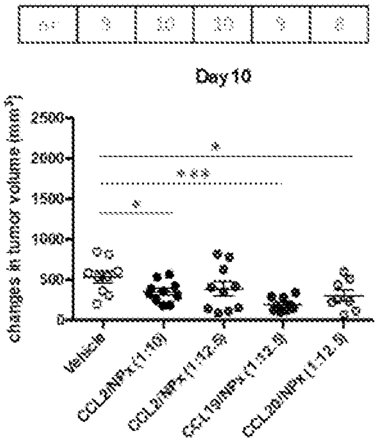
FIG. 29I illustrates change in tumor volume at day 10.
Figure 29J:
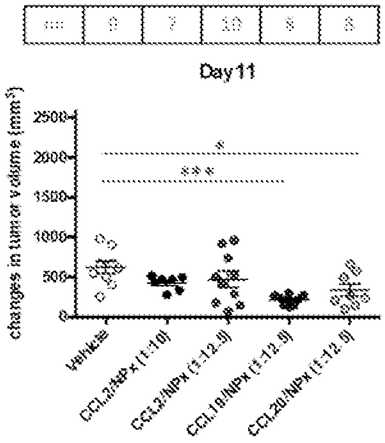
FIG. 29J illustrates change in tumor volume at day 11.
Figure 29K:
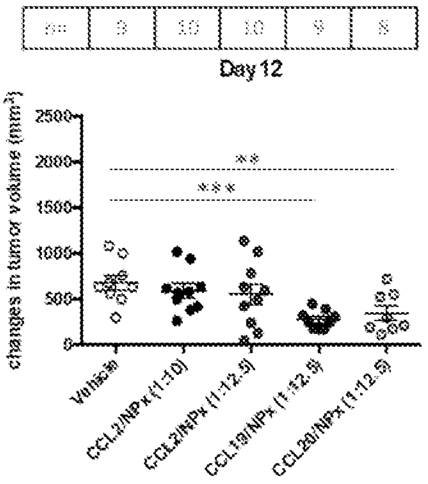
FIG. 29K illustrates change in tumor volume at day 12.
Figure 29L:
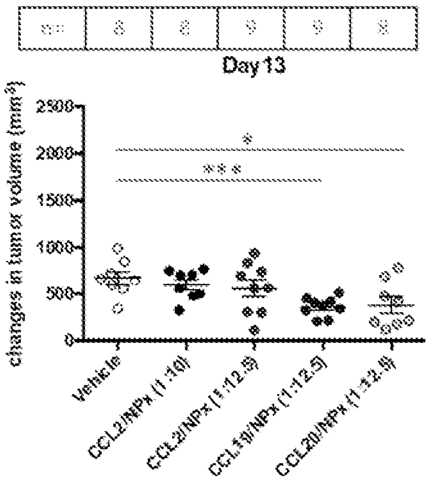
FIG. 29L illustrates change in tumor volume at day 13.
Figure 29M:
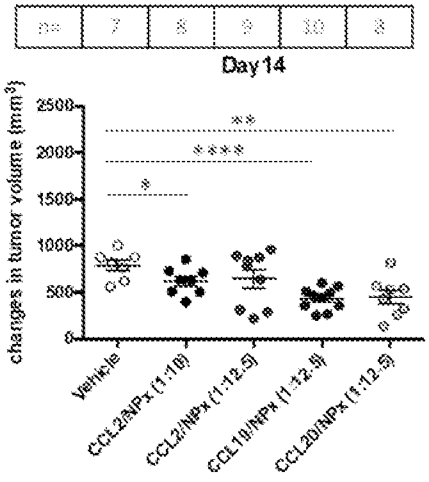
FIG. 29M illustrates change in tumor volume at day 14.
Figure 29N:
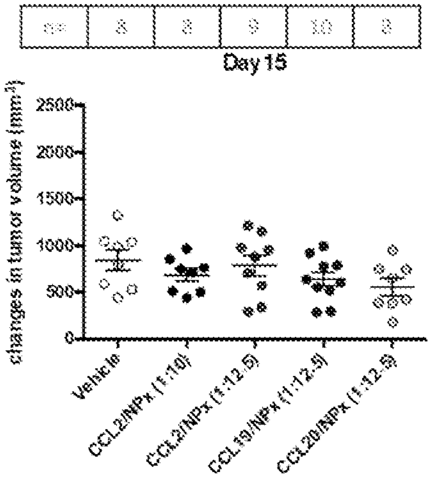
FIG. 29N illustrates change in tumor volume at day 15.
Figure 29O:
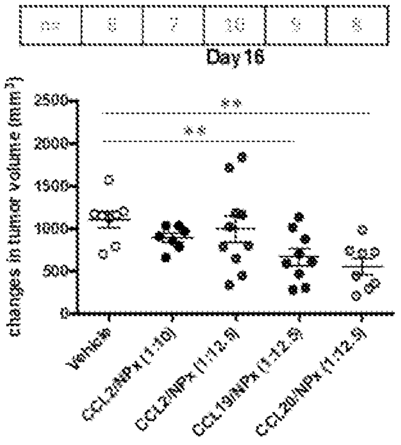
FIG. 29O illustrates change in tumor volume at day 16.
Figure 29P:
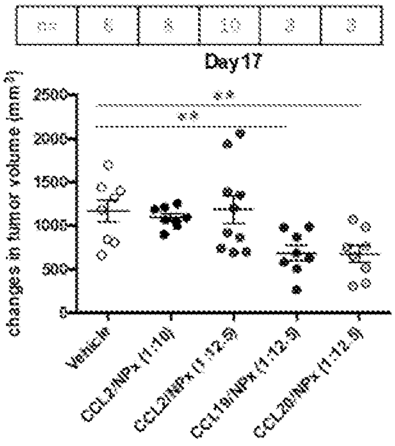
FIG. 29P illustrates change in tumor volume at day 17.
Figure 29Q:
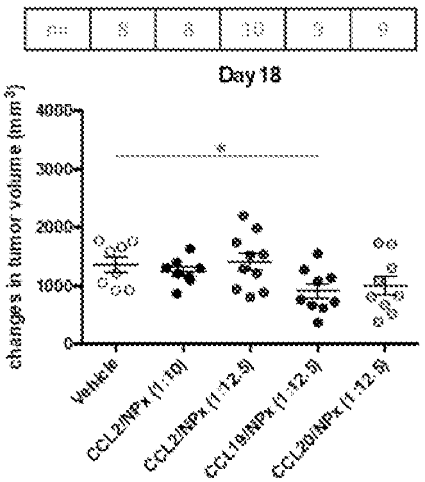
FIG. 29Q illustrates change in tumor volume at day 18.
Figure 29R:
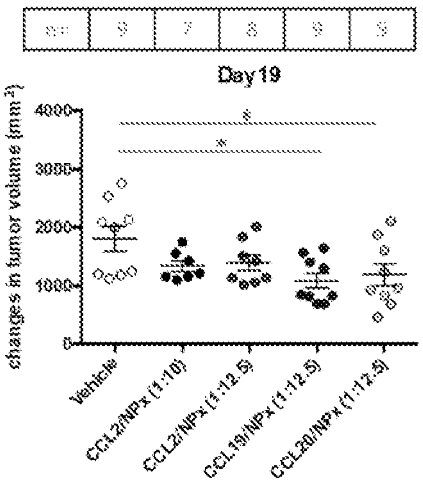
FIG. 29R illustrates change in tumor volume at day 19.

As illustrated in FIGS. 28A-28E, tumor volumes were measured every day. As shown in FIGS. 29A-29T, treatment of the mice with CCL-19/NPx (1:12.5) significantly reduced tumor volume as compared to the vehicle as early as day 4

Figure 29S:
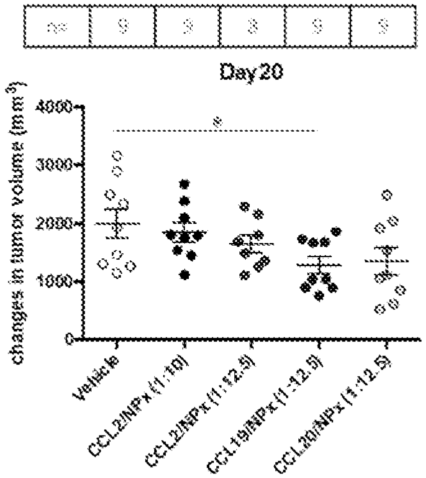
FIG. 29S illustrates change in tumor volume at day 20.
Figure 29T:
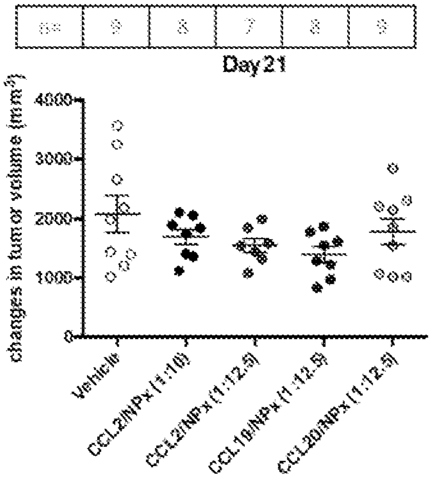
Figure 30A:
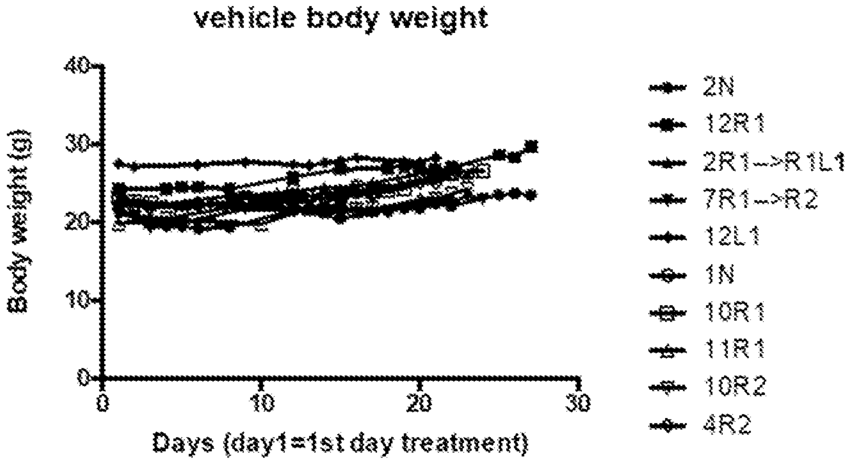
FIGS. 30A-30E illustrate changes in body weight of the animals over the treatment period.
Figure 30B:
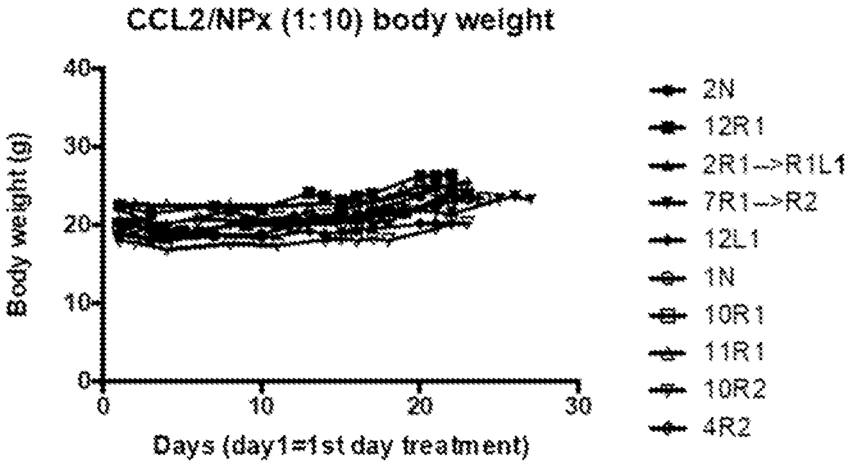
Figure 30C:
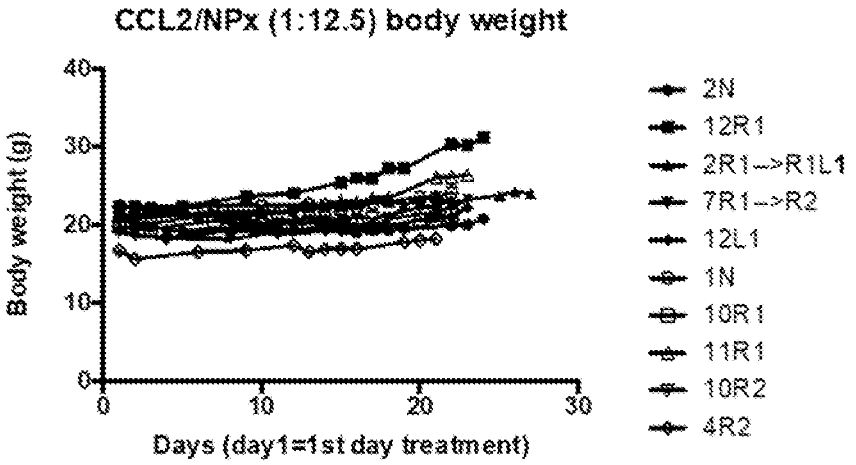
Figure 30D:
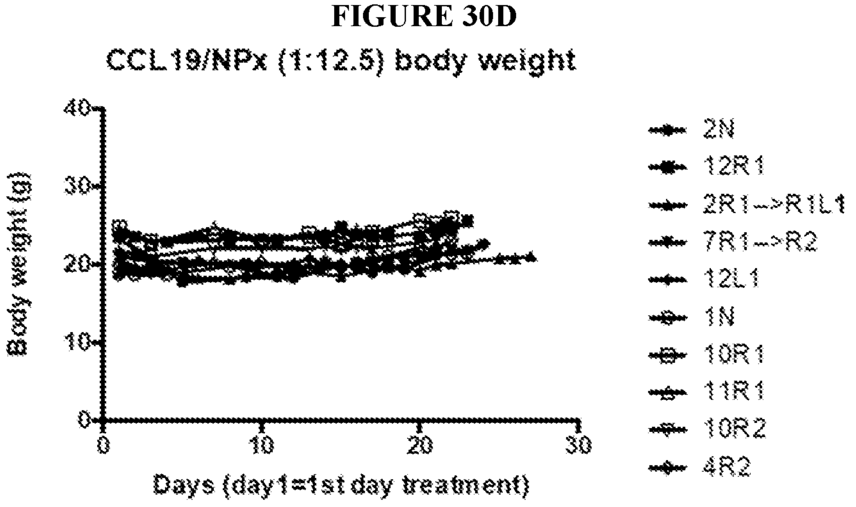
Figure 30E:
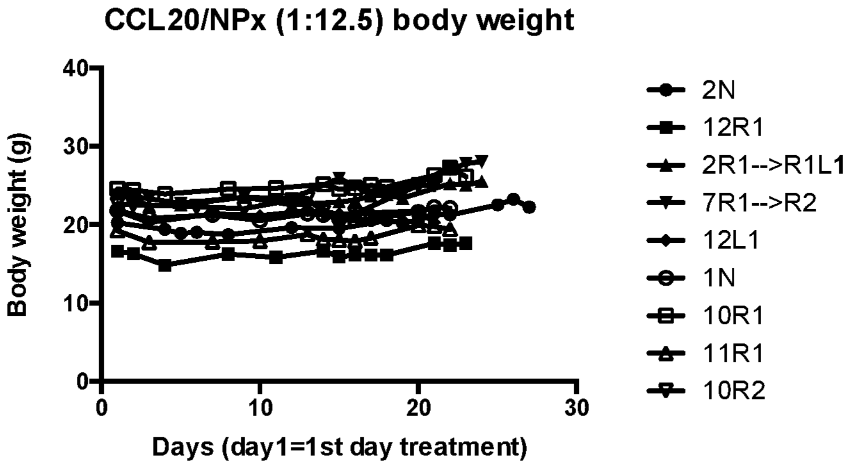

(see FIG. 29C), and the peptide remained significantly efficient at reducing tumor volume until day 20 (see FIG. 29S).

Treatment of the mice with CCL-20/NPx (1:12.5) also significantly reduced tumor volume as compared to the vehicle, starting at day 7 (see FIG. 29F), and remained significantly efficient at reducing tumor volume until day 19 (see FIG. 29R).

As illustrated in FIGS. 30A-30E, there was no significant toxicity associated with the treatment of the animals with the BRK peptides, which can be observed by the absence of change in the weight of the animals over the course of the treatment.

Example 8

Bioengineering of Peptides to Target Breast Cancer Cells

The 144 aa CCL-1 peptide was bioengineered into a 91 aa variant (CCL-20) in order to facilitate manufacturing of the product, IpY.20 (see Table 5)

TABLE 5

IpY versions used in this study

| Peptide | Size (aa) | tag | Name | Notes |
|---|---|---|---|---|
| CCL-1 | 144 | FLAG | IpY.1 | Same as ALT |
| CCL-2 | 144 | None | IpY.2 | Same as ALT |
| CCL-4A | 144 | FLAG | IpY.4a | Inactive with binding mutation |
| CCl-20 | 91 | None | IpY.20 | Therapeutic peptide |
| CCL-19 | 91 | None | IpY.19 | Variant that can be labeled |
| CCL-27 | 91 | None | IpY.27 | Inactive with binding mutation |

Generation of a Truncated Synthetic Peptide, CCL-20.

Figure 31A:
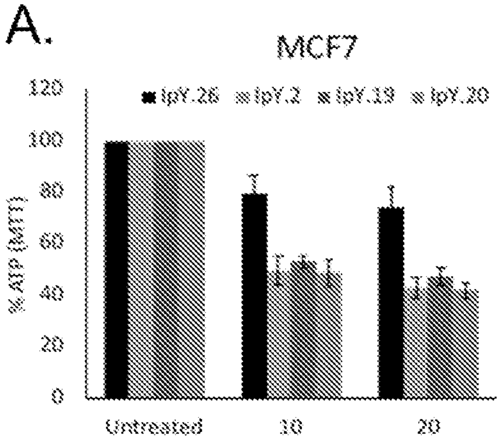
FIGS. 31A-31C illustrate the efficacy of peptides CCL-2, CCL-19 and CCL-20 in breast cancer cells, in vitro and in vivo.
Figure 31B:
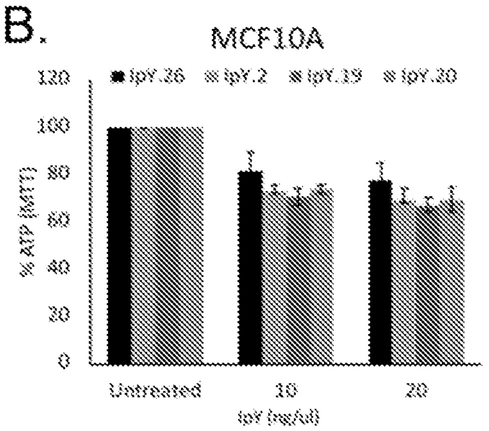

CCL-20 peptide containing additional modifications to residues required to increase the stability of the product during manufacturing was generated by solid phase peptide synthesis, and by HPLC analysis, it was >90% pure. The LNP portion was mixed at a lipid to protein mass ratio of 12.5:1. An additional variant was generated, CCL-19 which contains a single C residue substitution, to permit us to fluorescently label CCL-19 via a maleimide-cysteine coupling reaction. CCL-19 was labeled with IRDye680RD to generate IpY.19-IRD680 as a surrogate for CCL-20 to study the half-life and in vivo delivery of the therapeutic peptide. When CCL-19 and CCL-20 were packaged in the liposome to generate IpY.19 and IpY.20, they recapitulate all of the features of the parent IpY.2 and the full-length CCL-2 peptide in vitro (see FIGS. 31A and 31B). IpY.20 induced cell death in MCF7 and T47D cells and had no efficacy in MCF10A cells (FIG. 31B). IpY.19-IRD680 is indistinguishable from IpY.20 in terms of its ability to reduce viability and induce ROS.

Size/Charge/Stability.

Measurement of size, size distribution and surface charge (zeta potential) were performed using the Zetasizer Nano ZS (Malvern, Inc). The mean±SD of three independently prepared batches is reported. The positively charged particle of a size <200 nm facilitates uptake into tumors via EPR. This size allows sterilization via filtration during the manufacturing process.

TABLE 6

| name | peptide | liposome | Mass ratio (peptide:liposome) | Size (nm) | Zeta potential (mV) | PDI |
|---|---|---|---|---|---|---|
| IpY.19/1x | CCL-19 | NPx | 1:12.5 | 188.83 ± 4.58 | 28.3 ± 0.20 | 0.22 ± 0.05 |
| IpY.20/1x | CCL-20 | NPx | 1:12.5 | 166.10 ± 7.05 | 28.03 ± 1.14 | 0.16 ± 0.02 |
| IpY.19-IRD680/1x | IrDye680RD-CCL-19 | NPx | 1:12.5 | 112.89 ± 2.73 | 36.32 ± 2.05 | 0.15 ± 0.009 |

Example 9

Evaluation of Bioengineered Peptides Biodistribution

Using a labeled variant of IpY.20, it was demonstrated that 10% of the fluorescence detected in the animals was localized to tumors within 15 minutes and the half-life was >24 h.

Figure 32:
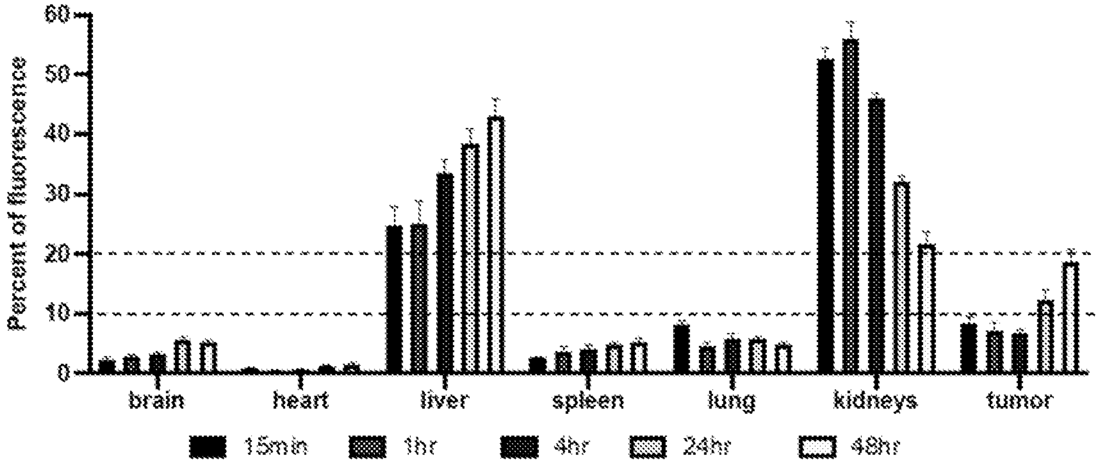
FIG. 32 is a bar graph illustrating the biodistribution of a fluorescently labeled CCL-19 peptide 4 hours after its administration.

Biodistribution with IpY.19 The single cysteine residue on CCL-19 enabled the labeling of CCL-19 with NIR fluorescent dye (IRDye680RD) to generate IpY.19-IRD680, which was demonstrated to behave like IpY.20 in vitro and as such serves as a surrogate for IpY.20. Tumor bearing mice were injected with a single dose of IpY.19-IRD680 and sacrificed at various timepoints. Tumor and organs (brain, heart, liver, spleen, lungs and kidneys) were harvested for IVIS imaging. At all timepoints, both liver and kidneys showed high fluorescent signals, consistent with LNP clearance (FIG. 32). IpY.19-IRD680 reached tumor as early as 15 min. post injection and accumulated at tumor for up to 48 hr post injection. Approximately 10% of the total fluorescent signal was allocated to tumor site at 15 min, 1 hr, 4 hr and 24 hr post injection, by 48 hr post injection, approximately 20% of the total remaining fluorescent signal was allocated to tumor site and less than 10% were found in brain, heart, spleen and lung. Interestingly, IpY.19-IRD680 also reached the brain and accumulated up to 48 hr post injection, suggesting that IpY.19-IRD680 can pass the blood-brain barrier (FIG. 32). To examine elimination half-life of IpY.19-IRD680, plasma was harvested at each time point as well and fluorescence was analyzed using the Odyssey Licor machine. The half-life of IpY.19-IRD680 in plasma was 10.5 hr.

Example 10

Evaluation of Bioengineered Peptides Pharmacodynamics

By analyzing markers of pharmacodynamic (PD) engagement it was demonstrated that IpY.20 inhibited its targets within 24 h. of treatment.

PD markers with CCL-19.

Figure 33A:
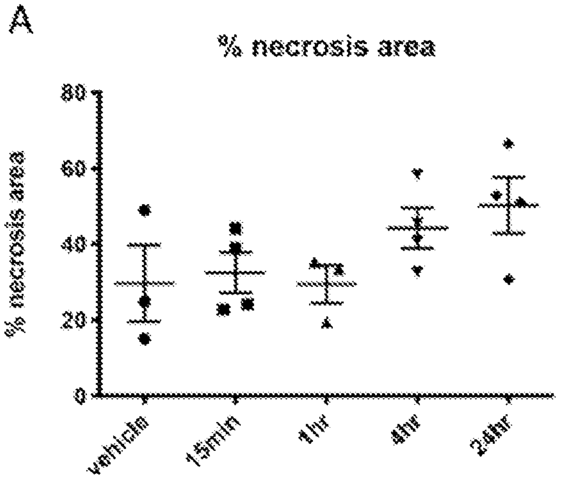
FIGS. 33A-33D illustrate the analysis of pharmacodynamic parameters in tumors following the administration of the CCL-19 peptide, and as compared to the vehicle.
Figure 33B:
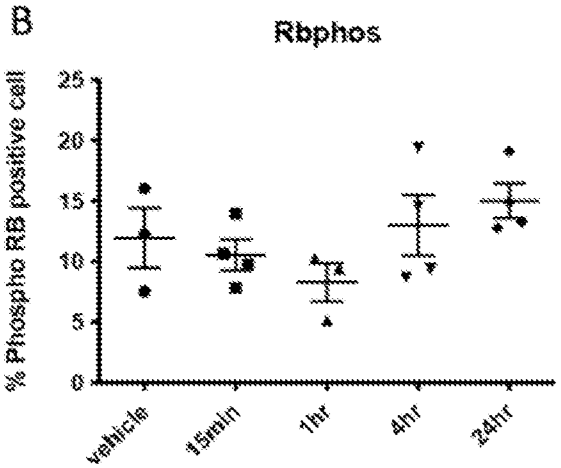
Figure 33C:
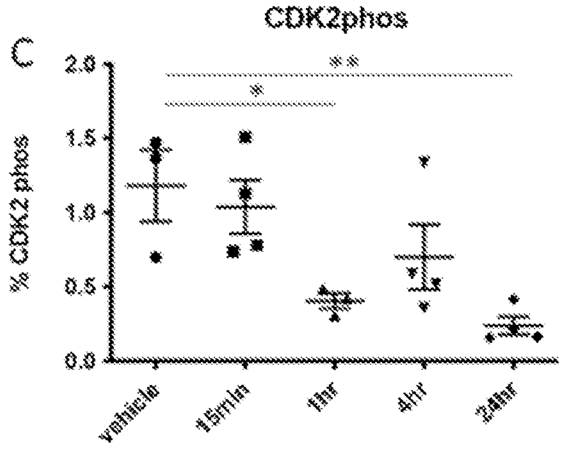
Figure 33D:
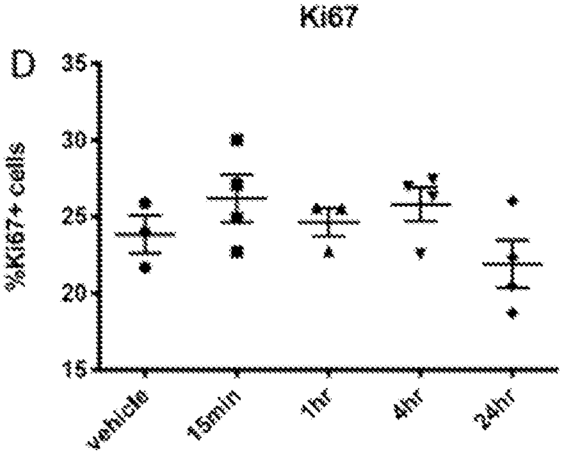

In order to monitor target engagement, several pharmacodynamic assays were developed, which can be used on tumor FFPE material. From the biodistribution experiments above, the same organs were formalin fixed and paraffin embedded to produce FFPE material for analysis by immunohistochemistry with antibodies against Rbphos, Ki67, CDK2phos (active form of CDK2) which should all be high in proliferating tumor cells, but reduced if IpY.19-IRD680 reached its target. Rbphos, Ki67 and CDK2phos levels decreased in the IpY.19-IRD680 treated animals (see FIGS. 33A-33D). Analysis of FFPE material stained with H&E demonstrated that the amount of necrosis was increased in tumor regions in the IpY.19-IRD680 treated animals at the 24 hr timepoint (FIG. 33A), consistent with the rapid induction of necroptosis seen in vitro. This suggesting that at even at this early time point, IpY.19-IRD680 had blocked proliferation and increased cell death.

IpY.19-IRD680 was detected in lung; however, by IVIS imaging, it was not possible to determine whether the lung metastasis or the non-tumor lung tissue had taken up the IpY.19-IRD680.

Example 11

Evaluation of Bioengineered Peptides Efficacy In Vivo

Therapeutic efficacy of the peptide was tested in mouse models using IpY.20 in two different mouse models.

Figure 31C:
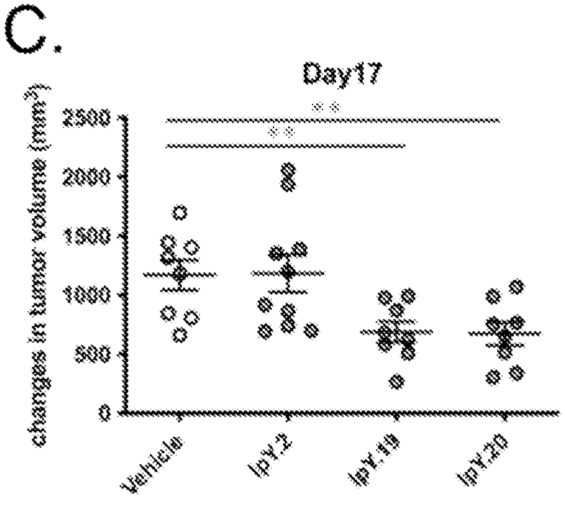

IpY.20 reduces tumor volumes in MCF7 xenograft models. CDX models generated in immunodeficient NOD/SCID animals by injection of MCF7 HR+ BC cells into the 4th mammary gland were treated daily with the parent IpY.2, IpY.19 and IpY.20. IpY.2 was extremely effective at reducing tumor growth in the treatment Naïve MCF7 model and the MCF7 model conditioned to be resistant to palbociclib. This bridging study demonstrated that IpY.19 and IpY.20 performed better than IpY.2, producing a statistically significant reduction in tumor volumes within 17 days of treatment (FIG. 31C).

Figure 34A:
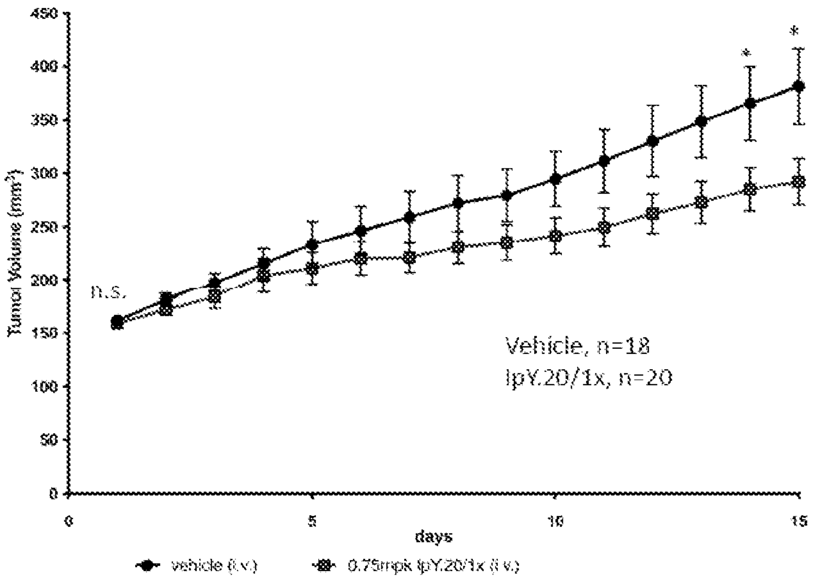
FIGS. 34A-34B illustrate activity of CCL-20 in the model MMTV-Erbb2, an immunocompetent, genetically engineered model (GEM) that overexpresses the potent Erbb2 oncogene.
Figure 34B:
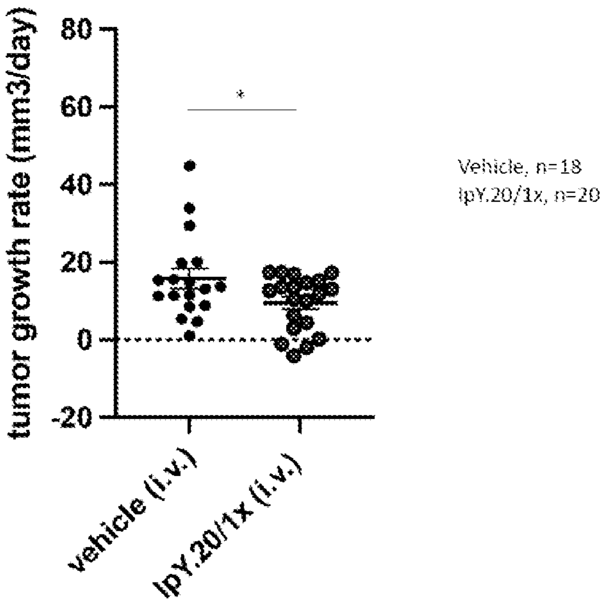

IpY.20 reduces tumor volumes in the Erbb2 mouse model. The MMTV-Erbb2 is an immunocompetent, genetically engineered model (GEM) that overexpresses the potent Erbb2 oncogene. Female Erbb2 animals spontaneously develop mammary tumors in 1 or more mammary glands around 6 months of age. The colony of animals was monitored and when 1 mammary gland had a tumor of ≥150 $mm^3$, it was entered into the study, and treated with vehicle or IpY.20, 3×/week via I.V. IpY.20 reduced tumor volume significantly starting from day 14 post treatment initiation (FIG. 34A) and decreased tumor growth rate significantly during the treatment period (FIG. 34B) The advantage of showing IpY.20 response in this model was 1) the presence of the intact immune system; and 2) the fact that tumors develop within the normal mammary gland with its more intact vascularization, which more closely resembles the metastatic condition in humans. The disadvantage is that these tumors are ER− (all spontaneous mouse tumors are ER−) and while decreased tumor volumes due to lack of tumor progression were observed, no tumor regression was observed. However, this is consistent with the in vitro observations that HR+ tumors undergo necroptosis more specifically than TNBC tumors.

IpY.20 has been shown to have low toxicity in immunocompetent mice, can be delivered specifically to tumors and reduces tumors in multiple breast cancer mouse models, including a spontaneous GEM model where tumors develop within the mammary gland with more physiological vascularization.

Several synthetic batches for CCL-20 were tested and 2 salts were compared. Ion 830-S anion exchange resin (Chloride form, Cl—) or equivalent was converted to acetate form by washing with IM aq NaOH, water, acetic acid, water, and methanol. The resin was dried and stored.

Procedure for Salt Exchange. The peptide CCL-20 in its trifluoroacetate form was dissolved in methanol water and added the anion exchange resin (acetate form) and stirred for 15 min. The resin is filtered and washed with methanol. The methanol is evaporated, and the product is lyophilized and monitored the acetate content by HPLC (Assay). The resulting peptide CCL-20 acetate was purified by HPLC and analyzed by mass spectrometry. Other salts could be produced using similar methodology known to the art.

Figure 35A:
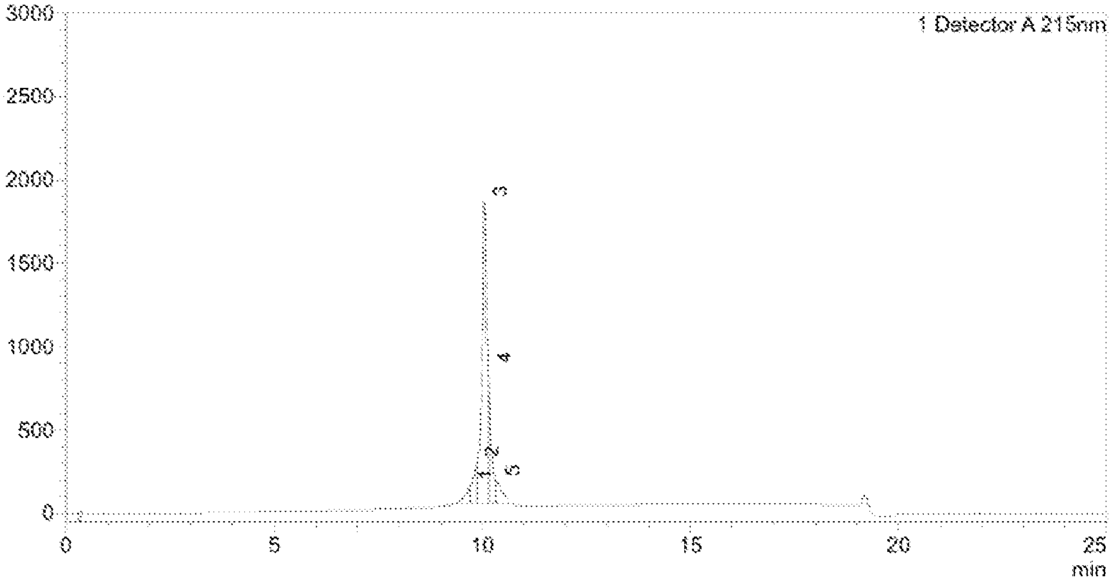
FIGS. 35A-35B illustrate CCL-20 acetate characterization.
Figure 35B:
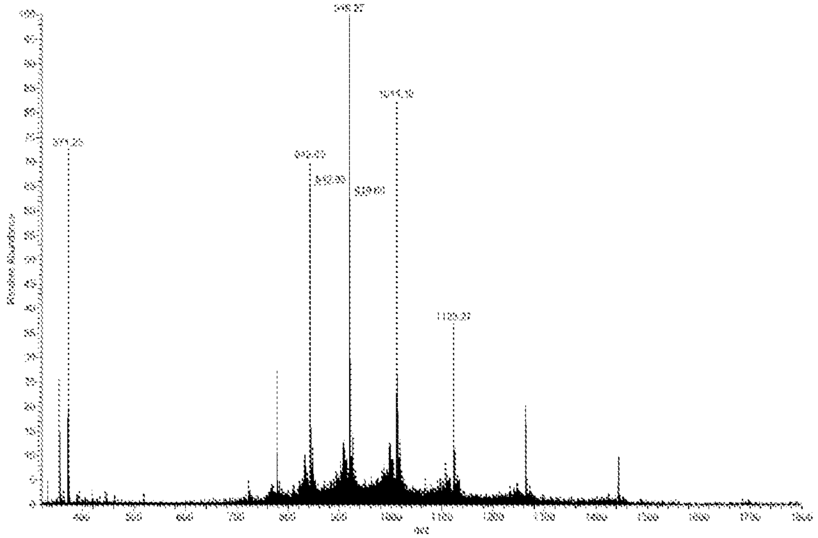
Figure 36:
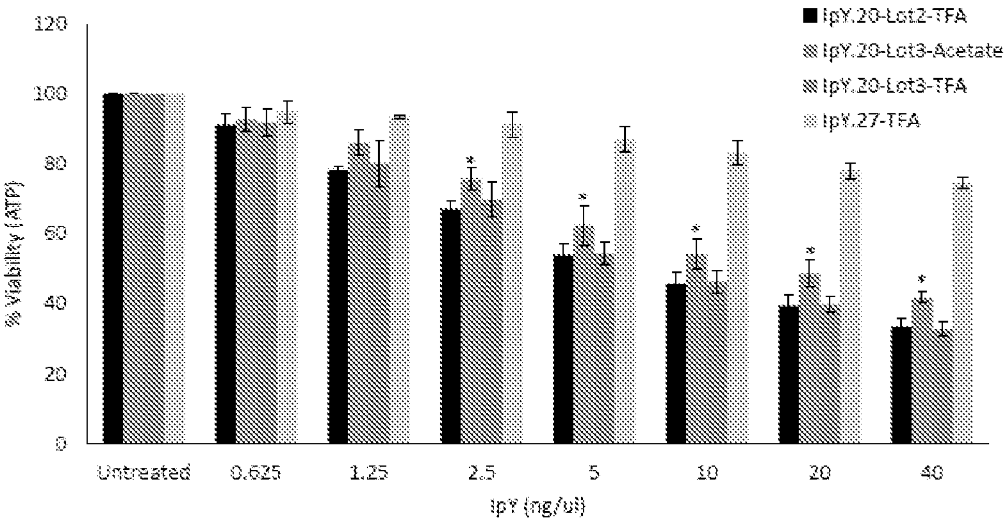
FIG. 36 illustrates the percent viability of MCF7 cells after treatment with 0 ng/ul to 40 ng/ul of peptides for 2 synthetic batches of CCL-20 formulated with IpY. The figure also illustrates the effects of TFA and acetate salt on percent viability of MCF7.

TFA and acetate. Large scale CCL20-Batch #3 TFA and Acetate were tested in ATP driven viability assay side by side with CCL20-batch #2 TFA. Batch 3 TFA behaves the same in MCF7 cells as CCL20-Batch 2 TFA, displaying the same efficacy and thus validating batch consistency and confirming activity. Batch #3 Acetate Fully characterized, (FIG. 35A and 35B), has a moderate but weaker effect, showing some efficacy but has an IC50 of 13.06 ng/ul, almost double that of CCL20-Batch 2 TFA and CCL20-Batch 3-TFA however very clear effect on solubility was observed with the acetate salt and therefore making it a very interesting alternative to the TFA salt. (FIG. 36). MCF7 P.3 cells were treated with 2×24, for a total of 48 hrs and analyzed for ATP viability. Lot 3-acetate went into solution very quickly in about 15 min at 0.5 mg/ml. Lot 3 TFA took 1 h40 min to go into solution at 0.5 mg/ml. Lot2-TFA took 1 h50 min to go into solution at 0.5 mg/ml. serial dilutions were performed in complete media containing 20% HEPES 20 mM.

Figure 37:
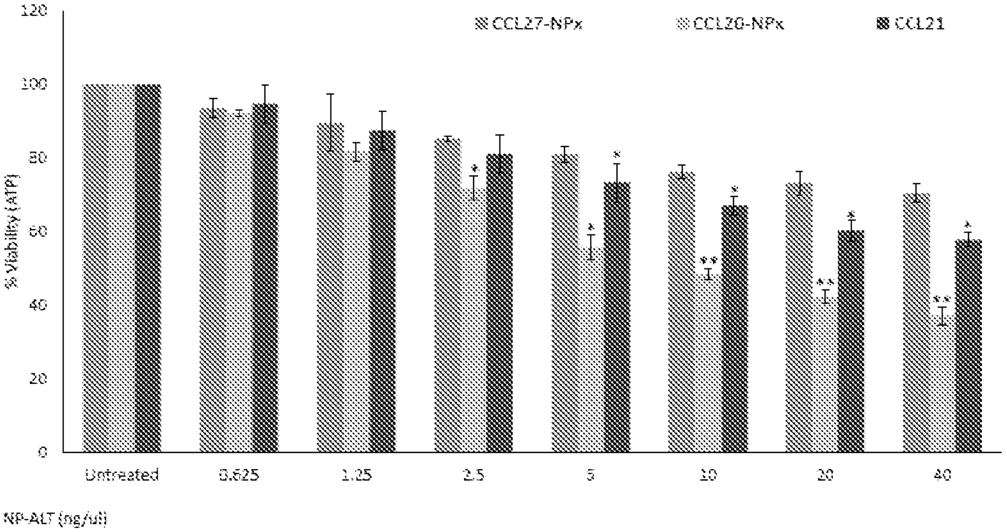
FIG. 37 illustrates the percent viability of MCF7 cells after treatment with 0 ng/ul to 40 ng/ul of peptides for CCL-21, a CPP analogue and CCL-20 formulated with IpY.

CCL21 (CPP derivative) was tested for efficacy in ATP-cell viability assay with CCL20-TFA, CCL19-TFA. MCF7 were plated in 96-well plates and treated with increasing concentrations of CCL-20-LOT1-NPx and CCL-21. CCL-27-NPx was used as a negative control, cells were treated twice every 24 hours for a period of 48 hours and analyzed for ATP-cell viability using Promega cell Titer glo. It was found to have a weaker effect in MCF7 cells compared to CCL20 and CCL19 variants, however the activity of CCL-21 was by far superior to its parent control (peptide without CPP, data not shown) thus demonstrating that CPP added to CCL21 are able to penetrate tumor cell without use of a liposome formulation. (FIG. 37).

Example 12

Evaluation of Bioengineered Peptides Toxicity In Vivo

The toxicity of IpY.20 was assessed in immunocompetent models in repeat dosing experiments.

Figure 38A:
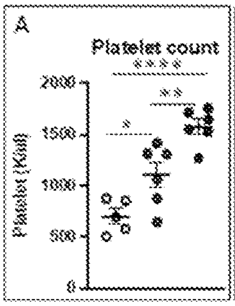
FIGS. 38A-38B illustrate the analysis of the toxicity of CCL-20 in Balb/C mice treated with a vehicle, naked CCL-20 and the encapsulated CCL-20.
Figure 38B:
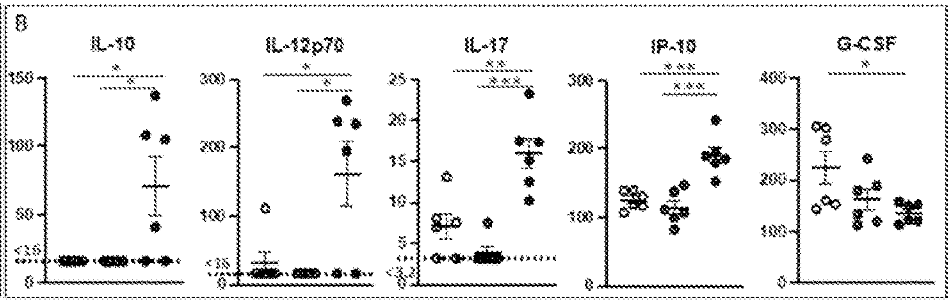

To analyze potential toxicity seen in the presence of IpY.20, immunocompetent BalbC animals were dosed with IpY.20 3×/week at 0.75 mg/kg for 30 days, before euthanasia and analysis for hematology, clinical chemistry, clinical pathology, immunology. In the IpY.20 treated animals, while white blood and red blood cell counts were comparable to those of vehicle-treated mice, there was an increase in platelets (FIG. 38A) and production of specific cytokines (FIG. 38B), suggesting that an immune response may have been initiated. The weight of mice in the IpY.20 treatment arms did not change significantly and treated mice had body condition score (BCS) of 3 based on the BCS guideline throughout the experiment. As a control, animals were dosed with the naked peptide and no effects were seen in this treatment arm (FIGS. 38A and 38B). This effect was not due to the LNP itself as the same LNP formulation was used in toxicity experiments with IpY.2 and no effects were observed. Thus, the toxicity associated with 12 doses of IpY.20 over a 30-day time period were relatively modest.

Although the invention has been described with reference to the above examples, it will be understood that modifications and variations are encompassed within the spirit and scope of the invention. Accordingly, the invention is limited only by the following claims.

What is claimed is:

1. An isolated peptide consisting of the amino acid sequence as set forth in SEQ ID NO: 22 or 23.

2. The isolated peptide of claim 1, wherein the peptide inhibits cancer cell proliferation and/or decreases cancer cell viability.

3. The isolated peptide of claim 1, wherein the peptide inhibits tumor growth.

4. The isolated peptide of claim 1, wherein the peptide increases cancer cell death.

5. The isolated peptide of claim 1, wherein the peptide increases tumor necrosis.

6. A pharmaceutical composition comprising the isolated peptide of claim 1, and a pharmaceutically acceptable carrier.

7. The pharmaceutical composition of claim 6, further comprising a delivery vehicle.

8. The pharmaceutical composition of claim 7, wherein the delivery vehicle is selected from a nanoparticle, a liposome, a dendrimer, a micelle, a nanoemulsion, a nanosuspension, a niosome, a nanocapsule, a magnetic nanoparticle, a lipoprotein-based carrier, or a lipoplex nanoparticle.

9. The pharmaceutical composition of claim 8, wherein the lipoplex nanoparticle comprises 1,2-di-O-octdecenyl-3-trimethyl ammonium propane (DOTMA), cholesterol, DOPE, TPGS, or a combination thereof.

10. The pharmaceutical composition of claim 9, wherein the lipoplex nanoparticle comprises DOTMA and cholesterol at a molar ratio from about 10:90 to 90:10.

11. The pharmaceutical composition of claim 7, wherein the delivery vehicle is coupled with a targeting antibody or an antibody-drug conjugate (ADC).

12. The pharmaceutical composition of claim 6, further comprising at least one anti-cancer agent.

* * * * *

SEQUENCE LISTING

```
<160> NUMBER OF SEQ ID NOS: 50

<210> SEQ ID NO 1
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-1

<400> SEQUENCE: 1

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Cys Ala Ala Leu Gln
                85                  90                  95

Asp Leu Ala Ala Cys Arg Gly Pro Ala Ala Pro Glu Arg Gly Gly Leu
            100                 105                 110

Pro Gln Pro Ala Arg Ala Cys Glu Leu Pro Gln Gly Pro Glu Pro Val
        115                 120                 125

Pro Arg Pro Ala Ala Gly Arg Ala Leu Pro Glu Ala Arg Ala
    130                 135                 140


<210> SEQ ID NO 2
<211> LENGTH: 134
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<223> OTHER INFORMATION: CCL-2

<400> SEQUENCE: 2

```
Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Cys Ala Ala Leu Gln Asp Leu Ala Ala Cys Arg Gly Pro Ala
                85                  90                  95

Ala Pro Glu Arg Gly Gly Val Leu Pro Gln Pro Ala Arg Ala Cys Glu
            100                 105                 110

Leu Pro Gln Gly Pro Glu Pro Val Pro Arg Pro Ala Ala Gly Arg Ala
        115                 120                 125

Leu Pro Glu Ala Arg Ala
    130
```

<210> SEQ ID NO 3
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CCL-2b

<400> SEQUENCE: 3

```
Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Cys Ala Ala Leu Gln Asp Leu Ala Ala Cys Arg Gly Pro Ala
                85                  90                  95

Ala Pro Glu Arg Gly Gly Leu Pro Gln Pro Ala Arg Ala Cys Glu Leu
            100                 105                 110

Pro Gln Gly Pro Glu Pro Val Pro Arg Pro Ala Ala Gly Arg Ala Leu
        115                 120                 125

Pro Glu Ala Arg Ala
    130
```

<210> SEQ ID NO 4
<211> LENGTH: 86
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-3

<400> SEQUENCE: 4

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro
                85


<210> SEQ ID NO 5
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-4a

<400> SEQUENCE: 5

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Ala Ala Ala Ala Ala
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Cys Ala Ala Leu Gln
                85                  90                  95

Asp Leu Ala Ala Cys Arg Gly Pro Ala Ala Pro Glu Arg Gly Gly Leu
            100                 105                 110

Pro Gln Pro Ala Arg Ala Cys Glu Leu Pro Gln Gly Pro Glu Pro Val
        115                 120                 125

Pro Arg Pro Ala Ala Gly Arg Ala Leu Pro Glu Ala Arg Ala
    130                 135                 140


<210> SEQ ID NO 6
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-4b

<400> SEQUENCE: 6
```

Met Val Ser Arg Asp Gln Ala His Leu Gly Pro Lys Tyr Val Gly Leu
1 5 10 15

Trp Asp Phe Lys Ser Arg Thr Asp Glu Glu Leu Ser Phe Arg Ala Gly
20 25 30

Asp Val Phe His Val Ala Arg Lys Glu Glu Gln Trp Trp Trp Ala Thr
35 40 45

Leu Leu Ala Ala Ala Ala Ala Ala Val Ala Gln Gly Tyr Val Pro His
50 55 60

Asn Tyr Leu Ala Glu Arg Glu Thr Val Glu Ser Glu Pro Ala Gly His
65 70 75 80

Ala Gly Cys Ala Ala Leu Gln Asp Leu Ala Ala Cys Arg Gly Pro Ala
85 90 95

Ala Pro Glu Arg Gly Gly Val Leu Pro Gln Pro Ala Arg Ala Cys Glu
100 105 110

Leu Pro Gln Gly Pro Glu Pro Val Pro Arg Pro Ala Ala Gly Arg Ala
115 120 125

Leu Pro Glu Ala Arg Ala
130

<210> SEQ ID NO 7
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-5a

<400> SEQUENCE: 7

Asp Asp Lys Asp Lys Asp Tyr Asp Met Val Ser Arg Asp Gln Ala His
1 5 10 15

Leu Gly Pro Lys Tyr Val Gly Leu Trp Asp Phe Lys Ser Arg Thr Asp
20 25 30

Glu Glu Leu Ser Phe Arg Ala Gly Asp Val Phe His Val Ala Arg Lys
35 40 45

Glu Glu Gln Trp Trp Trp Ala Thr Leu Leu Asp Glu Ala Gly Gly Ala
50 55 60

Val Ala Gln Gly Tyr Val Pro His Asn Tyr Leu Ala Glu Arg Glu Thr
65 70 75 80

Val Glu Ser Glu Pro Ala Gly His Ala Gly Cys Ala Ala Leu Gln Asp
85 90 95

Leu Ala Ala Cys Arg Gly Pro Ala Ala Pro Glu Arg Gly Gly Leu Pro
100 105 110

Gln Pro Ala Arg Ala Cys Glu Leu Pro Gln Gly Pro Glu Pro Val Pro
115 120 125

Arg Pro Ala Ala Gly Arg Ala Leu Pro Glu Ala Arg Ala
130 135 140

<210> SEQ ID NO 8
<211> LENGTH: 142
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-5b

<400> SEQUENCE: 8

Asp Asp Lys Asp Lys Asp Tyr Asp Met Val Ser Arg Asp Gln Ala His
1 5 10 15

Leu Gly Pro Lys Tyr Val Gly Leu Trp Asp Phe Lys Ser Arg Thr Asp
20 25 30

Glu Glu Leu Ser Phe Arg Ala Gly Asp Val Phe His Val Ala Arg Lys
35 40 45

Glu Glu Gln Trp Trp Trp Ala Thr Leu Leu Asp Glu Ala Gly Gly Ala
50 55 60

Val Ala Gln Gly Tyr Val Pro His Asn Tyr Leu Ala Glu Arg Glu Thr
65 70 75 80

Val Glu Ser Glu Pro Ala Gly His Ala Gly Cys Ala Ala Leu Gln Asp
85 90 95

Leu Ala Ala Cys Arg Gly Pro Ala Ala Pro Glu Arg Gly Gly Val Leu
100 105 110

Pro Gln Pro Ala Arg Ala Cys Glu Leu Pro Gln Gly Pro Glu Pro Val
115 120 125

Pro Arg Pro Ala Ala Gly Arg Ala Leu Pro Glu Ala Arg Ala
130 135 140

<210> SEQ ID NO 9
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-6

<400> SEQUENCE: 9

Met Asp Tyr Lys Asp Asp Asp Asp Lys Met Val Ser Arg Asp Gln Ala
1 5 10 15

His Leu Gly Pro Lys Tyr Val Gly Leu Trp Asp Phe Lys Ser Arg Thr
20 25 30

Asp Glu Glu Leu Ser Phe Arg Ala Gly Asp Val Phe His Val Ala Arg
35 40 45

Lys Glu Glu Gln Trp Trp Trp Ala Thr Leu Leu Asp Glu Ala Gly Gly
50 55 60

Ala Val Ala Gln Gly Tyr Val Pro His Asn Tyr Leu Ala Glu Arg Glu
65 70 75 80

Thr Val Glu Ser Glu Pro Ala Gly His Ala Gly Cys Ala Ala Leu Gln
85 90 95

Asp Leu Ala Ala Cys Arg Gly Pro Ala Ala Pro Glu Arg Gly Gly Val
100 105 110

Leu Pro Gln Pro Ala Arg Ala Cys Glu Leu Pro Gln Gly Pro Glu Pro
115 120 125

Val Pro Arg Pro Ala Ala Gly Arg Ala Leu Pro Glu Ala Arg Ala
130 135 140

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-7

<400> SEQUENCE: 10

Met Asp Tyr Lys Asp Asp Asp Asp Lys Met Val Ser Arg Asp Gln Ala
1 5 10 15

His Leu Gly Pro Lys Tyr Val Gly Leu Trp Asp Phe Lys Ser Arg Thr
20 25 30

Asp Glu Glu Leu Ser Phe Arg Ala Gly Asp Val Phe His Val Ala Arg
35 40 45

Lys Glu Glu Gln Trp Trp Trp Ala Thr Leu Leu Asp Glu Ala Gly Gly
50 55 60

Ala Val Ala Gln Gly Tyr Val Pro His Asn Tyr Leu Ala Glu Arg Glu
65 70 75 80

Thr Val Glu Ser Glu Pro Ala Gly His Ala Gly Ser Ala Ala Leu Gln
85 90 95

Asp Leu Ala Ala Ser Arg Gly Pro Ala Ala Pro Glu Arg Gly Gly Leu
100 105 110

Pro Gln Pro Ala Arg Ala
115

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-8

<400> SEQUENCE: 11

Met Asp Tyr Lys Asp Asp Asp Asp Lys Met Val Ser Arg Asp Gln Ala
1 5 10 15

His Leu Gly Pro Lys Tyr Val Gly Leu Trp Asp Phe Lys Arg Ser Thr
20 25 30

Asp Glu Glu Leu Ser Phe Arg Ala Gly Asp Val Phe His Val Ala Arg
35 40 45

Lys Glu Glu Gln Trp Trp Trp Ala Thr Leu Leu Asp Glu Ala Gly Gly
50 55 60

Ala Val Ala Gln Gly Tyr Val Pro His Asn Tyr Leu Ala Glu Arg Glu
65 70 75 80

Thr Val Glu Ser Glu Pro Ala Gly His Ala Gly Ser Ala Ala Leu Gln
85 90 95

Asp Leu Ala Ala Ser Arg Gly Pro Ala Ala Pro Glu Arg Gly Gly Leu
100 105 110

Pro Gln Pro Ala Arg Ala
115

<210> SEQ ID NO 12
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-9

<400> SEQUENCE: 12

Met Asp Tyr Lys Asp Asp Asp Asp Lys Met Val Ser Arg Asp Gln Ala
1 5 10 15

```
His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Cys Ala Ala Leu Gln
                85                  90                  95

Asp Leu Ala Ala
            100


<210> SEQ ID NO 13
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-10

<400> SEQUENCE: 13

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser


<210> SEQ ID NO 14
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-11

<400> SEQUENCE: 14

Lys Tyr Val Gly Leu Trp Asp Phe Lys Ser Arg Thr Asp Glu Glu Leu
1               5                   10                  15

Ser Phe Arg Ala Gly Asp Val Phe His Val Ala Arg Lys Glu Glu Gln
            20                  25                  30

Trp Trp Trp Ala Thr Leu Leu Asp Glu Ala Gly Gly Ala Val Ala Gln
        35                  40                  45

Gly Tyr Val Pro His Asn Tyr Leu Ala Glu Arg Glu Thr Val Glu Ser
    50                  55                  60

Glu Pro Ala Gly His Ala Gly Ser Ala Ala Leu Gln Asp Leu Ala Ala
65                  70                  75                  80

Ser Arg
```

<210> SEQ ID NO 15
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-12

<400> SEQUENCE: 15

```
Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Ser Ala Ala Leu Gln Asp Leu Ala Ala Ser Arg
                85                  90
```

<210> SEQ ID NO 16
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-13

<400> SEQUENCE: 16

```
Lys Tyr Val Gly Leu Trp Asp Phe Lys Ser Arg Thr Asp Glu Glu Leu
1               5                   10                  15

Ser Phe Arg Ala Gly Asp Val Phe His Val Ala Arg Lys Glu Glu Gln
            20                  25                  30

Trp Trp Trp Ala Thr Leu Leu Asp Glu Ala Gly Gly Ala Val Ala Gln
        35                  40                  45

Gly Tyr Val Pro His Asn Tyr Leu Ala Glu Arg Glu Thr Val Glu Ser
    50                  55                  60

Glu Pro Ala Gly His Ala Gly Ser
65                  70
```

<210> SEQ ID NO 17
<211> LENGTH: 83
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CCL-14

<400> SEQUENCE: 17

```
Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
```

```
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Ser


<210> SEQ ID NO 18
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-15

<400> SEQUENCE: 18

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro Gly Gln Ala Pro Val Glu Asp His Gly Arg
                85                  90                  95

Pro Leu Cys Gln Gly Arg Leu Ala Leu Cys Gly Ala Arg Leu Ala Cys
            100                 105                 110

Gln Ala Pro Arg Glu Gly Ala Leu Pro Gly Ala Pro Ala Val Arg Pro
        115                 120                 125

Ala Gly Pro Ala Arg Glu Ala Glu Ala Ala Pro Pro Pro Ala Ala
    130                 135                 140


<210> SEQ ID NO 19
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-16

<400> SEQUENCE: 19

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Ala Ala Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Cys Ala Ala Leu Gln
```

```
                85                  90                  95

Asp Leu Ala Ala Cys Arg Gly Pro Ala Ala Pro Glu Arg Gly Gly Leu
            100                 105                 110

Pro Gln Pro Ala Arg Ala Cys Glu Leu Pro Gln Gly Pro Glu Pro Val
        115                 120                 125

Pro Arg Pro Ala Ala Gly Arg Ala Leu Pro Glu Ala Arg Ala
    130                 135                 140


<210> SEQ ID NO 20
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-17

<400> SEQUENCE: 20

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Ala Ala
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Cys Ala Ala Leu Gln
                85                  90                  95

Asp Leu Ala Ala Cys Arg Gly Pro Ala Ala Pro Glu Arg Gly Gly Leu
            100                 105                 110

Pro Gln Pro Ala Arg Ala Cys Glu Leu Pro Gln Gly Pro Glu Pro Val
        115                 120                 125

Pro Arg Pro Ala Ala Gly Arg Ala Leu Pro Glu Ala Arg Ala
    130                 135                 140


<210> SEQ ID NO 21
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-18

<400> SEQUENCE: 21

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Ala Ala Ala Gly Gly
    50                  55                  60

Ala Val Ala Gln Gly Tyr Val Pro His Asn Tyr Leu Ala Glu Arg Glu
65                  70                  75                  80
```

```
Thr Val Glu Ser Glu Pro Ala Gly His Ala Gly Cys Ala Ala Leu Gln
                85                  90                  95

Asp Leu Ala Ala Cys Arg Gly Pro Ala Ala Pro Glu Arg Gly Gly Leu
            100                 105                 110

Pro Gln Pro Ala Arg Ala Cys Glu Leu Pro Gln Gly Pro Glu Pro Val
        115                 120                 125

Pro Arg Pro Ala Ala Gly Arg Ala Leu Pro Glu Ala Arg Ala
    130                 135                 140


<210> SEQ ID NO 22
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-19

<400> SEQUENCE: 22

Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Cys Ala Ala Leu Gln Asp Leu Ala Ala
                85                  90


<210> SEQ ID NO 23
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-20

<400> SEQUENCE: 23

Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Ser Ala Ala Leu Gln Asp Leu Ala Ala
                85                  90


<210> SEQ ID NO 24
<211> LENGTH: 91
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: CCL-27

<400> SEQUENCE: 24

Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Ala Ala Ala Ala Ala Ala Val Ala Gln Gly Tyr Val Pro His
    50                  55                  60

Asn Tyr Leu Ala Glu Arg Glu Thr Val Glu Ser Glu Pro Ala Gly His
65                  70                  75                  80

Ala Gly Ser Ala Ala Leu Gln Asp Leu Ala Ala
                85                  90


<210> SEQ ID NO 25
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-21

<400> SEQUENCE: 25

Arg Arg Arg Arg Arg Arg Arg Arg Arg Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro Ala Gly His Ala Gly Ser Ala Ala Leu Gln
                85                  90                  95

Asp Leu Ala Ala
            100


<210> SEQ ID NO 26
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-22

<400> SEQUENCE: 26

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30
```

```
Asp Ala Ala Leu Ser Phe Arg Ala Gly Asp Val Phe His Val Ala Arg
        35                  40                  45

Lys Glu Glu Gln Trp Trp Trp Ala Thr Leu Leu Asp Glu Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro
                85


<210> SEQ ID NO 27
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-23

<400> SEQUENCE: 27

Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Asp Glu Ala Ala Ala
    50                  55                  60

Ala Val Ala Gln Gly Tyr Val Pro His Asn Tyr Leu Ala Glu Arg Glu
65                  70                  75                  80

Thr Val Glu Ser Glu Pro
                85


<210> SEQ ID NO 28
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CCL-24

<400> SEQUENCE: 28

Met Asp Tyr Lys Asp Asp Asp Asp Lys Met Asp Tyr Lys Asp Asp Asp
1               5                   10                  15

Asp Lys Gly Gly Val Thr Thr Phe Val Ala Leu Tyr Asp Tyr Glu Ser
            20                  25                  30

Arg Thr Glu Thr Asp Leu Ser Phe Lys Lys Gly Glu Arg Leu Gln Ile
        35                  40                  45

Val Asn Asn Thr Glu Gly Asp Trp Trp Leu Ala His Ser Leu Ser Asp
    50                  55                  60

Glu Ala Gly Gly Thr Gly Gln Thr Gly Tyr Ile Pro Ser Asn Tyr Val
65                  70                  75                  80

Ala Pro Ser Asp Ser Ile Gln Ala
                85


<210> SEQ ID NO 29
<211> LENGTH: 86
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<223> OTHER INFORMATION: CCL-25

<400> SEQUENCE: 29

```
Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Ala Ala Ala Gly Gly
    50                  55                  60

Ala Val Ala Gln Gly Tyr Val Pro His Asn Tyr Leu Ala Glu Arg Glu
65                  70                  75                  80

Thr Val Glu Ser Glu Pro
                85
```

<210> SEQ ID NO 30
<211> LENGTH: 86
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CCL-26

<400> SEQUENCE: 30

```
Met Asp Tyr Lys Asp Asp Asp Asp Lys Met Val Ser Arg Asp Gln Ala
1               5                   10                  15

His Leu Gly Pro Lys Tyr Val Gly Leu Trp Asp Phe Lys Ser Arg Thr
            20                  25                  30

Asp Glu Glu Leu Ser Phe Arg Ala Gly Asp Val Phe His Val Ala Arg
        35                  40                  45

Lys Glu Glu Gln Trp Trp Trp Ala Thr Leu Leu Ala Ala Ala Ala Ala
    50                  55                  60

Ala Val Ala Gln Gly Tyr Val Pro His Asn Tyr Leu Ala Glu Arg Glu
65                  70                  75                  80

Thr Val Glu Ser Glu Pro
                85
```

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: penetratin

<400> SEQUENCE: 31

```
Arg Gln Ile Lys Ile Trp Phe Gln Asn Arg Arg Met Lys Trp Lys Lys
1               5                   10                  15
```

<210> SEQ ID NO 32
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: Tat peptide

<400> SEQUENCE: 32

Gly Arg Lys Lys Arg Arg Gln Arg Arg Arg Pro Pro Gln
1               5                   10

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: pVEC

<400> SEQUENCE: 33

Leu Leu Ile Ile Leu Arg Arg Arg Ile Arg Lys Gln Ala His Ala His
1               5                   10                  15

Ser Lys

<210> SEQ ID NO 34
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: chimeric transportan

<400> SEQUENCE: 34

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: MPG peptide

<400> SEQUENCE: 35

Gly Ala Leu Phe Leu Gly Phe Leu Gly Ala Ala Gly Ser Thr Met Gly
1               5                   10                  15

Ala Trp Ser Pro Lys Lys Lys Arg Lys Val
            20                  25

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Pep-1

<400> SEQUENCE: 36

-continued

Lys Glu Thr Trp Trp Glu Thr Trp Trp Thr Glu Trp Ser Gln Pro Lys
1 5 10 15

Lys Lys Arg Lys Val
20

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic polyarginines R8

<400> SEQUENCE: 37

Arg Arg Arg Arg Arg Arg Arg Arg
1 5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic polyarginines R9

<400> SEQUENCE: 38

Arg Arg Arg Arg Arg Arg Arg Arg Arg
1 5

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: MAP

<400> SEQUENCE: 39

Lys Leu Ala Leu Lys Leu Ala Leu Lys Ala Leu Lys Ala Ala Leu Lys
1 5 10 15

Leu Ala

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: R6W3

<400> SEQUENCE: 40

Arg Arg Trp Trp Arg Arg Trp Arg Arg
1 5

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: P28 (azurin 50-77)

<400> SEQUENCE: 41

Leu Ser Thr Ala Ala Asp Met Gln Gly Val Val Thr Asp Gly Met Ala
1 5 10 15

Ser Gly Leu Asp Lys Asp Tyr Leu Lys Pro Asp Asp
20 25

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: point mutation 1

<400> SEQUENCE: 42

Pro Pro Pro Pro
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: point mutation 2

<400> SEQUENCE: 43

Ala Ala Ala Ala
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: point mutation 3

<400> SEQUENCE: 44

Pro Lys Lys Pro
1

<210> SEQ ID NO 45
<211> LENGTH: 134
<212> TYPE: PRT
<213> ORGANISM: Homo sapiens
<220> FEATURE:
<223> OTHER INFORMATION: Alt-Brk

<400> SEQUENCE: 45

Met Val Ser Arg Asp Gln Ala His Leu Gly Pro Lys Tyr Val Gly Leu
1 5 10 15

Trp Asp Phe Lys Ser Arg Thr Asp Glu Glu Leu Ser Phe Arg Ala Gly
20 25 30

Asp Val Phe His Val Ala Arg Lys Glu Glu Gln Trp Trp Trp Ala Thr
35 40 45

Leu Leu Asp Glu Ala Gly Gly Ala Val Ala Gln Gly Tyr Val Pro His
50 55 60

Asn Tyr Leu Ala Glu Arg Glu Thr Val Glu Ser Glu Pro Ala Gly His
65 70 75 80

Ala Gly Cys Ala Ala Leu Gln Asp Leu Ala Ala Cys Arg Gly Pro Ala
85 90 95

Ala Pro Glu Arg Gly Gly Val Leu Pro Gln Pro Ala Arg Ala Cys Glu
100 105 110

Leu Pro Gln Gly Pro Glu Pro Val Pro Arg Pro Ala Ala Gly Arg Ala
115 120 125

Leu Pro Glu Ala Arg Ala
130

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SH3 domain variation

<400> SEQUENCE: 46

Asp Glu Ala Gly Gly Ala Ala Ala Ala Ala
1 5 10

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SH3 domain variation

<400> SEQUENCE: 47

Glu Glu Ala Ala
1

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SH3 domain variation

<400> SEQUENCE: 48

Asp Glu Ala Gly Gly Asp Glu Ala Ala Ala
1 5 10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SH3 domain variation

<400> SEQUENCE: 49

-continued

```
Asp Glu Ala Gly Gly Ala Ala Ala Gly Gly
1               5                   10


<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SH3 domain variation

<400> SEQUENCE: 50

Asp Glu Ala Gly Gly
1               5
```